(12) United States Patent
Sasaki et al.

(10) Patent No.: US 7,563,901 B2
(45) Date of Patent: Jul. 21, 2009

(54) INTERMEDIATES OF 2-SUBSTITUTED CARBAPENEM DERIVATIVES AND PROCESS FOR PRODUCTION THEREOF

(75) Inventors: Toshiro Sasaki, Yokohama (JP); Takashi Ando, Yokohama (JP); Yasuo Yamamoto, Yokohama (JP); Takahiro Imai, Yokohama (JP); Dai Kubota, Yokohama (JP); Katsuhiko Noguchi, Yokohama (JP); Nobuyuki Hori, Yokohama (JP); Eiki Shitara, Yokohama (JP); Kunio Atsumi, Yokohama (JP); Shohei Yasuda, Odawara (JP)

(73) Assignee: Meiji Seika Kaisha, Ltd., Tokyo-to (JP)

( * ) Notice: Subject to any disclaimer, the term of this patent is extended or adjusted under 35 U.S.C. 154(b) by 0 days.

(21) Appl. No.: 12/071,120

(22) Filed: Feb. 15, 2008

(65) Prior Publication Data

US 2008/0167475 A1 Jul. 10, 2008

Related U.S. Application Data

(62) Division of application No. 10/538,466, filed as application No. PCT/JP03/16036 on Dec. 15, 2003.

(30) Foreign Application Priority Data

Dec. 13, 2002 (JP) ............................. 2002-361757

(51) Int. Cl.
*C07D 513/02* (2006.01)
*A61K 31/429* (2006.01)

(52) U.S. Cl. ...................... 548/154; 548/146; 548/148; 548/152; 548/153; 514/365; 514/367; 514/368

(58) Field of Classification Search ................. 548/146, 548/148, 152, 153, 154; 514/365, 367, 368
See application file for complete search history.

(56) References Cited

U.S. PATENT DOCUMENTS

| | | | | |
|---|---|---|---|---|
| 6,310,056 | B1 * | 10/2001 | Kano et al. | ............. 514/210.14 |
| 6,458,780 | B1 * | 10/2002 | Kano et al. | ............. 514/210.09 |
| 6,677,331 | B2 * | 1/2004 | Kano et al. | ............. 514/210.09 |
| 6,825,187 | B2 * | 11/2004 | Kano et al. | ............. 514/210.09 |

FOREIGN PATENT DOCUMENTS

| | | |
|---|---|---|
| JP | 8-311071 A | 11/1996 |
| JP | 2003-26686 A | 1/2003 |
| WO | 01/53305 A1 | 7/2001 |
| WO | 01/55155 A1 | 8/2001 |
| WO | 02/42312 A1 | 5/2002 |

OTHER PUBLICATIONS

Supplementary European Search Report in EP 03778922, issued Jul. 5, 2007.

* cited by examiner

*Primary Examiner*—Golam M Shameem
(74) *Attorney, Agent, or Firm*—Wenderoth, Lind & Ponack, L.L.P.

(57) ABSTRACT

The present invention relates to compounds represented by formula (1) and a process for producing the same. The use of these compounds can realize the production of carbapenem derivatives having potent antimicrobial activity and a wide antimicrobial spectrum in a safe and cost-effective manner.

4 Claims, No Drawings

INTERMEDIATES OF 2-SUBSTITUTED CARBAPENEM DERIVATIVES AND PROCESS FOR PRODUCTION THEREOF

This is a divisional of Ser. No. 10/538,466, filed Jun. 10, 2005 which is a 371 of PCT/JP03/16036, filed Dec. 15, 2003.

BACKGROUND OF THE INVENTION

1. Field of the Invention

The present invention relates to novel synthetic intermediates for the production of carbapenem derivatives, which have excellent antimicrobial activity and a broad antimicrobial spectrum, and a process for the production thereof.

2. Related Art

Carbapenem derivatives have high antimicrobial activity and a broad excellent antimicrobial spectrum and thus have been energetically studied as a highly useful β-lactam agent.

In WO 02/42312, the present inventors have reported their finding that carbapenem derivatives having a 7-(1-carbamoylmethylpyridinium-3-yl)carbonylimidazo[5,1-b]thiazole group at the 2-position on the carbapenem ring, that is, compounds of formula (A), have high antimicrobial activity against Gram-positive bacteria and Gram-negative bacteria including MRSA (methicillin resistant *Staphylococcus aureus*), PRSP (penicillin resistant *Streptococcus pneumoniae*), *Haemophilus influenzae*, and β-lactamase producing bacteria, and, at the same time, have high stability against DHP-1 (kidney dehydropeptidase-1). In this publication, a production process shown in scheme A below is disclosed as a production process of such derivatives.

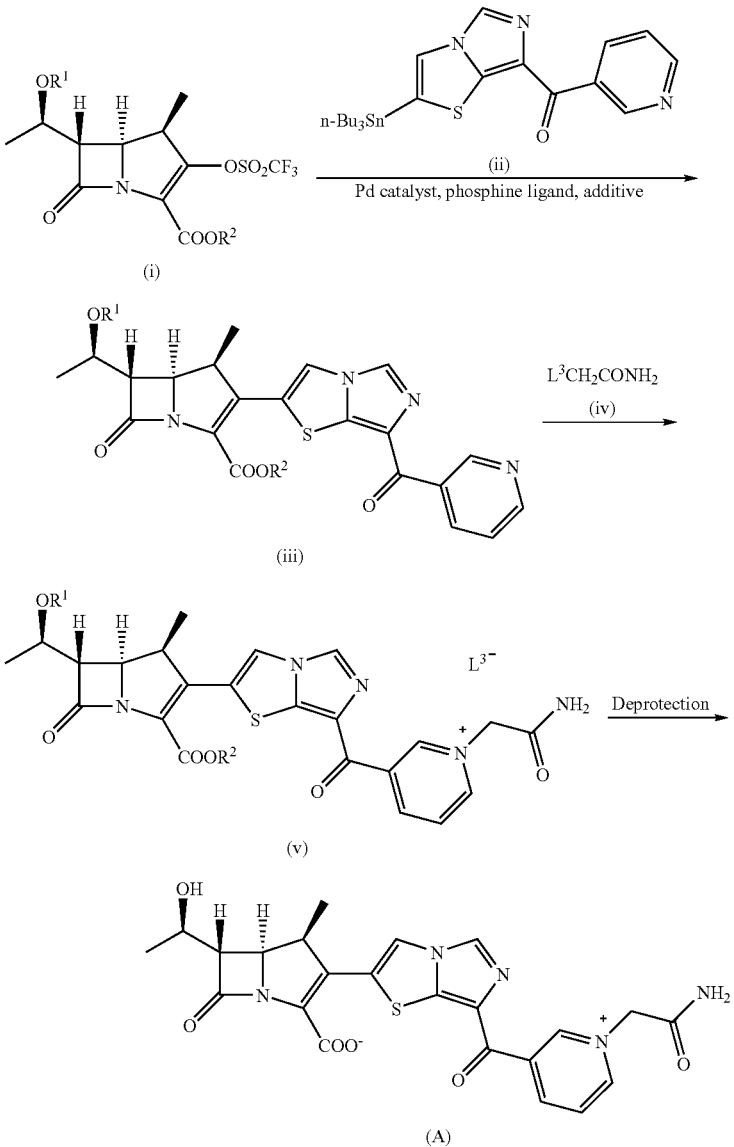

Scheme A:

wherein $R^1$ represents a hydrogen atom or represents a protective group of hydroxyl; $R^2$ represents a protective group of carboxyl; and $L^3$ represents a leaving group.

According to this production process, the compound of formula (A) is produced by reacting a compound of formula (i) with a compound of formula (ii) in the presence of a palladium catalyst, a phosphine ligand, and an additive to give a compound of formula (iii), subsequently reacting the compound of formula (iii) with a compound of formula (iv) to give a compound of formula (v), and then deprotecting the compound of formula (v).

However, the compound of formula (ii) used in this process and reagents such as a trialkyltin chloride used for preparing this compound belong to organotin compounds and are known to be highly toxic. Further, the palladium catalyst and the phosphine ligand used in the reaction of the compound of formula (i) with the compound of formula (ii) are generally expensive. Therefore, a process which can produce the carbapenem derivatives of formula (A) in a highly safe and more cost-effective manner has been desired.

SUMMARY OF THE INVENTION

The present inventors have now succeeded in producing compounds represented by formula (1), which will be described later, as a synthetic intermediate for carbapenem derivatives represented by formula (A). Specifically, compounds represented by formula (2) which will be described later could be produced as a precursor of carbapenem derivatives represented by formula (A) by treating the compound represented by formula (1) under conditions, which can form a carbapenem ring, to form a carbapenem ring through a ring-closing reaction. The production process using the compound of formula (1) does not need to use any highly toxic compound such as the organotin compound and does not substantially use expensive chemicals such as a palladium catalyst. The present invention has been made based on such finding.

Accordingly, an object of the present invention is to provide a production process, which can produce carbapenem derivatives represented by formula (A) in an efficient, safe and cost-effective manner, and a synthetic intermediate for use in said production process.

According to the present invention, there is provided a compound represented by formula (1):

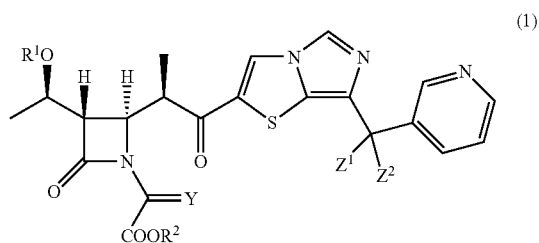

(1)

wherein $R^1$ represents a hydrogen atom or a protective group of hydroxyl, $R^2$ represents a hydrogen atom, a protective group of carboxyl, or an anion in a carboxylate anion, $Z^1$ and $Z^2$ together represent an oxygen atom or a protective group of carbonyl, or one of $Z^1$ and $Z^2$ represents a hydrogen atom and the other represents hydroxyl or protected hydroxyl, Y represents an oxygen atom or group $P(R^3)_3$, wherein $R^3$s, which may be the same or different, represent C1-6 alkyl optionally substituted by a halogen atom, or aryl optionally substituted by a halogen atom or C1-6 alkyl in which the alkyl group may be substituted by a halogen atom.

According to another aspect of the present invention, there is provided a process for producing a compound represented by formula (1) wherein Y represents group $P(R^3)_3$, said process comprising the step of reacting a reaction mixture, prepared by treating a compound of formula (4') with a Grignard reagent, with a compound of formula (5):

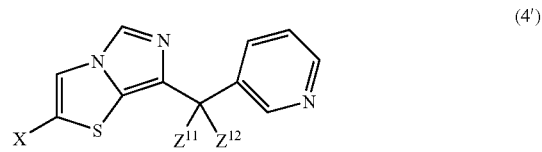

(4')

wherein $Z^{11}$ and $Z^{12}$ together represent an oxygen atom or a protective group of carbonyl, or one of $Z^{11}$ and $Z^{12}$ represents a hydrogen atom and the other represents protected hydroxyl, and X represents a halogen atom; and

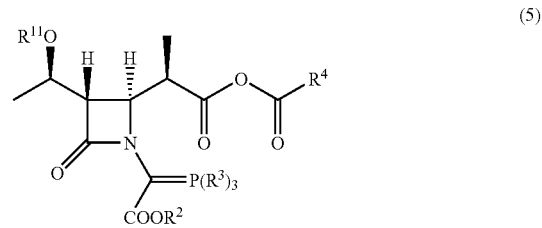

(5)

wherein $R^{11}$ represents a protective group of hydroxyl, $R^2$ and $R^3$ are as defined in formula (1), and $R^4$ represents optionally substituted C1-6 alkyl, or aryl optionally substituted by a group selected from the group consisting of a halogen atom, optionally substituted C1-6 alkyl, optionally substituted C1-6 alkoxy, and —$NR^5R^6$, wherein $R^5$ and $R^6$, which may be the same or different, represent C1-6 alkyl, or $R^5$ and $R^6$ together represent —$(CH_2)_n$— wherein n is an integer of 2 to 6.

In a preferred embodiment of the present invention, the process for producing a compound represented by formula (1), wherein Y represents group $P(R^3)_3$, further comprises preparing the compound of formula (4') by steps (c) and (d):

(c) formylating a compound of formula (14) with a Vilsmeyer complex to give a compound of formula (18):

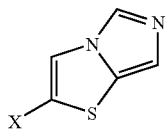
(14)

wherein X represents a halogen atom, and

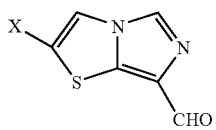
(18)

wherein X represents a halogen atom, and (d) reacting the compound of formula (18) with a 3-metallopyridine of formula (19) to give a compound of formula (4') in which one of $Z^{11}$ and $Z^{12}$ represents a hydrogen atom and the other represents hydroxyl, and either protecting hydroxyl in this compound, or oxidizing hydroxyl in this compound and protecting carbonyl in the resultant compound, to give the compound of formula (4'):

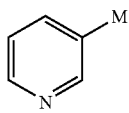
(19)

wherein M represents lithium, MgBr, or MgI.

In a preferred embodiment of the present invention, the process for producing a compound represented by formula (1), wherein Y represents group $P(R^3)_3$, further comprises preparing the compound of formula (14) by steps (a) and (b):

(a) reacting a compound of formula (15) with a halogenating agent to give a compound of formula (16) and formulating the amino group in the compound of formula (16) optionally after removing the protective group, to give a compound of formula (17):

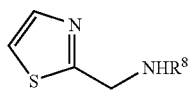
(15)

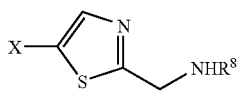
(16)

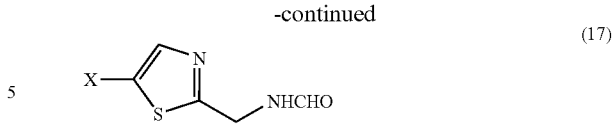
(17)

wherein
$R^8$ represents a hydrogen atom, or a protective group of amino and
X represents a halogen atom, and (b) reacting the compound of formula (17) with a dehydrating agent for cyclization to give a compound of formula (14).

According to still another aspect of the present invention, there is provided a process for producing a compound represented by formula (1) wherein Y represents an oxygen atom, said process comprising the step of reacting a compound of formula (8) with a compound of formula (9) in the presence of a base:

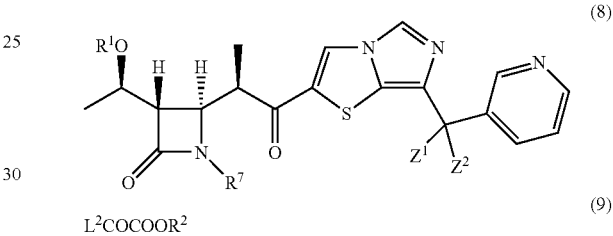
(8)

$$L^2COCOOR^2$$ (9)

wherein
$R^7$ represents a hydrogen atom, or a protective group of amino,
$R^1$, $R^2$, $Z^1$ and $Z^2$ are as defined in formula (1), and
$L^2$ represents a leaving group.

In a preferred embodiment of the present invention, the process for producing a compound represented by formula (1), wherein Y represents an oxygen atom, further comprises preparing the compound of formula (8) by step (f):

(f) reacting a compound, prepared by treating a compound of formula (6') with an alkali metal base, or a base and a monovalent to tetravalent metal compound, with a compound of formula (7), and optionally removing a protective group and/or introducing a protective group and/or conducting oxidization to give a compound of formula (8):

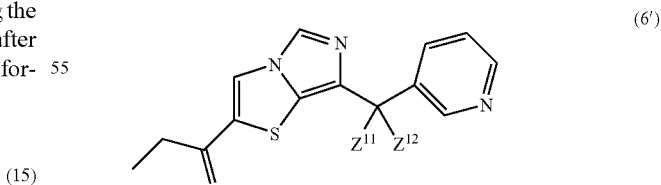
(6')

wherein
$Z^{11}$ and $Z^{12}$ together represent an oxygen atom, or a protective group of carbonyl, or
one of $Z^{11}$ and $Z^{12}$ represents a hydrogen atom and the other represents protected hydroxyl; and

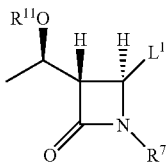

(7)

wherein

R¹¹ represents a protective group of hydroxyl,

R⁷ represents a hydrogen atom or a protective group of amino, and

L¹ represents a leaving group.

In a preferred embodiment of the present invention, the process for producing a compound represented by formula (1), wherein Y represents an oxygen atom, further comprises preparing a compound of formula (6') by steps (c), (d) and (e):

(c) formulating a compound of formula (14) with a Vilsmeyer complex to give a compound of formula (18):

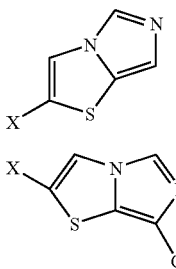

(14)

(18)

wherein X represents a halogen atom, (d) reacting the compound of formula (18) with a 3-metallopyridine of formula (19) to give a compound of formula (4') wherein one of $Z^{11}$ and $Z^{12}$ represents a hydrogen atom and the other represents hydroxyl, and either protecting hydroxyl in this compound, or oxidizing hydroxyl in this compound and protecting carbonyl in the resultant compound, to give a compound of formula (4'):

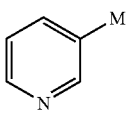

(19)

wherein M represents lithium, MgBr, or MgI, and (e) reacting a compound, prepared by treating the compound of formula (4') with a Grignard reagent, with a propionic acid derivative to give a compound of formula (6').

In a preferred embodiment of the present invention, the process for producing a compound represented by formula (1), wherein Y represents an oxygen atom, further comprises preparing a compound of formula (14) by steps (a) and (b):

(a) reacting a compound of formula (15) with a halogenating agent to give a compound of formula (16) which, optionally after the removal of a protective group, undergoes formulation of amino to give a compound of formula (17):

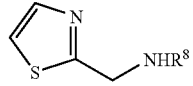

(15)

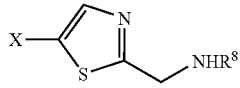

(16)

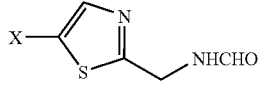

(17)

wherein

R⁸ represents a hydrogen atom, or a protective group of amino, and

X represents a halogen atom, and (b) reacting the compound of formula (17) with a dehydrating agent for cyclization to give a compound of formula (14).

According to a further aspect of the present invention, there is provided a process for producing a compound represented by formula (1), wherein Y represents group P(R³)₃, said process comprising the steps of halogening hydroxyl in a compound of formula (11), prepared by reacting a compound of formula (8) with a compound of formula (10) or its reactive equivalent, with a halogenating agent, and reacting the resultant compound with a compound of formula (13):

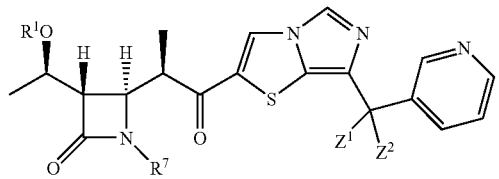

(8)

HC(=O)—COOR² (10)

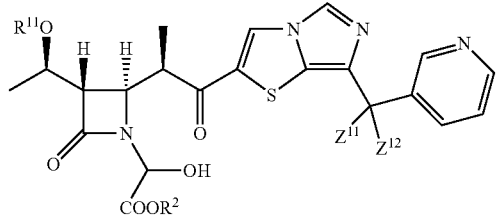

(11)

P(R³)₃ (13)

wherein

R¹¹ represents a protective group of hydroxyl,

R¹, R², and R³ are as defined in formula (1),

R⁷ represents a hydrogen atom,

Z¹ and Z² together represent an oxygen atom, or a protective group of carbonyl, or, one of Z¹ and Z² represents a hydrogen atom and the other represents hydroxyl or protected hydroxyl, $Z^{11}$ and $Z^{12}$ together represent an oxygen atom, or a protective group of carbonyl, or one of $Z^{11}$ and $Z^{12}$ represents a hydrogen atom and the other represents protected hydroxyl.

According to another aspect of the present invention, there is provided a process for producing a compound of formula (2), said process comprising the steps of treating a compound of formula (1) under conditions, which can form a carbapenem ring, to form a carbapenem ring through a ring-closing reaction and optionally conducting the removal of a protective group and/or oxidation:

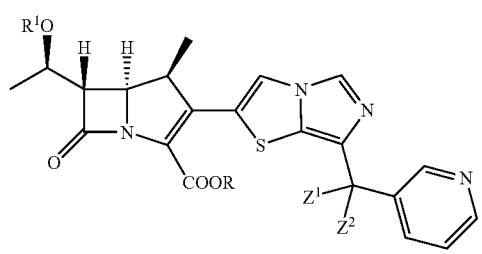

(2)

wherein $R^1$ represents a hydrogen atom, or represents a protective group of hydroxyl, R represents a hydrogen atom, a protective group of carboxyl, or an anion in a carboxylate anion, $Z^1$ and $Z^2$ together represent an oxygen atom, or a protective group of carbonyl, or one of $Z^1$ and $Z^2$ represents a hydrogen atom and the other represents hydroxyl or protected hydroxyl.

According to still another aspect of the present invention, there is provided a process for producing a compound of formula (A), comprising the step of preparing the compound of formula (2) from the compound of formula (1) by the above process for producing a compound of formula (2):

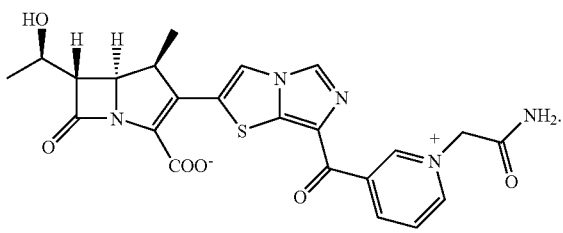

(A)

In a preferred embodiment of the present invention, the process for producing a compound represented by formula (A) further comprises the step of reacting the compound of formula (2) with a compound of formula (iv) to give a compound of formula (3):

$L^3CH_2CONH_2$ (iv)

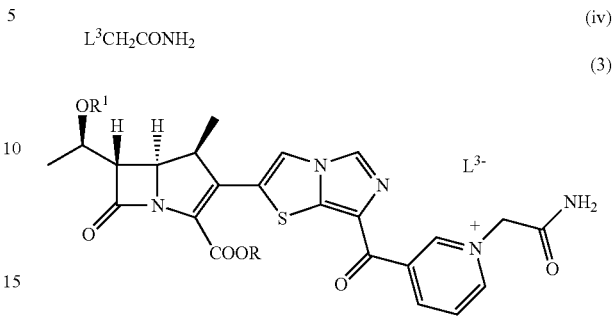

(3)

wherein $L^3$ represents a leaving group, $R^1$ represents a hydrogen atom, or represents a protective group of hydroxyl, and R represents a hydrogen atom, a protective group of carboxyl, or an anion in a carboxylate anion.

In a preferred embodiment of the present invention, the process for producing a compound represented by formula (A) further comprises the step of removing the protective group in the compound of formula (3) by a deprotection reaction to give the compound of formula (A).

In a further preferred embodiment of the present invention, the process for producing a compound of formula (A) further comprises the step of preparing the compound of formula (1) by one of the production processes of the compound of formula (1).

According to the present invention, there is also provided a compound represented by formula (4):

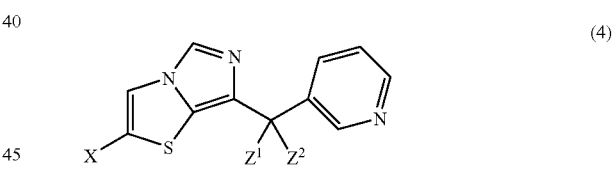

(4)

wherein $Z^1$ and $Z^2$ together represent an oxygen atom, or a protective group of carbonyl, or one of $Z^1$ and $Z^2$ represents a hydrogen atom and the other represents hydroxyl or protected hydroxyl, and X represents a halogen atom.

According to the present invention, there is also provided a compound represented by formula (6):

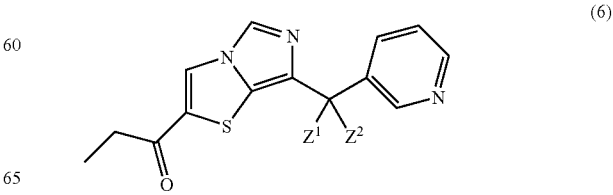

(6)

wherein $Z^1$ and $Z^2$ together represent an oxygen atom, or a protective group of carbonyl, or one of $Z^1$ and $Z^2$ represents a hydrogen atom and the other represents hydroxyl or protected hydroxyl.

According to the present invention, there is further provided a compound represented by formula (8):

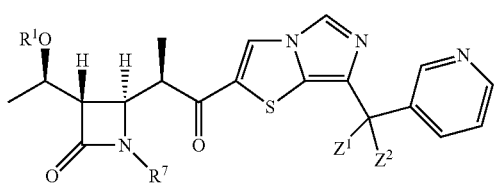
(8)

wherein $R^1$ represents a hydrogen atom, or represents a protective group of hydroxyl, $Z^1$ and $Z^2$ together represent an oxygen atom, or a protective group of carbonyl, or one of $Z^1$ and $Z^2$ represents a hydrogen atom and the other represents hydroxyl or protected hydroxyl, and $R^7$ represents a hydrogen atom, or a protective group of amino.

According to the present invention, there is also provided a compound represented by formula (14a):

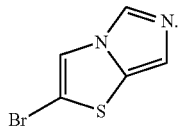
(14a)

In a further aspect of the present invention, there is provided use of a compound of formula (1) according to the present invention, as a synthetic intermediate for the production of an antimicrobial agent.

DETAILED DESCRIPTION OF THE INVENTION

The term "alkyl" as used herein as a group or a part of a group means straight chain, branched chain, or cyclic, either alone or in combination, alkyl, unless otherwise specified. "C1-6," for example, in "C1-6 alkyl" means that the alkyl group has 1 to 6 carbon atoms.

"C1-6 alkyl" is preferably C1-4 alkyl, more preferably C1-3 alkyl. Examples of alkyl include methyl, ethyl, n-propyl, isopropyl, n-butyl, i-butyl, s-butyl, t-butyl, n-pentyl, and n-hexyl.

The term "alkoxy" as used herein as a group or a part of a group means straight chain, branched chain, or cyclic, either alone or in combination, alkoxy.

"C1-6 alkoxy" is preferably C1-4 alkoxy, more preferably C1-3 alkoxy. Examples of alkoxy include methoxy, ethoxy, n-propoxy, i-propoxy, n-butoxy, i-butoxy, s-butoxy, and t-butoxy.

The term "alkenyl" as used herein as a group or a part of a group means straight chain, branched chain, or cyclic, either alone or in combination, alkenyl. Preferably, alkenyl is straight chain or branched chain alkenyl. The number of double bonds contained in the alkenyl part in the group is not particularly limited, and the double bond may be in Z-configuration or E-configuration. Alkenyl is, for example, C2-6 alkenyl. "C2-6 alkenyl" is preferably C2-5 alkenyl, more preferably C2-4 alkenyl. Examples of alkenyl include vinyl, allyl, propenyl, isopropenyl, butenyl, 2-butenyl, 3-butenyl, 2-methyl-1-propenyl, 2-methylallyl, pentenyl, 2-pentenyl, cyclopentenyl, hexenyl, 2-hexenyl, and cyclohexenyl.

The term "halogen atom" as used herein means a fluorine, chlorine, bromine, or iodine atom. Preferably, the halogen atom is a chlorine, bromine, or iodine atom.

The term "aryl" as used herein as a group or a part of a group means a six- to fourteen-membered monocyclic to tricyclic aromatic carbocylic ring. Preferably, aryl is a five- to seven-membered aromatic monocyclic carbocyclic ring or an eight- to twelve-membered aromatic bicyclic carbocyclic ring. Examples of aryl include phenyl, 1-naphthyl, 2-naphthyl, biphenyl, 2-anthrylnaphthy. In the present invention, aryl is particularly preferably phenyl.

The term "aralkyl" as used herein as a group or a part of a group means C1-6 alkyl substituted by the above aryl. Here in the alkyl or aryl part, one or more hydrogen atoms on the group may be substituted by one or more substituents which may be the same or different. Examples of substituents include nitro, a halogen atom, C1-6 alkyl, and C1-6 alkoxy. The C1-6 alkyl part in the aralkyl group is preferably C1-4 alkyl, more preferably C1-3 alkyl, still more preferably C1-2 alkyl. Examples of aralkyl include benzyl, diphenylmethyl, trityl, phenethyl, 4-methoxybenzyl, 2-nitrobenzyl, and 4-nitrobenzyl (pNB).

The term "acyl" that is used herein as a group or a part of a group means straight chain, branched chain, or cyclic acyl. The acyl group may be, for example, include C1-8 acyl, preferably C1-6 acyl, more preferably C1-4 acyl. Examples of acyl include formyl, alkylcarbonyl, aralkylcarbonyl, arylcarbonyl, specifically, for example, formyl, acetyl, propionyl, butyryl, toluoyl, anisoyl, and benzoyl.

The expression "optionally substituted" alkyl as used herein means that one or more hydrogen atoms on the alkyl group are optionally substituted by one or more substituents which may be the same or different. It will be apparent to a person having ordinary skill in the art that the maximum number of substituents may be determined depending upon the number of substitutable hydrogen atoms on the alkyl group. This is true of alkoxy, alkenyl or other groups.

The protective group of hydroxyl which may be represented by $R^1$ or $R^{11}$ is not particularly limited so far as the protective group of hydroxyl is usually used in the synthesis of carbapenem derivatives and may be properly selected by a person having ordinary skill in the art. Such protective groups of hydroxyl include, for example, silyl such as t-butyldimethylsilyl, trimethylsilyl, and triethylsilyl; and oxycarbonyl such as 4-nitrobenzyloxycarbonyl, 4-methoxybenzyloxycarbonyl, and allyloxycarbonyl. Preferably, the protective group of hydroxyl which may be represented by $R^1$ or $R^{11}$ is silyl such as t-butyldimethylsilyl, trimethylsilyl, or triethylsilyl, more preferably t-butyldimethylsilyl or triethylsilyl.

$R^1$ or $R^{11}$ is preferably selected from the group consisting of a hydrogen atom, t-butyldimethylsilyl, trimethylsilyl, and triethylsilyl, more preferably selected from the group consisting of a hydrogen atom and t-butyldimethylsilyl.

The protective group of carboxyl which may be represented by $R^2$ or R is not particularly limited and may be any protective group so far as it is well known to a person having ordinary skill in the art as a protective group of carboxyl. Preferably, the protective group of carboxyl is easily removable. Such protective groups of carboxyl include, for example, aralkyl such as 4-nitrobenzyl (pNB), 4-methoxybenzyl, and diphenylmethyl; alkenyl such as allyl; and silyl such as t-butyldimethylsilyl. Preferably, the protective group of carboxyl represented by $R^2$ or R is allyl, 4-nitrobenzyl, 4-methoxybenzyl, or diphenylmethyl, more preferably allyl or 4-nitrobenzyl.

$R^2$ or R may represent an anion in a carboxylate anion (—COO⁻). In this case, the carboxylate anion may be in the form of a salt. The salt is a pharmaceutically acceptable salt. Such pharmaceutically acceptable salts include inorganic salts such as salts with metals such as lithium, sodium, potassium, calcium, or magnesium, ammonium salts, or salts with organic bases such as triethylamine or diisopropylethylamine.

$R^2$ or R is preferably selected from the group consisting of a hydrogen atom, an anion in a carboxylate anion, 4-nitrobenzyl, 4-methoxybenzyl, diphenylmethyl, allyl, and t-butyldimethylsilyl, more preferably selected from the group consisting of allyl, 4-nitrobenzyl, and 4-methoxybenzyl.

In one preferred embodiment of the present invention, R represents a hydrogen atom, an anion in a carboxylate anion, or a protective group of carboxyl, and $R^2$ represents an easily removable protective group of carboxyl.

When Y represents group $P(R^3)_3$, the "C1-6 alkyl optionally substituted by a halogen atom" which may be represented by $R^3$ may be, for example, chlorinated alkyl, and specific examples thereof include methyl, ethyl, propyl, n-butyl, t-butyl, chloromethyl, and dichloroethyl. Preferred are propyl, n-butyl, and t-butyl.

The "aryl optionally substituted by a halogen atom or C1-6 alkyl, optionally substituted by a halogen atom" which may be represented by $R^3$ may be, for example, aryl optionally substituted by a halogen atom or unsubstituted C1-6 alkyl. Preferably, $R^3$ is 4-fluorophenyl, o-methylphenyl, m-methylphenyl, p-methylphenyl, or unsubstituted phenyl, more preferably unsubstituted phenyl.

Y preferably represents an oxygen atom or group $P(C_6H_5)_3$.

The protective group of carbonyl which can be formed by combining $Z^1$ and $Z^2$ together is not particularly limited and may be any protective group of carbonyl so far as it is well known to a person having ordinary skill in the art. Preferably, the protective group of carbonyl is easily removable. Such protective groups of carbonyl include, for example, dialkoxy such as dimethoxy or diethoxy; alkylenedioxy such as ethylenedioxy or trimethylenedioxy; alkylenedithio such as ethylenedithio or trimethylenedithio; hydrazone such as dimethylhydrazone or phenylhydrazone; and oxime, O-methyloxime, O-benzyloxime, and methylene. Preferably, the protective group of carbonyl is dialkoxy such as dimethoxy or diethoxy, or hydrazone such as dimethylhydrazone.

When one of $Z^1$ and $Z^2$ represents a hydrogen atom, the protective group of protected hydroxyl which may be represented by the other group is not particularly limited and may be any protective group of hydroxyl so far as it is well known as the protective group to a person having ordinary skill in the art. Such protective groups of hydroxyl include, for example, silyl such as t-butyldimethylsilyl, trimethylsilyl, or triethylsilyl; oxycarbonyl such as 4-nitrobenzyloxycarbonyl, 4-methoxybenzyloxycarbonyl, or allyloxycarbonyl; and aralkyl such as benzyl or 4-methoxybenzyl. Preferably, the protected hydroxyl which may be represented by $R^1$ or $R^{11}$ is hydroxyl protected by silyl such as t-butyldimethylsilyl, trimethylsilyl, or triethylsilyl, more preferably hydroxyl protected by trimethylsilyl or triethylsilyl.

Preferably, $Z^1$ and $Z^2$ together represent a group selected from the group consisting of an oxygen atom, dimethoxy, diethoxy, and dimethylhydrazone. Alternatively, one of $Z^1$ and $Z^2$ represents a hydrogen atom, and the other represents hydroxyl, or represents hydroxyl protected by a group selected from the group consisting of t-butyldimethylsilyl, trimethylsilyl, and triethylsilyl.

More preferably, $Z^1$ and $Z^2$ together form an oxygen atom, dimethoxy, diethoxy, or dimethylhydrazone, or alternatively one of $Z^1$ and $Z^2$ represents a hydrogen atom and the other represents hydroxyl protected by triethylsilyl.

In the "optionally substituted C1-6 alkyl" which may be represented by $R^4$, for example, a halogen atom such as a chlorine atom or a bromine atom may be mentioned as the substituent. Accordingly, the "optionally substituted C1-6 alkyl" which may be represented by $R^4$ is preferably "C1-6 alkyl optionally substituted by a halogen atom." Specific examples thereof include methyl, ethyl, propyl, n-butyl, t-butyl, 2-chloro-1,1-dimethylethyl, 2-chloroethyl, and 1-bromoisobutyl. The "optionally substituted C1-6 alkyl" is more preferably t-butyl and 2-chloro-1,1-dimethylethyl.

In the "aryl optionally substituted by a group selected from the group consisting of a halogen atom, optionally substituted C1-6 alkyl, optionally substituted C1-6 alkoxy, and —$NR^5R^6$" which may be represented by $R^4$, the aryl group is preferably phenyl.

$R^5$ and $R^6$, which may be the same or different, represent C1-6 alkyl, or alternatively $R^5$ and $R^6$ together represent —$(CH_2)_n$— wherein n is an integer of 2 to 6, preferably an integer of 4 to 6.

"Optionally substituted C1-6 alkyl" as a substituent for "aryl" which may be represented by $R^4$ is preferably "a halogen atom, C1-6 alkyl, or C1-6 alkyl optionally substituted by C1-6 alkoxy." The "optionally substituted C1-6 alkoxy" as the substituent is preferably "a halogen atom, C1-6 alkyl, or C1-6 alkoxy optionally substituted by C1-6 alkoxy."

In aryl which may be represented by $R^4$, when one or more hydrogen atoms thereof are substituted by a substituent, specific examples of the substituent include halogen atoms such as chlorine, bromine, and fluorine atoms; straight chain alkyl such as methyl, ethyl, and n-propyl; branched chain alkyl such as isopropyl and t-butyl; straight chain alkoxy such as methoxy, ethoxy, and isopropyloxy; N,N-di(C1-6 alkyl) amino such as N,N-dimethylamino and N,N-diethylamino; and three- to seven-membered cyclic alkylamino such as 1-pyrrolidinyl and 1-piperidinyl. Preferred substituents include C1-6 alkoxy and N,N-di(C1-6 alkyl)amino or three- to seven-membered cyclic alkylamino.

Aryl which may be represented by $R^4$ is preferably unsubstituted phenyl, 2-chlorophenyl, 2-methylphenyl, 3,4-dimethylphenyl, 2-methoxyphenyl, 4-methoxyphenyl, 2-ethoxyphenyl, 4-isopropyloxyphenyl, 4-(N,N-dimethylamino)phenyl, or 4-(N,N-diethylamino)phenyl. More preferably, aryl which may be represented by $R^4$ is 4-methoxyphenyl, 4-isopropyloxyphenyl, 4-(N,N-dimethylamino)phenyl or 4-(N,N-diethylamino)phenyl.

The protective group of amino which may be represented by $R^7$ and $R^8$ is not particularly limited and may be any protective group of amino so far as the protective group is well known to a person having ordinary skill in the art. Protective groups of amino usable herein include, for example, acyl such as formyl, alkylcarbonyl (such as acetyl), and arylcarbonyl (such as benzoyl); aralkyl such as benzyl; oxycarbonyl such as alkylcarbonyl (such as t-butoxycarbonyl), and arylcarbonyl (such as benzyloxycarbonyl); sulfonyl such as alkylsulfonyl (such as methanesulfonyl), and arylsulfonyl (such as benzenesulfonyl); and silyl such as trialkylsilyl (such as trimethylsilyl, triethylsilyl, or t-butyl dimethylsilyl). Preferred are formyl, t-butoxycarbonyl, trimethylsilyl, triethylsilyl and the like.

Examples of the leaving group represented by $L^1$ include acyloxy such as alkylcarbonyloxy (such as acetoxy) or arylcarbonyloxy (such as benzoyloxy); arylsulfonyloxy such as benzenesulfonyloxy; alkylsulfonyl such as methanesulfonyl; alkanoylthio such as acetylthio; alkylthio such as methylthio; alkylsulfinyl such as methylsulfinyl; arylsulfinyl such as benzenesulfinyl; alkylsulfonyl such as methanesulfonyl; arylsulfonyl such as benzenesulfonyl; and halogen atoms such as chlorine, bromine, and iodine atoms. The leaving group represented by $L^1$ is preferably methylthio, acetylthio, a chlorine atom, or acetoxy, more preferably acetoxy.

Examples of the leaving group represented by $L^2$ include halogen atoms such as chlorine, bromine, and iodine atoms; alkylsulfonyloxy such as methanesulfonyloxy; and arylsulfonyloxy such as benzenesulfonyloxy. Preferably, the leaving group represented by $L^2$ is methanesulfonyloxy or a chlorine atom, more preferably a chlorine atom or the like.

Examples of the leaving group represented by $L^3$ include halogen atoms such as chlorine, bromine, and iodine atoms; alkylsulfonyloxy optionally substituted by a halogen atom, such as methanesulfonyloxy, benzenesulfonyloxy, —$OSO_2CF_3$, or —$OSO_2PhCH_3$, and arylsulfonyloxy optionally substituted by alkyl. Preferably, the leaving group represented by $L^3$ is —$OSO_2CF_3$ or an iodine atom, more preferably an iodine atom.

X represents a halogen atom, for example, a chlorine, bromine, or iodine atom, preferably a bromine or iodine atom, more preferably a bromine atom.

M represents lithium, MgBr, or MgI, preferably MgBr.

In one preferred embodiment of the present invention, $R^1$ represents a hydrogen atom, or represents a protective group of hydroxyl, R represents a hydrogen atom, an anion in a carboxylate anion, or a protective group of carboxyl, $R^2$ represents a protective group of carboxyl, X represents a bromine or iodine atom, Y represents an oxygen atom or group $P(C_6H_5)_3$, and $Z^1$ and $Z^2$ together represent an oxygen atom or an easily removable protective group of carbonyl, or alternatively one of $Z^1$ and $Z^2$ represents a hydrogen atom and the other represents protected hydroxyl.

In one preferred embodiment of the present invention, in formula (1), $R^1$ represents a hydrogen atom, or represents a protective group of hydroxyl, $R^2$ represents a protective group of carboxyl, Y represents an oxygen atom or group $P(C_6H_5)_3$, $Z^1$ and $Z^2$ together represent an oxygen atom or a protective group of carbonyl, or alternatively one of $Z^1$ and $Z^2$ represents a hydrogen atom and the other represents protected hydroxyl.

In another preferred embodiment of the present invention, in formula (1), $R^1$ represents a hydrogen atom or a protective group of hydroxyl, $R^2$ represents an easily removable protective group of carboxyl, $Z^1$ and $Z^2$ together represent an oxygen atom or an easily removable protective group of carbonyl, or one of $Z^1$ and $Z^2$ represents a hydrogen atom and the other represents hydroxyl or protected hydroxyl, and Y represents an oxygen atom or group $P(R^3)_3$, wherein $R^3$s, which may be the same or different, represent C1-6 alkyl optionally substituted by a halogen atom, or aryl optionally substituted by a halogen atom or C1-6 alkyl in which the alkyl group may be substituted by a halogen atom.

Specific examples of compounds represented by formula (1) include:

(3S,4R)-1-allyloxyoxalyl-3-[(1R)-1-(tert-butyldimethylsilyloxy)ethyl]-4-[(1R)-1-methyl-2-[7-(pyridin-3-yl)carbonylimidazo[5,1-b]thiazol-2-yl]-2-oxoethyl]azetidin-2-one (compound of Example 23);

(3S,4R)-1-allyloxyoxalyl-3-[(1R)-1-hydroxyethyl)-4-[(1R)-1-methyl-2-[7-(pyridin-3-yl)carbonylimidazo[5,1-b]thiazol-2-yl]-2-oxoethyl]azetidin-2-one (compound of Example 25);

(3S,4R)-3-[(1R)-1-(t-butyldimethylsilyloxy)ethyl]-4-{(1R)-1-methyl-2-[7-(pyridin-3-yl)carbonylimidazo[5,1-b]thiazol-2-yl]-2-oxoethyl}-1-[4-nitrobenzyloxycarbonyl(triphenylphosphoranylidene)methyl]azetidin-2-one (compound of Example 27);

(3S,4R)-3-[(1R)-1-hydroxyethyl]-4-{(1R)-1-methyl-2-[7-(pyridin-3-yl)carbonylimidazo[5,1-b]thiazol-2-yl]-2-oxoethyl}-1-[4-nitrobenzyl-oxycarbonyl(triphenylphosphoranylidene)methyl]azetidin-2-one (compound of Example 29);

(3S,4R)-1-[allyloxycarbonyl(triphenylphosphoranylidene)methyl]-3-[(1R)-1-(t-butyldimethylsilyloxy)ethyl]-4-{(1R)-1-methyl-2-[7-(pyridin-3-yl)triethylsilyloxymethylimidazo[5,1-b]thiazol-2-yl]-2-oxoethyl}azetidin-2-one (compound of Example 31);

(3S,4R)-1-[allyloxycarbonyl(triphenylphosphoranylidene)methyl]-3-[(1R)-1-(t-butyldimethylsilyloxy)ethyl]-4-{(1R)-1-methyl-2-[7-dimethoxy-(pyridin-3-yl)methylimidazo[5,1-b]thiazol-2-yl]-2-oxoethyl}azetidin-2-one (compounds of Examples 32 to 35);

(3S,4R)-1-[allyloxycarbonyl(triphenylphosphoranylidene)methyl]-3-[(1R)-1-hydroxyethyl]-4-{(1R)-1-methyl-2-[7-(pyridin-3-yl)carbonyl-imidazo[5,1-b]thiazol-2-yl]-2-oxoethyl}azetidin-2-one (compounds of Example 36 etc.);

(3S,4R)-1-[allyloxycarbonyl(triphenylphosphoranylidene)methyl]-3-[(1R)-1-(t-butyldimethylsilyloxy)ethyl]-4-[(1R)-1-methyl-2-[7-diethoxy-(pyridin-3-yl)methylimidazo[5,1-b]thiazol-2-yl]-2-oxoethyl]azetidin-2-one (compound of Example 37);

(3S,4R)-1-[allyloxycarbonyl(triphenylphosphoranylidene)methyl]-3-[(1R)-1-(t-butyldimethylsilyloxy)ethyl]-4-[(1R)-1-methyl-2-[7-(pyridin-3-yl)dimethylhydrazonoylimidazo[5,1-b]thiazol-2-yl]-2-oxoethyl]azetidin-2-one (compound of Example 40); and (3S,4R)-3-[(1R)-1-(t-butyldimethylsilyloxy)ethyl]-4-{(1R)-1-methyl-2-[7-dimethoxy(pyridin-3-yl)methylimidazo[5,1-b]thiazol-2-yl]-2-oxoethyl]-1-[4-nitrobenzyloxycarbonyl (triphenylphosphoranylidene)methyl]azetidin-2-one (compound of Example 42).

Preferably, compounds represented by formula (1) include:

(3S,4R)-1-allyloxyoxalyl-3-[(1R)-1-(tert-butyldimethyl silyl-oxy)ethyl]-4-[(1R)-1-methyl-2-[7-(pyridin-3-yl) carbonylimidazo[5,1-b]thiazol-2-yl]-2-oxoethyl]azetidin-2-one (compound of Example 23);

(3S,4R)-1-allyloxyoxalyl-3-[(1R)-1-hydroxyethyl)-4-[(1R)-1-methyl-2-[7-(pyridin-3-yl)carbonylimidazo[5,1-b]thiazol-2-yl]-2-oxoethyl]azetidin-2-one (compound of Example 25);

(3S,4R)-1-[allyloxycarbonyl(triphenylphosphoranylidene)methyl]-3-[(1R)-1-(t-butyldimethylsilyloxy)ethyl]-4-{(1R)-1-methyl-2-[7-(pyridin-3-yl)triethylsilyloxymethylimidazo[5,1-b]thiazol-2-yl]-2-oxoethyl}azetidin-2-one (compound of Example 31);

(3S,4R)-1-[allyloxycarbonyl(triphenylphosphoranylidene)methyl]-3-[(1R)-1-(t-butyldimethylsilyloxy)ethyl]-4-{(1R)-1-methyl-2-[7-dimethoxy-(pyridin-3-yl)methylimidazo[5,1-b]thiazol-2-yl]-2-oxoethyl}azetidin-2-one (compounds of Examples 32 to 35);

(3S,4R)-1-[allyloxycarbonyl(triphenylphosphoranylidene)methyl]-3-[(1R)-1-hydroxyethyl]-4-{(1R)-1-methyl-2-[7-(pyridine-3-yl)carbonyl-imidazo[5,1-b]thiazol-2-yl]-2-oxoethyl}azetidin-2-one (compound of Example 36 etc.); and (3S,4R)-1-[allyloxycarbonyl(triphenylphosphoranylidene)methyl]-3-[(1R)-1-(t-butyldimethylsilyloxy)ethyl]-4-[(1R)-1-methyl-2-[7-diethoxy-(pyridin-3-yl)methylimidazo[5,1-b]thiazol-2-yl]-2-oxoethyl]azetidin-2-one (compound of Example 37).

More preferably, compounds represented by formula (1) include:

(3S,4R)-1-allyloxyoxalyl-3-[(1R)-1-(tert-butyldimethylsilyl-oxy)ethyl]-4-[(1R)-1-methyl-2-[7-(pyridin-3-yl) carbonylimidazo[5,1-b]thiazol-2-yl]-2-oxoethyl]azetidin-2-one (compound of Example 23);

(3S,4R)-1-allyloxyoxalyl-3-[(1R)-1-hydroxyethyl)-4-[(1R)-1-methyl-2-[7-(pyridin-3-yl)carbonylimidazo[5,1-b]thiazol-2-yl]-2-oxoethyl]-azetidin-2-one (compound of Example 25);

(3S,4R)-1-[allyloxycarbonyl(triphenylphosphoranylidene)methyl]-3-[(1R)-1-(t-butyldimethylsilyloxy)ethyl]-4-{(1R)-1-methyl-2-[7-dimethoxy-(pyridin-3-yl)methylimidazo[5,1-b]thiazol-2-yl]-2-oxoethyl}azetidin-2-one (compounds of Examples 32 to 35); and (3S,4R)-1-[allyloxycarbonyl(triphenylphosphoranylidene)methyl]-3-[(1R)-1-hydroxyethyl]-4-{(1R)-1-methyl-2-[7-(pyridine-3-yl)carbonyl-imidazo[5,1-b]thiazol-2-yl]-2-oxoethyl}azetidin-2-one (compound of Example 36 etc.).

Specific examples of preferred compounds represented by formula (3) include:

2-bromo-7-dimethoxy(pyridin-3-yl)methylimidazo[5,1-b]thiazole;

2-bromo-7-(pyridin-3-yl)triethylsilyloxymethylimidazo[5,1-b]thiazole;

2-bromo-7-diethoxy(pyridin-3-yl)methylimidazo[5,1-b]thiazole; and 2-bromo-7-(pyridin-3-yl)dimethylhydrazonoylimidazo[5,1-b]thiazole.

Specific examples of preferred compounds represented by formula (6) include:

2-propionyl-7-dimethoxy(pyridin-3-yl)methylimidazo[5,1-b]thiazole;

2-propionyl-7-(pyridin-3-yl)triethylsilyloxymethylimidazo[5,1-b]thiazole; and 2-propionyl-7-(pyridin-3-yl)dimethylhydrazonoylimidazo[5,1-b]thiazole.

Specific examples of preferred compounds represented by formula (8) include:

(3S,4R)-3-[(1R)-1-(tert-butyldimethylsilyloxy)ethyl]-4-[(1R)-1-methyl-2-[7-dimethoxy(pyridin-3-yl)methylimidazo[5,1-b]thiazol-2-yl]-2-oxoethyl]azetidin-2-one;

(3S,4R)-3-[(1R)-1-(tert-butyldimethylsilyloxy)ethyl]-4-[(1R)-1-methyl-2-[7-(pyridin-3-yl)triethylsilyloxymethylimidazo[5,1-b]thiazol-2-yl]-2-oxoethyl]azetidin-2-one;

(3S,4R)-3-[(1R)-1-(tert-butyldimethylsilyloxy)ethyl]-4-[(1R)-1-methyl-2-[7-(pyridin-3-yl)carbonylimidazo[5,1-b]thiazol-2-yl]-2-oxoethyl]azetidin-2-one;

(3S,4R)-3-[(1R)-1-hydroxyethyl]-4-[(1R)-1-methyl-2-[7-(pyridin-3-yl)carbonylimidazo[5,1-b]thiazol-2-yl]-2-oxoethyl]azetidin-2-one; and (3S,4R)-3-[(1R)-1-(triethylsilyloxy)ethyl]-4-[(1R)-1-methyl-2-[7-(pyridin-3-yl)carbonylimidazo[5,1-b]thiazol-2-yl]-2-oxoethyl]azetidin-2-one.

Scheme for Production of Compounds of Formula (1) and Compounds of Formula (A)

The process for the production of compounds of formula (1) according to the present invention and the process for the production of compounds of formula (A) are as shown in scheme B below.

Scheme B:

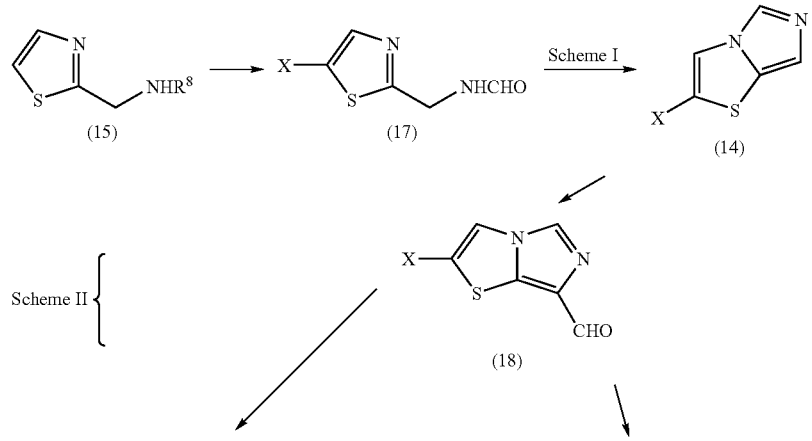

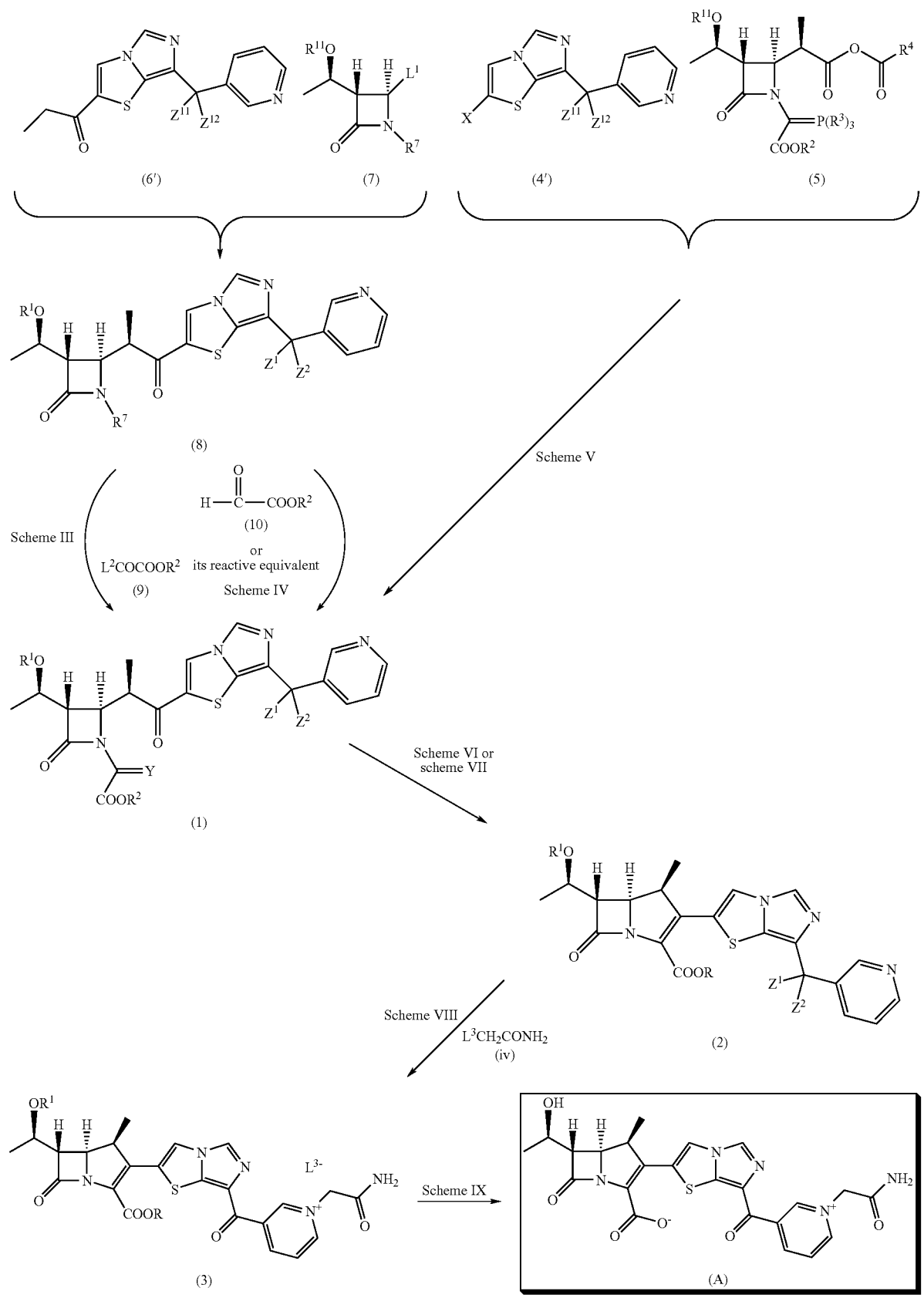

(I) Production of compounds of formula (14)

Compounds of formula (14) can be synthesized by the process shown in scheme I below.

Scheme I

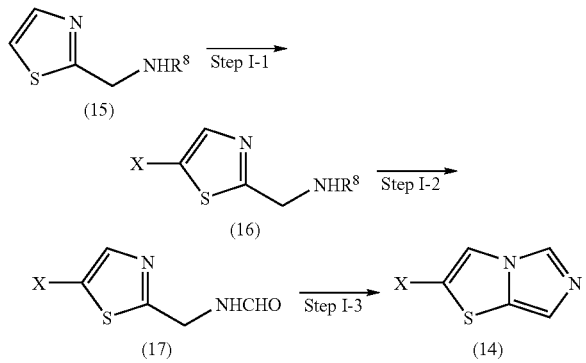

wherein $R^8$ represents a hydrogen atom or a protective group of amino; and X represents a halogen atom, preferably a bromine atom.

In the present invention, the compound of formula (14) can be produced by steps (a) and (b) below as shown in scheme I:

(a) the step of reacting the compound of formula (15) with a halogenating agent to give a compound of formula (16), optionally removing the protective group, and then formulating the amino group to give a compound of formula (17); and (b) the step of reacting the compound of formula (17) with a dehydrating agent for cyclization, to give a compound of formula (14).

Specifically, according to the process shown in scheme I, in step I-1, the compound of formula (16) is produced by reacting the compound of formula (15) with a halogenating agent. In step I-2, the compound of formula (17) is produced by, when $R^8$ represents a hydrogen atom or a protective group other than formyl, converting $R^8$ to formyl, or, if necessary, removing the protective group in the compound of formula (16), and then formylating the amino group. Subsequently, in step I-3, the compound of formula (14) is produced by reacting the compound of formula (17) with a hydrating agent for cyclization.

When X represents a bromine atom, formula (14) may be represented by formula (14a):

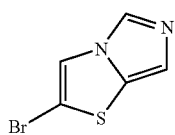

(14a)

(Step I-1)

The compound of formula (15) in step I-1 may be a commercially available product or alternatively may be synthesized by a conventional method. For example, the compound of formula (15) may be synthesized by the method described in Japanese Patent Laid-Open Publication No. 311071/1996.

In this step, the compound of formula (15) is halogenated. The compound of formula (16) may be produced by reacting the compound of formula (15) with a halogenating agent in a solvent inert to the reaction in the presence of a base and an additive.

The solvent used in step I-1 is not particularly limited and may be properly selected by a person having ordinary skill in the art so far as the solvent is inert to the reaction in this step. Specific examples of solvents include chloroform, methylene chloride, ethyl alcohol, methyl alcohol, tetrahydrofuran, dioxane, acetonitrile, and water. They may be used as a mixed solvent composed of two or more solvents. Preferably, the solvent may be a mixed solvent composed of tetrahydrofuran and water.

Usable bases include, for example, sodium hydrogencarbonate, sodium carbonate, sodium hydroxide, and sodium acetate. Preferably, the base is sodium hydroxide.

Additives include, for example, salts such as sodium chloride and sodium bromide; and buffering agents such as sodium dihydrogenphosphate, disodium hydrogen phosphate, acetic acid, and sodium acetate. Preferably, the additive is sodium bromide or sodium dihydrogenphosphate. The amount of the additive used is preferably 5 to 50 times by weight that of the compound of formula (15).

The halogenating agent may be conventional. Preferred are chlorinating agents, brominating agents, iodinating agents and the like. The halogenating agent is more preferably a brominating agent. Brominating agents include, for example, bromine and N-bromosuccinimide. More preferably, the halogenating agent is bromine. The amount of the halogenating agent used is preferably 5 to 10 molar equivalents relative to the compound of formula (15).

The reaction temperature may vary depending upon the solvent used or the like. In general, however, the reaction temperature is in a range of 0° C. to the reflux temperature of the solvent used. The reaction time may vary depending upon the solvent used, the reaction temperature and the like. In general, however, the reaction time is 10 min to 24 hr.

The resultant compound of formula (16) may be subjected to conventional post treatment. Here the conventional post treatment is well known to a person having ordinary skill in the art, and examples thereof include quenching (stopping of reaction) and extraction. Further, isolation and purification may be carried out by optionally applying conventional methods such as precipitation, crystallization, gel filtration, and column chromatography on silica gel.

(Step I-2)

In step I-2, the compound of formula (17) is produced by, when $R^8$ in the compound of formula (16) represents a hydrogen atom or a protective group other than formyl, converting $R^8$ to formyl, or optionally removing the protective group of the compound of formula (16), and then formylating the amino group.

The reaction for removing the protective group of amino may vary depending upon the type of the protective group. However, this reaction may be carried out by using as reference a reaction for removing the protective group of amino in conventional organic synthetic chemistry. For example, when the protective group of amino, $R^8$, in the compound of formula (16) is t-butoxycarbonyl, t-butoxycarbonyl as the protective group can be removed by reacting the compound of formula (16) in a solvent inert to the reaction (for example, methanol, ethanol, methylene chloride, chloroform, tetrahydrofuran, dioxane, toluene, hexane, or anisole) at a temperature in a range of −20° C. to the reflux temperature of the solvent used, using an acid such as hydrochloric acid, sulfuric acid, methanesulfonic acid, or trifluoroacetic acid and/or a Lewis acid such as aluminum trichloride, bromocatecholborane, or trimethylsilyl trifluoromethanesulfonate in an amount of 0.1 to 100 molar equivalents relative to the compound of formula (16) for 10 min to 24 hr.

The reaction for formylating the amino group may be carried out by using as reference a reaction for formylating the amino group in the conventional organic synthetic chemistry. For example, the amino group may be formylated, for example, by, when $R^8$ in the compound of formula (16) represents a hydrogen atom, using the compound of formula (16) as such, or reacting the compound of formula (16) for removing the protective group of amino, and then reacting the compound in a solvent inert to the reaction (for example, methylene chloride, chloroform, water, dimethylformamide, tetrahydrofuran, dioxane, toluene, or hexane) or without using any solvent at a temperature in a range of −20° C. to the reflux temperature of the solvent used, using a formic ester such as ethyl formate or n-propyl formate, a mixed acid anhydride such as formic acid acetic anhydride or formic acid pivalic acid anhydride, or an active ester such as 4-nitrophenyl formate, in an amount of 1 to 100 molar equivalents relative to the compound of formula (16) for 10 min to 24 hr.

The compound of formula (17) may be subjected to conventional post treatment. Further, isolation and purification may be carried out by optionally applying conventional methods such as precipitation, crystallization, gel filtration, and column chromatography on silica gel.

(Step I-3)

Step I-3 is a cyclization reaction of the compound of formula (17) which may be carried out, for example, by the method described in Japanese Patent Laid-Open Publication No. 311071/1996. In step I-3, the compound of formula (14) may be produced by reacting the compound of formula (17) with a dehydrating agent in a solvent inert to the reaction or in the absence of any solvent for cyclization.

The solvent used in step I-3 is not particularly limited and may be properly selected by a person having ordinary skill in the art, so far as the solvent is inert to the reaction. Specific examples thereof include benzene, toluene, xylene, methylene chloride, chloroform, and 1,2-dichloroethane. The solvent is preferably toluene.

Dehydrating agents include, for example, phosphorus oxychloride, phosphorus oxybromide, phosphorus pentachloride, polyphosphoric acid, sulfuric acid, thionyl chloride, trifluoroacetic anhydride, and trifluoromethanesulfonic anhydride. The dehydrating agent is preferably phosphorus oxychloride. The amount of the dehydrating agent used is preferably 1 to 100 molar equivalents relative to the compound of formula (17).

The reaction temperature may vary depending upon the solvent used or the like. In general, however, the reaction temperature is in a range of −20° C. to the reflux temperature of the solvent used. The reaction time may vary depending upon the solvent used, the temperature of the reaction and the like. In general, however, the reaction time is 10 min to 24 hr.

The compound of formula (14) may be subjected to conventional post treatment. Further, isolation and purification may be carried out by optionally applying conventional methods such as precipitation, crystallization, gel filtration, and column chromatography on silica gel.

(II) Production of Compounds of Formula (4) and Formula (6)

Compounds of formula (4) and formula (6) may be synthesized, for example, by the process shown in scheme II below.

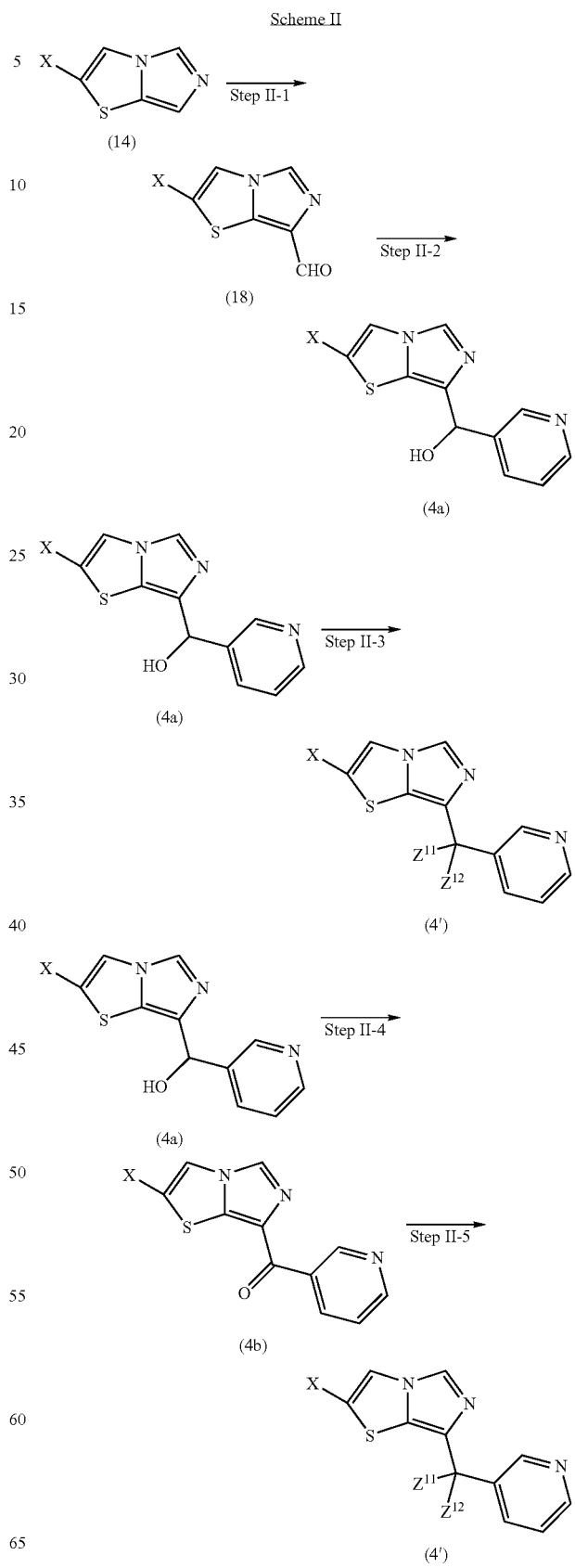

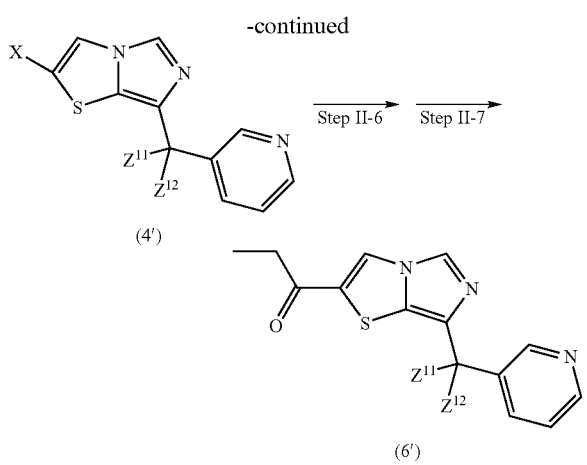

wherein X, $Z^{11}$ and $Z^{12}$ are as defined above.

In the present invention, as shown in scheme II, the compound of formula (4') may be produced by steps of (c) and (d) below:

(c) the step of formylating the compound of formula (14) using a Vilsmeyer complex to give the compound of formula (18).

(d) the step of reacting the compound of formula (18) with a 3-metallopyridine of formula (19) to give a compound (a compound of formula (4a)) of formula (4') in which one of $Z^{11}$ and $Z^{12}$ represents a hydrogen atom and the other represents hydroxyl, and protecting hydroxyl in this compound, or oxidizing hydroxyl in this compound and protecting the resultant carbonyl to give the compound of formula (4'):

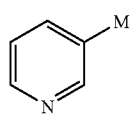

(19)

wherein M represents lithium, MgBr, or MgI.

When the compound of formula (6') is necessary, this compound can be produced by further carrying out step (e):

(e) the step of reacting a compound, obtained by treating the compound of formula (4') with a Grignard reagent, with a propionic acid derivative to give a compound of formula (6').

(Step II-1)

Step II-1 is a formylation reaction of the compound of formula (14) which may be carried out, for example, by the method described in Japanese Patent Laid-Open Publication No. 311071/1996. In step II-1, the compound of formula (18) may be produced by reacting the compound of formula (14) with separately prepared Vilsmeyer complex in a solvent inert to the reaction.

The solvent used in step II-1 is not particularly limited and may be properly selected by a person having ordinary skill in the art, so far as the solvent is inert to the reaction. Specific examples thereof include methylene chloride, chloroform, 1,2-dichloroethane, dimethylformamide, and nitrobenzene. The solvent is preferably methylene chloride.

The Vilsmeyer complex refers to a reactant used in a formylation reaction well known to a person having ordinary skill in the art, that is, a Vilsmeyer's reaction and may be properly selected by a person having ordinary skill in the art.

The Vilsmeyer complex may be a methyleneiminium compound prepared, for example, by reacting N,N-dimethylformamide, N-methylformanilide, N-formylmorpholine, or N,N-diisopropylformamide, with a halogenating reagent such as phosphorus oxychloride, phosgene, oxalyl chloride, or thionyl chloride. The amount of the Vilsmeyer complex used is preferably 1 to 10 molar equivalents relative to the compound of formula (14).

The reaction temperature may vary depending upon the solvent used or the like. In general, however, the reaction temperature is in a range of −20° C. to the reflux temperature of the solvent used. The reaction time may vary depending upon the solvent used, the reaction temperature and the like. In general, however, the reaction time is 10 min to 24 hr.

The compound of formula (18) thus obtained may be subjected to conventional post treatment. Further, isolation and purification may be carried out by optionally applying conventional methods such as precipitation, crystallization, gel filtration, and column chromatography on silica gel.

(Step II-2)

Step II-2 is the step of reacting the formyl group in the compound of formula (18) with a 3-metallopyridine of formula (19). Here a compound of formula (4a) may be produced by reacting the compound of formula (18) with a separately prepared 3-metallopyridine in a solvent inert to the reaction.

The solvent used in step II-2 is not particularly limited and may be properly selected by a person having ordinary skill in the art, so far as the solvent is inert to the reaction. Specific examples of solvents include ether, tetrahydrofuran, dioxane, toluene, and hexane. The solvent is preferably tetrahydrofuran.

The 3-metallopyridine may be prepared by a method well known to a person having ordinary skill in the art. For example, the 3-metallopyridine may be prepared by reacting 3-bromopyridine, 3-iodopyridine or the like with an organolithium compound, such as n-butyllithium or t-butyllithium, or a Grignard reagent such as ethylmagnesium bromide or methylmagnesium iodide, and metallic magnesium or the like, in a solvent such as ether, tetrahydrofuran, dioxane, toluene, or hexane at a temperature in a range of −100° C. to the reflux temperature of the solvent used for 10 min to 24 hr.

In step II-2, the amount of 3-metallopyridine used is preferably 1 to 2 molar equivalents relative to the compound of formula (18).

The reaction temperature may vary depending upon the solvent used or the like. In general, however, the reaction temperature is in a range of −100° C. to the reflux temperature of the solvent used. The reaction time may vary depending upon the solvent used, the reaction temperature and the like. In general, however, the reaction time is 10 min to 24 hr.

The compound of formula (4a) may be subjected to conventional post treatment. Further, isolation and purification may be carried out by optionally applying conventional methods such as precipitation, crystallization, gel filtration, and column chromatography on silica gel.

(Step II-3)

Step II-3 is the step of protecting hydroxyl in the compound of formula (4a) to give the compound of formula (4) wherein one of $Z^1$ and $Z^2$ represents a hydrogen atom and the other represents protected hydroxyl (compound of formula (4')).

The protective group of hydroxyl usable in step II-3 is not particularly limited, and examples thereof include trialkylsilyl such as t-butyldimethylsilyl, trimethylsilyl, or triethylsilyl; oxycarbonyl such as 4-nitrobenzyloxycarbonyl, 4-methoxybenzyloxycarbonyl, or allyloxycarbonyl; and aralkyl such as benzyl and 4-methoxybenzyl. The protective group is preferably triethylsilyl.

This reaction for protecting hydroxyl may vary depending upon the type of the protective group. However, this reaction may be carried out by using as reference a reaction for protecting hydroxyl in a conventional organic synthetic reaction. For example, when the protective group is triethylsilyl, the compound of formula (4') may be produced by reacting the compound of formula (4a) using a triethylsilylating agent (for example, triethylsilylchloride, or triethylsilyl trifluoromethanesulfonate) in an amount of 1 to 10 molar equivalents relative to the compound of formula (4a) in a solvent inert to the reaction (for example, methylene chloride, chloroform, tetrahydrofuran, or dimethylformamide) at a temperature in a range of −20° C. to the reflux temperature of the solvent used in the presence of a base (for example, triethylamine, diisopropylethylamine, or imidazole) for 10 min to 24 hr.

The compound of formula (4'), (compound of formula (4) in which one of $Z^1$ and $Z^2$ represents a hydrogen atom and the other represents protected hydroxyl) thus obtained may be subjected to conventional post treatment. Further, isolation and purification may be carried out by optionally applying conventional methods such as precipitation, crystallization, gel filtration, and column chromatography on silica gel.

(Step II-4)

Step II-4 is a reaction for oxidizing hydroxyl in the compound of formula (4a) to give a compound of formula (4b) (compound of formula (4) wherein $Z^1$ and $Z^2$ together represent an oxygen atom).

In step II-4, the oxidation reaction of hydroxyl may be any oxidation reaction and may be properly carried out by a person having ordinary skill in the art by using as reference the oxidation reaction of hydroxyl in the conventional organic synthetic chemistry, so far as the reaction is inert to the atoms, other than hydroxyl, and any functional group. For example, when the oxidation reaction is carried out using manganese dioxide, the compound of formula (4b) may be produced by reacting the compound of formula (4a) with manganese dioxide in an amount of 1 to 10 times by weight that of the compound of formula (4a) in a solvent inert to the reaction (for example, methylene chloride, chloroform, methanol, ethanol, ethyl acetate, or tetrahydrofuran) at a temperature in a range of −20° C. to the reflux temperature of the solvent used for 10 min to 24 hr.

The compound of formula (4b) thus obtained may be subjected to conventional post treatment. Further, isolation and purification may be carried out by optionally applying conventional methods such as precipitation, crystallization, gel filtration, and column chromatography on silica gel.

(Step II-5)

Step II-5 is the step of protecting carbonyl in the compound of formula (4b) to give the compound of formula (4) wherein $Z^1$ and $Z^2$ together represent a protective group of carbonyl (compound of formula (4')).

The protective group of carbonyl usable in step II-5 is not particularly limited, and examples thereof include dialkoxy such as dimethoxy or diethoxy; alkylenedioxy such as ethylenedioxy or trimethylenedioxy; alkylenedithio such as ethylenedithio or trimethylenedithio; hydrazone such as dimethylhydrazone or phenylhydrazone; and oxime, O-methyloxime, O-benzyloxime, or methylene. The protective group of carbonyl is preferably dialkoxy such as dimethoxy or diethoxy; or hydrazone such as dimethylhydrazone, more preferably dimethoxy.

This reaction for protecting carbonyl may vary depending upon the type of the protective group. The reaction, however, may be carried out by using as reference a reaction for protecting carbonyl in the conventional organic synthetic reaction. For example, when the protective group of carbonyl is dimethoxy, the compound of formula (4') may be produced by treating the compound of formula (4b) with an acid such as sulfuric acid or tosylic acid in an amount of 1 to 30 molar equivalents relative to the compound of formula (4b) in the presence of trimethyl orthoformate in an amount of 1 to 100 molar equivalents relative to the compound of formula (4b) in methanol at a temperature in a range of −20° C. to the reflux temperature for 10 min to 24 hr.

The compound of formula (4') (compound of formula (4) wherein $Z^1$ and $Z^2$ together represent a protective group of carbonyl) may be subjected to conventional post treatment. Further, isolation and purification may be carried out by optionally applying conventional methods such as precipitation, crystallization, gel filtration, and column chromatography on silica gel.

The compound of formula (4), wherein $Z^1$ and $Z^2$ together represent an oxygen atom or a protective group of carbonyl, or alternatively one of $Z^1$ and $Z^2$ represents a hydrogen atom with the other representing hydroxyl or protected hydroxyl and X represents a halogen atom, may be properly produced by utilizing steps II-1 to II-5.

(Steps II-6 and II-7)

Step II-6 is the step of treating the compound of formula (4') with a Grignard reagent in a solvent inert to the reaction. Step II-7 is the step of reacting the compound prepared in step II-6 with a propionic acid derivative to give a compound of formula (6').

The solvent used in step II-6 is not particularly limited and may be properly selected by a person having ordinary skill in the art, so far as the solvent is inert to the reaction. Specific examples of solvents usable herein include methylene chloride, ether, tetrahydrofuran, dioxane, benzene, and toluene. The solvent is preferably tetrahydrofuran.

The Grignard reagent used is not particularly limited and may be properly selected by a person having ordinary skill in the art. Specific examples of the Grignard reagent include alkylmagnesium chlorides, alkylmagnesium bromides, alkylmagnesium iodides, and arylmagnesium bromides. The Grignard reagent is preferably an alkylmagnesium bromide. The amount of the Grignard reagent used is preferably 1 to 2 molar equivalents relative to the compound of formula (4').

The reaction temperature may vary depending upon the solvent used or the like. In general, however, the reaction temperature is in a range of −100° C. to the reflux temperature of the solvent used. The reaction time may vary depending upon the solvent used, the reaction temperature and the like. In general, however, the reaction time is 10 min to 24 hr.

The reaction mixture as such may be used in step II-7.

The propionic acid derivative usable in step II-7 is, for example, selected from the group consisting of N-methyl-N-methoxypropionamide, propionic acid anhydride, propionyl chloride, and propionic acid (pyridin-2-ylthio)ester. The propionic acid derivative is preferably N-methyl-N-methoxypropionamide. The amount of the propionic acid derivative used is preferably 1 to 3 molar equivalents relative to the compound of formula (4').

In one preferred embodiment of the present invention, the Grignard reagent is selected from the group consisting of alkylmagnesium chlorides, alkylmagnesium bromides, alkylmagnesium iodides, and arylmagnesium bromides, and the propionic acid derivative is selected from the group consisting of N-methyl-N-methoxypropionamide, propionic anhydride, propionyl chloride, and propionic acid (pyridin-2-ylthio)ester.

The reaction temperature may vary depending upon the solvent used or the like. In general, however, the reaction temperature is in a range of −100° C. to the reflux temperature of the solvent used. The reaction time may vary depending upon the solvent used, the reaction temperature and the like. In general, however, the reaction time is 10 min to 24 hr.

The compound of formula (6') may be subjected to conventional post treatment. Further, isolation and purification may be carried out by optionally applying conventional methods such as precipitation, crystallization, gel filtration, and column chromatography on silica gel.

The compound of formula (6), wherein $Z^1$ and $Z^2$ together represent an oxygen atom or a protective group of carbonyl, or alternatively one of $Z^1$ and $Z^2$ represents a hydrogen atom and the other represents hydroxyl or protected hydroxyl, may be properly produced by utilizing steps II-6 and II-7 and conventional methods.

(III) Production of Compounds of Formula (1) wherein Y Represents an Oxygen Atom Compounds of formula (1) wherein Y represents an oxygen atom can be synthesized, for example, by the process shown in scheme III below.

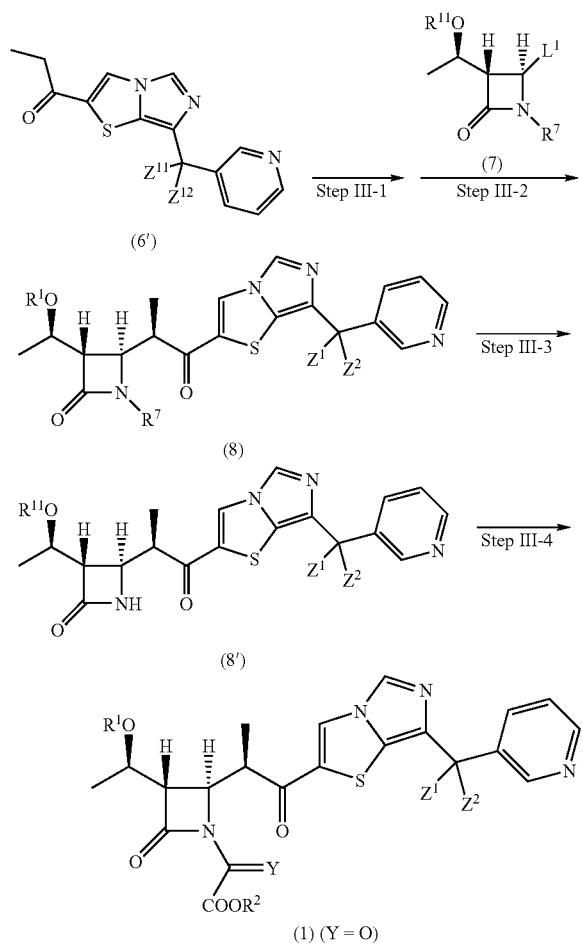

wherein $R^1$, $R^{11}$, $Z^1$, $Z^2$, $Z^{11}$, $Z^{12}$, $R^7$, and $L^1$ are as defined above.

In the present invention, the compound of formula (1) may be produced by steps (f) and (g) below as shown in scheme III:

(f) the step of reacting a compound, prepared by treating the compound of formula (6') with an alkali metal base, or a base and a metal(I) to (IV) compound, with a compound of formula (7), optionally removing a protective group and/or introducing a protective group and/or conducting oxidization, to give a compound of formula (8); and (g) the step of reacting the compound of formula (8) with a compound of formula (9) in the presence of a base:

$$L^2COCOOR^2 \qquad (9)$$

wherein $R^2$ represents a protective group of carboxyl; and $L^2$ represents a leaving group.

Specifically, according to the process shown in scheme III, in step III-1, the compound of formula (6') is converted to a metal enolate by treating the compound of formula (6') in a solvent inert to the reaction optionally in the presence of an additive with an alkali metal base or a base and a metal(I) to (IV) compound. Subsequently, in step III-2, the compound of formula (8) is produced by reacting this compound with the compound of formula (7). If necessary, in step III-3, the step of removing the protective group and/or the step of conducting oxidization and/or the step of introducing the protective group are carried out. Thereafter, in step III-4, the compound of formula (1) wherein Y represents an oxygen atom is produced by reacting the compound of formula (8) or formula (8') with the compound of formula (9).

(Step III-1)

In step III-1, a method in which the compound of formula (6') is treated with an alkali metal base to give a corresponding metal enolate (hereinafter often referred to as "method A"), or a method in which the compound of formula (6') is treated with a base and a metal (I) to (IV) compound to give a corresponding metal enolate (hereinafter often referred to as "method B").

Method A: The solvent used in method A is not particularly limited and may be properly selected by a person having ordinary skill in the art, so far as the solvent is inert to the reaction. Specific examples of solvents include ether, tetrahydrofuran, dioxane, dimethoxyethane, toluene, and hexane. The solvent is preferably tetrahydrofuran.

Preferred additives usable herein include lithium salts such as lithium chloride, lithium bromide, and lithium acetate. The amount of the additive used is preferably 1 to 10 molar equivalents relative to the compound of formula (6').

The alkali metal base used may be any alkali metal base so far as it is a base having an alkali metal and has basicity high enough to abstract a hydrogen atom from α-position of carbonyl in the compound of formula (6') to form the enolate. Specific examples of alkali metal bases include alkali metal amides such as lithium diisopropylamide, lithium isopropylcyclohexylamide, lithium dicyclohexylamide, lithium bistrimethylsilylamide, sodium bistrimethylsilylamide, potassium bistrimethylsilylamide, bromomagnesium diisopropylamide, iodomagnesium diisopropylamide, bromomagnesium bistrimethylsilylamide, iodomagnesium bistrimethylsilylamide, lithium-N-isopropyl-N-phenylamide, and lithium-N-isopropyl-N-naphthylamide; alkali metal hydrides such as sodium hydride and potassium hydride; alkali metal alkoxides such as potassium-t-butoxide and sodium-t-butoxide; and organolithium compounds such as n-butyllithium, methyllithium and phenyllithium. They may be used in combination of two or more. The alkali metal base is preferably lithium bistrimethylsilylamide. The amount of the alkali metal base used is preferably 1 to 3 molar equivalents relative to the compound of formula (6').

The reaction temperature may vary depending upon the solvent used or the like. In general, however, the reaction temperature is in a range of −100° C. to the reflux temperature of the solvent used. The reaction time may vary depending upon the solvent used, the reaction temperature and the like. In general, however, the reaction time is 10 min to 24 hr.

Method B: The solvent used in method B is not particularly limited and may be properly selected by a person having ordinary skill in the art, so far as the solvent is inert to the reaction. Specific examples of solvents include ether, tetrahydrofuran, dioxane, dimethoxyethane, toluene, hexane, methylene chloride, acetonitrile, and dimethylformamide. The solvent is preferably methylene chloride.

Bases usable herein include, for example, inorganic bases such as sodium carbonate, potassium carbonate, calcium carbonate, and sodium hydrogencarbonate; tertiary amines such as triethylamine, diisopropylethylamine, tri-n-butylamine, N-ethylpiperidine, and N-methylmorpholine; aromatic amines such as pyridine, 2,6-lutidine, and N,N-dimethylaminopyridine; alkali metal amides such as lithium diisopropylamide, lithium isopropylcyclohexylamide, lithium dicyclohexylamide, lithium bistrimethylsilylamide, sodium bistrimethylsilylamide, potassium bistrimethylsilylamide, bromomagnesium diisopropylamide, iodomagnesium diisopropylamide, bromomagnesium bistrimethylsilylamide, iodomagnesium bistrimethylsilylamide, lithium-N-isopropyl-N-phenylamide, and lithium-N-isopropyl-N-naphthylamide; and alkali metal alkoxides such as potassium-t-butoxide and sodium-t-butoxide. The base is preferably triethylamine, N-ethylpiperidine, pyridine, or 2,6-lutidine. The amount of the base used is preferably 1 to 5 molar equivalents relative to the compound of formula (6').

Metal(I) to (IV) compounds usable herein include, for example, titanium tetrachloride, trichloroisopropoxy titanium, dichlorodiisopropoxy titanium, chlorotriisopropoxy titanium, titanium tetraisopropoxide, dichlorodicyclopentadienyl titanium, zirconium tetrachloride, dichlorodicyclopentadienyl zirconium, tin(II) trifluoromethanesulfonate, silver trifluoromethanesulfonate, copper(II) trifluoromethanesulfonate, zinc(II) trifluoromethanesulfonate, zinc chloride, zinc bromide, zinc iodide, magnesium chloride, magnesium bromide, tin(II) chloride, chlorotrimethylsilane, trimethylsilyl trifluoromethanesulfonate, tert-butyldimethylsilyl trifluoromethanesulfonate, di-n-butylboron trifluoromethanesulfonate, boron trichloride, boron triisopropoxide, and ethylene chloroboronate. The metal (I) to (IV) compound is preferably tin (II) trifluoromethanesulfonate. The amount of the metal (I) to (IV) compound used is preferably 1 to 5 molar equivalents relative to the compound of formula (6').

The reaction temperature may vary depending upon the solvent used or the like. In general, however, the reaction temperature is in a range of −100° C. to the reflux temperature of the solvent used. The reaction time may vary depending upon the solvent used, the reaction temperature and the like. In general, however, the reaction time is 10 min to 24 hr.

The reaction mixture thus obtained as such may be used in step III-2.

(Step III-2)

Step III-2 is the step of reacting the reaction mixture prepared in step III-1 with the compound of formula (7) to give the compound of formula (8).

The compound of formula (7) used is a compound well known to a person having ordinary skill in the art and may be a commercially available compound, or alternatively may be properly synthesized by a conventional method known to a person having ordinary skill in the art. The compound of formula (7) is preferably (3S,4R)-4-acetoxy-3-[(1R)-1-tert-butyldimethylsilyloxyethyl]azetidin-2-one (a compound of formula (20) below) because this compound is produced on a commercial scale, and, thus, a large amount thereof is available.

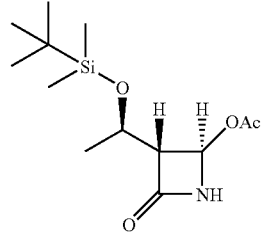

(20)

wherein Ac represents acetyl.

The reaction temperature may vary depending upon the solvent used or the like. In general, however, the reaction temperature is in a range of −100° C. to the reflux temperature of the solvent used. The reaction time may vary depending upon the solvent used, the reaction temperature and the like. In general, however, the reaction time is 10 min to 24 hr.

The compound of formula (8) thus obtained may be subjected to conventional post treatment. Further, isolation and purification may be carried out by optionally applying conventional methods such as precipitation, crystallization, gel filtration, and column chromatography on silica gel.

(Step III-3)

Step III-3 may be an optional step. The compound of formula (8) prepared in step III-2 may be if necessary subjected to the step of removing a protective group and/or the step of introducing a protective group and/or the step of conducting oxidation.

For example, when $Z^1$ and $Z^2$ in formula (8) together represent the protective group of carbonyl, this compound can be converted to the compound of formula (8') wherein $Z^{11}$ and $Z^{12}$ together represent an oxygen atom by removing the protective group in the compound of formula (8). The reaction for removing the protective group may vary depending upon the type of the protective group. The reaction, however, may be carried out by using as reference a reaction for removing a protective group of carbonyl in the conventional organic synthetic chemistry. For example, when $Z^1$ and $Z^2$ represent methoxy, dimethoxy as the protective group may be removed by reacting the compound of formula (8) with an acid, such as hydrochloric acid, sulfuric acid, methanesulfonic acid, or trifluoroacetic acid, in an amount of 0.1 to 100 molar equivalents relative to the compound of formula (8), in a solvent inert to the reaction, for example, methanol, ethanol, water, tetrahydrofuran, dioxane, dimethylformamide, methylene chloride, chloroform, acetone, or acetonitrile, at a temperature in a range of −20° C. to the reflux temperature of the solvent used for 10 min to 24 hr. In this case, the protective group of hydroxyl in $R^1$ may be simultaneously removed to bring $R^1$ to a hydrogen atom.

When one of $Z^1$ and $Z^2$ in formula (8) represents a hydrogen atom with the other representing protected hydroxyl, this compound can be converted to a compound of formula (8'), wherein one of $Z^{11}$ and $Z^{12}$ represents a hydrogen atom with the other representing hydroxyl, by removing the protective group of hydroxyl. The reaction for removing the protective group of hydroxyl may vary depending upon the type of the protective group. However, the reaction may be carried out by using as reference a reaction for removing a protective group of hydroxyl in the conventional organic synthetic chemistry. For example, when the protective group of hydroxyl is triethylsilyl, triethylsilyl as the protective group may be removed by reacting the compound of formula (8) using an acid, such as hydrochloric acid, sulfuric acid, methanesulfonic acid, or trifluoroacetic acid, or a fluorine reagent such as tetrabutylammonium fluoride, in an amount of 0.1 to 100 molar equivalents relative to the compound of formula (8) in a solvent inert to the reaction, for example, methanol, ethanol, water, tetrahydrofuran, dioxane, dimethylformamide, methylene chloride, chloroform, acetone, or acetonitrile, at a temperature in a range of −20° C. to the reflux temperature of the solvent used for 10 min to 24 hr. Here the protective group of hydroxyl in $R^1$ may be simultaneously removed to bring $R^1$ to a hydrogen atom.

When $Z^1$ and $Z^2$ in formula (8) are not such that they together represent an oxygen atom, this compound can be converted to the compound of formula (8'), wherein $Z^{11}$ and $Z^{12}$ together represent an oxygen atom, by oxidizing the compound of formula (8). The oxidization reaction may be carried out by using as reference an oxidization reaction in the conventional organic synthetic chemistry. For example, when manganese dioxide is utilized in the oxidization reaction, the compound of formula (8'), wherein $Z^{11}$ and $Z^{12}$ together represent carbonyl, can be produced by reacting the compound of formula (8) with manganese dioxide in an amount of 1 to 10 times by weight that of the compound of formula (8), in a solvent inert to the reaction, for example, methylene chloride, chloroform, methanol, ethanol, ethyl acetate, or tetrahydrofuran, at a temperature in a range of −20° C. to the reflux temperature of the solvent used for 10 min to 24 hr.

When $R^1$ in the compound of formula (8) represents a hydrogen atom, the hydroxyl group may be protected. Although the reaction for protecting hydroxyl may vary depending upon the type of the protective group, the reaction may be carried out by using as reference a reaction for protecting hydroxyl in the conventional organic synthetic chemistry. For example, when the desired protective group is triethylsilyl, the compound of formula (8') wherein $R^1$ represents protected hydroxyl can be produced by reacting the compound of formula (8), wherein $R^1$ represents a hydrogen atom, with a triethylsilylating agent, for example, triethylsilylchloride or triethylsilyl trifluoromethanesulfonate, in an amount of 1 to 10 molar equivalents relative to the compound of formula (8) in a solvent inert to the reaction, for example, methylene chloride, chloroform, tetrahydrofuran, or dimethylformamide, at a temperature in a range of −20° C. to the reflux temperature of the solvent used in the presence of a base such as triethylamine, diisopropylethylamine, or imidazole for 10 min to 24 hr.

When $R^7$ in the compound of formula (8) represents a protective group of amino, this compound can be converted to the compound of formula (8), wherein $R^7$ represents a hydrogen atom, by removing the protective group. The reaction for removing the protective group of amino may vary depending upon the type of the protective group. The reaction, however, may be carried out by using as reference a reaction for removing the protective group of amino in the conventional organic synthetic chemistry. For example, when the protective group of amino is triethylsilyl, the protective group may be removed by reacting the compound of formula (8) with an acid such as hydrochloric acid, sulfuric acid, methanesulfonic acid, or trifluoroacetic acid, or a fluorine reagent such as tetrabutylammonium fluoride, in an amount of 0.1 to 100 molar equivalents relative to the compound of formula (8) in a solvent inert to the reaction, for example, methanol, ethanol, water, tetrahydrofuran, dioxane, dimethyl, formamide, methylene chloride, chloroform, acetone, or acetonitrile, at a temperature in a range of −20° C. to the reflux temperature of the solvent used for 10 min to 24 hr.

The compound of formula (8') wherein $R^1$ represents protected hydroxyl thus obtained may be subjected to conventional post treatment. Further, isolation and purification may be carried out by optionally applying conventional methods such as precipitation, crystallization, gel filtration, and column chromatography on silica gel.

In $Z^1$ and $Z^2$ in formula (8), all forms included in this formula are mutually convertible by step III-3. Likewise, in the substituents of $R^1$ and $R^7$, all forms included in this formula are mutually convertible. Accordingly, if necessary, the compound of formula (8) may be converted to the compound of formula (8'). Likewise, if necessary, the compound of formula (8') may also be converted to the compound of formula (8).

(Step III-4)

Step III-4 is the step of reacting the compound of formula (8) or formula (8') with the compound of formula (9) in the presence of a base to give the compound of formula (1) wherein Y represents an oxygen atom.

The solvent used in step III-4 is not particularly limited and may be properly synthesized by a person having ordinary skill in the art, so far as the solvent is inert to this reaction. Specific examples of solvents include methylene chloride, chloroform, ether, tetrahydrofuran, toluene, acetonitrile, and dimethylformamide. The solvent is preferably methylene chloride, tetrahydrofuran, or toluene.

The compound of formula (9) may be a commercially available product, or alternatively is easily available by synthesis by a conventional method known to a person having ordinary skill in the art. The amount of the compound of formula (9) used is preferably 1 to 3 molar equivalents based on the compound of formula (8).

Bases usable herein include, for example, inorganic bases, for example, sodium carbonate, potassium carbonate, calcium carbonate, and sodium hydrogencarbonate; tertiary amines such as triethylamine, diisopropylethylamine, tri-n-butylamine, N-ethylpiperidine, and N-methylmorpholine; aromatic amines such as pyridine, 2,6-lutidine, and N,N-dimethylaminopyridine; and alkali metal amides such as lithium diisopropylamide, lithium isopropylcyclohexylamide, lithium dicyclohexylamide, lithium bistrimethylsilylamide, sodium bistrimethylsilylamide, potassium bistrimethylsilylamide, bromomagnesium diisopropylamide, iodomagnesium diisopropylamide, bromomagnesium bistrimethylsilylamide, iodomagnesium bistrimethylsilylamide, lithium-N-isopropyl-N-phenylamide, and lithium-N-isopropyl-N-naphthylamide. The base is preferably triethylamine, diisopropylethylamine, pyridine, or 2,6-lutidine. The amount of the base used is preferably 1 to 3 molar equivalents relative to the compound of formula (8) or formula (8').

The reaction temperature may vary depending upon the solvent used and the like. In general, however, the reaction temperature is in a range of −80° C. to the reflux temperature of the solvent used. The reaction time may vary depending upon the solvent used, the reaction temperature and the like. In general, however, the reaction time is 10 min to 24 hr.

The compound of formula (1) wherein Y=O thus obtained may be subjected to conventional post treatment. Further, isolation and purification may be carried out by optionally applying conventional methods such as precipitation, crystallization, gel-filtration, and column chromatography on silica gel.

(IV) Production of Compounds of Formula (1) wherein Y Represents Group $P(R^3)^3$ (a)

Compounds of formula (1), wherein Y represents group $P(R^3)^3$, can be synthesized, for example, by the process shown in scheme IV below.

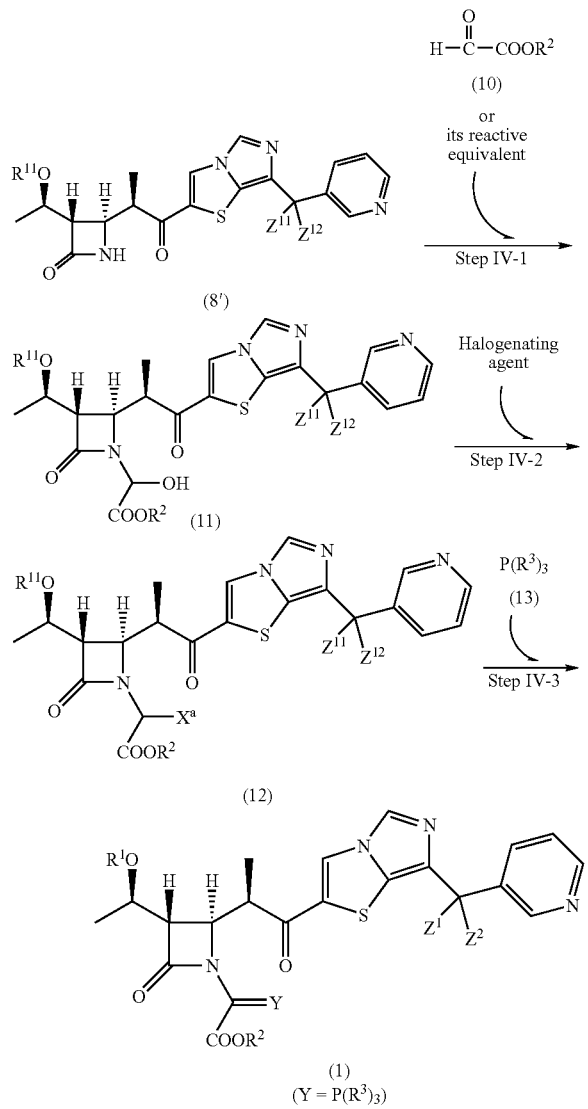

wherein $R^1$, $R^{11}$, $R^2$, $R^3$, $Z^1$, $Z^2$, $Z^{11}$, and $Z^{12}$ are as defined above; and $X^a$ represents a halogen atom.

In the present invention, as shown in scheme IV, the production process of the compound of formula (1) wherein Y represents group $P(R^3)_3$ comprises reacting the compound of formula (8) (preferably a compound of formula (8')) with a compound of formula (10) or its reactive equivalent to give a compound of formula (11), halogenating hydroxyl in the compound of formula (11) with a halogenating agent, and reacting the resultant compound (typically a compound of formula (12)) with a compound of formula (13). The compound of formula (10) and the compound of formula (13) are as follows:

$$HC(=O)-COOR^2 \qquad (10)$$

$$P(R^3)_3 \qquad (13)$$

wherein $R^2$ and $R^3$ are as defined above.

The "reactive equivalent" of the compound of formula (10) as used herein may be any compound that is a compound which can cause a reaction equivalent to the reaction caused when the compound of formula (10) is used and can be easily selected by a person having ordinary skill in the art. Specific examples of the "reactive equivalent" include hydrates of the compound of formula (10) and hemiacetals thereof. For example, monohydrate ($HOCH(OH)COOR^2$) may be mentioned as a suitable hydrate of the compound of formula (10). The "reactive equivalent" of the compound of formula (10) is preferably monohydrate, more preferably glyoxylic acid (4-nitrobenzyl)ester monohydrate or glyoxylic acid allyl ester monohydrate.

Specifically, according to the process shown in scheme IV, in step IV-1, the compound of formula (11) is produced by reacting the compound of formula (8') with the compound of formula (10) or its reactive equivalent. In step IV-2, the compound of formula (12) is produced by reacting hydroxyl in the compound of formula (11) with a halogenating agent in the presence of a base. In step IV-3, the compound of formula (1) is produced by reacting the compound of formula (12) with the compound of formula (13).

(Step IV-1)

The solvent used in step IV-1 is not particularly limited and may be properly synthesized by a person having ordinary skill in the art, so far as the solvent is inert to the reaction. Specific examples of solvents include benzene, toluene, xylene, dioxane, and dimethylformamide. The solvent is preferably toluene.

The compound of formula (10) or its reactive equivalent may be a commercially available product, or alternatively is easily available by synthesis by a conventional method known to a person having ordinary skill in the art. The amount of the compound of formula (10) or its reactive equivalent used is preferably 1 to 3 molar equivalents relative to the compound of formula (8').

The reaction temperature may vary depending upon the solvent used or the like. In general, however, the reaction temperature is in a range of room temperature to the reflux temperature of the solvent used. The reaction time may vary depending upon the solvent used, the reaction temperature and the like. In general, however, the reaction time is 10 min to 24 hr.

The compound of formula (11) thus obtained may be subjected to conventional post treatment. Further, isolation and purification may be carried out by optionally applying conventional methods such as precipitation, crystallization, gel filtration, and column chromatography on silica gel.

(Step IV-2)

The solvent used in step IV-2 is not particularly limited and may be properly synthesized by a person having ordinary skill in the art, so far as the solvent is inert to the reaction. Specific examples of solvents include ether, tetrahydrofuran, dioxane, methylene chloride, chloroform, ethyl acetate, toluene, and dimethylformamide. The solvent is preferably tetrahydrofuran.

The halogenating agent may be any conventional halogenating agent. Specific examples of halogenating agents include thionyl chloride, thionyl bromide, phosphorusoxy chloride, and phosphorusoxy bromide. Preferably, the halogenating agent is thionyl chloride. The amount of the halogenating agent used is preferably 1 to 3 equivalents relative to the compound of formula (11).

Bases usable herein include, for example, tertiary amines such as triethylamine, diisopropylethylamine, tri-n-butylamine, N-ethylpiperidine, and N-methylmorpholine; and aromatic amines such as pyridine, 2,6-lutidine, and N,N-dimethylaminopyridine. The base is preferably pyridine or 2,6-lutidine. The amount of the base used is preferably 1 to 3 molar equivalents relative to the compound of formula (11).

The reaction temperature may vary depending upon the solvent used and the like. In general, however, the reaction temperature is in a range of −50° C. to the reflux temperature of the solvent used. The reaction time may vary depending upon the solvent used, the reaction temperature and the like. In general, however, the reaction time is 10 min to 24 hr.

The compound of formula (12) may be subjected to conventional post treatment. Further, isolation and purification may be carried out by optionally applying conventional methods such as precipitation, crystallization, gel filtration, and column chromatography on silica gel.

(Step IV-3)

The solvent used in step IV-3 is not particularly limited and may be properly synthesized by a person having ordinary skill in the art, so far as the solvent is inert to the reaction. Specific examples of solvents include hexane, toluene, ether, tetrahydrofuran, dioxane, and dimethylformamide. The solvent is preferably dimethylformamide.

Examples of the compound of formula (13) include tri-n-butylphosphine, tri-t-butylphosphine, triphenylphosphine, and tri-p-tolylphosphine. The compound of formula (13) is preferably triphenylphosphine. The compound of formula (13) may be a commercially available product, or alternatively is easily available by synthesis by a conventional method known to a person having ordinary skill in the art. The amount of the compound of formula (13) used is preferably 1 to 3 molar equivalents relative to the compound of formula (12).

The reaction temperature may vary depending upon the solvent used or the like. In general, however, the reaction temperature is in a range of room temperature to the reflux temperature of the solvent used. The reaction time may vary depending upon the solvent used, the reaction temperature and the like. In general, however, the reaction time is 10 min to 24 hr.

The compound of formula (1), wherein Y represents group $P(R^3)_3$, may be subjected to conventional post treatment. Further, isolation and purification may be carried out by optionally applying conventional methods such as precipitation, crystallization, gel filtration, and column chromatography on silica gel.

(V) Production of Compounds of Formula (1) wherein Y Represents Group $P(R^3)^3$ (b)

Compounds of formula (1) wherein Y represents group $P(R^3)^3$ can also be synthesized, for example, by the process shown in scheme V below.

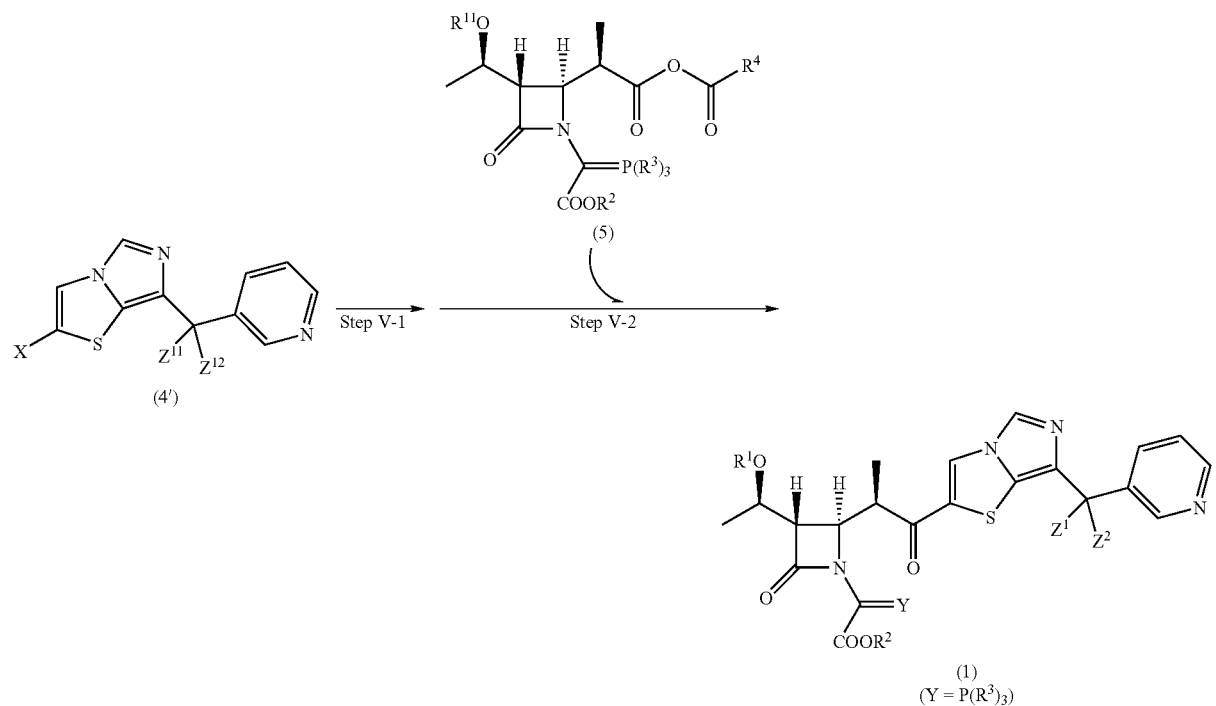

wherein $R^1$, $R^{11}$, $R^2$, $R^3$, $R^4$, $Z^1$, $Z^2$, $Z^{11}$, $Z^{12}$, and X are as defined above.

In the present invention, as shown in scheme V, the production process of the compound of formula (1) wherein Y represents group $P(R^3)_3$ comprises reacting the reaction mixture, prepared by treating the compound of formula (4') with a Grignard reagent, with the compound of formula (5).

Specifically, according to the process shown in scheme V, in a solvent inert to the reaction, in step V-1, the compound of formula (4) (preferably the compound of formula (4')) is treated with a Grignard reagent, and, subsequently, in step V-2, the compound of formula (1), wherein Y represents group $P(R^3)_3$, is produced by reacting the reaction mixture with the compound of formula (5).

(Step V-1)

The solvent used in step V-1 is not particularly limited and may be properly synthesized by a person having ordinary skill in the art, so far as the solvent is inert to the reaction. Specific examples of solvents include methylene chloride, ether, tetrahydrofuran, dioxane, benzene, and toluene. Preferably, the solvent is tetrahydrofuran.

Grignard reagents include, for example, alkylmagnesium chlorides, alkylmagnesium bromides, alkylmagnesium iodides, and arylmagnesium bromides. The Grignard reagent is preferably an alkylmagnesium bromide. The amount of Grignard reagent used is preferably 1 to 2 molar equivalents relative to the compound of formula (4').

In one preferred embodiment of the present invention, the treatment with the Grignard reagent is carried out using an alkylmagnesium bromide as the Grignard reagent in a solvent selected from the group consisting of methylene chloride, ether, tetrahydrofuran, dioxane, benzene, and toluene.

The reaction temperature may vary depending upon the solvent used or the like. In general, however, the reaction temperature is in a range of $-100°$ C. to the reflux temperature of the solvent used. The reaction time may vary depending upon the solvent used, the reaction temperature and the like. In general, however, the reaction time is 10 min to 24 hr.

The reaction mixture thus obtained as such may be used in step V-2.

(Step V-2)

The solvent used in step V-2 is not particularly limited and may be properly synthesized by a person having ordinary skill in the art, so far as the solvent is inert to the reaction. Specific examples of solvents include methylene chloride, ether, tetrahydrofuran, dioxane, benzene, and toluene. The solvent is preferably toluene or tetrahydrofuran.

The compound of formula (5) is available by synthesis by the method described in WO01/53305. Examples of preferred compounds of formula (5) include (3S,4R)-1-[allyloxycarbonyl(triphenylphosphoranylidene)methyl]-3-[(1R)-1-(t-butyldimethylsilyloxy)ethyl]-4-[(1R)-1-(4-dimethylaminobenzoyl-oxycarbonyl)ethyl]azetidin-2-one, or (3S,4R)-1-[allyloxy carbonyl(triphenylphosphoranylidene)methyl]-3-[(1R)-1-(t-butyldimethylsilyloxy)ethyl]-4-[(1R)-1-(4-diethylaminobenzoyloxycarbonyl)ethyl]azetidin-2-one. The amount of the compound of formula (5) used is preferably 1 to 3 molar equivalents relative to the compound of formula (4').

The reaction temperature may vary depending upon the solvent used or the like. In general, however, the reaction temperature is in a range of $-100°$ C. to the reflux temperature of the solvent used. The reaction time may vary depending upon the solvent used, the reaction temperature and the like. In general, however, the reaction time is 10 min to 24 hr.

The compound of formula (1) wherein Y represents group $P(R^3)_3$ thus obtained may be subjected to conventional post treatment. Further, isolation and purification may be carried out by optionally applying conventional methods such as precipitation, crystallization, gel filtration, and column chromatography on silica gel.

When $Z^1$ and $Z^2$ in formula (1) together represent the protective group of carbonyl, this compound can be converted to the compound of formula (1) wherein $Z^1$ and $Z^2$ together represent an oxygen atom by removing the protective group. The reaction for removing the protective group may vary depending upon the type of the protective group. The reaction, however, may be carried out by using as reference a reaction for removing a protective group of carbonyl in the conventional organic synthetic chemistry. For example, when $Z^1$ and $Z^2$ represent methoxy, dimethoxy as the protective group may be removed by reacting the compound of formula (1) with an acid, such as hydrochloric acid, sulfuric acid, methanesulfonic acid, or trifluoroacetic acid, in an amount of 0.1 to 100 molar equivalents relative to the compound of formula (1), in a solvent inert to the reaction, for example, methanol, ethanol, water, tetrahydrofuran, dioxane, dimethylformamide, methylene chloride, chloroform, acetone, or acetonitrile, at a temperature in a range of $-20°$ C. to the reflux temperature of the solvent used for 10 min to 24 hr. In this case, the protective group of hydroxyl in $R^1$ may be simultaneously removed to bring $R^1$ to a hydrogen atom.

When one of $Z^1$ and $Z^2$ in formula (1) represents a hydrogen atom with the other representing protected hydroxyl, this compound can be converted to the compound of formula (1), wherein one of $Z^1$ and $Z^2$ represents a hydrogen atom with the other representing hydroxyl, by removing the protective group of hydroxyl. Upon an additional oxidation reaction, the compound can be converted to the compound of formula (1) wherein $Z^1$ and $Z^2$ together represent an oxygen atom. The reaction for removing the protective group of hydroxyl may vary depending upon the type of the protective group. However, the reaction may be carried out by using as reference a reaction for removing a protective group of hydroxyl in the conventional organic synthetic chemistry. For example, when the protective group of hydroxyl is triethylsilyl, triethylsilyl as the protective group may be removed by reacting the compound of formula (1) using an acid, such as hydrochloric acid, sulfuric acid, methanesulfonic acid, or trifluoroacetic acid, or a fluorine reagent such as tetrabutylammonium fluoride, in an amount of 0.1 to 100 molar equivalents relative to the compound of formula (1) in a solvent inert to the reaction, for example, methanol, ethanol, water, tetrahydrofuran, dioxane, dimethylformamide, methylene chloride, chloroform, acetone, or acetonitrile, at a temperature in a range of $-20°$ C. to the reflux temperature of the solvent used for 10 min to 24 hr. Here the protective group of hydroxyl in $R^1$ may be simultaneously removed to bring $R^1$ to a hydrogen atom. The oxidization reaction may be carried out by using as reference an oxidization reaction in the conventional organic synthetic chemistry. For example, when manganese dioxide is utilized in the oxidization reaction, the compound of formula (1), wherein $Z^1$ and $Z^2$ together represent carbonyl, can be produced by reacting the compound of formula (1) with manganese dioxide in an amount of 1 to 10 times by weight that of the compound of formula (1), in a solvent inert to the reaction, for example, methylene chloride, chloroform, methanol, ethanol, ethyl acetate, or tetrahydrofuran, at a temperature in a range of $-20°$ C. to the reflux temperature of the solvent used for 10 min to 24 hr.

The compound of formula (1) thus obtained may be subjected to conventional post treatment. Further, isolation and purification may be carried out by optionally applying conventional methods such as precipitation, crystallization, gel filtration, and column chromatography on silica gel.

The compound of formula (2) may be produced by treating the compound of formula (1) under conditions which can form a carbapenem ring. Conditions for carbapenem ring formation are well known to a person having ordinary skill in the art.

(VI) Production of Compounds of Formula (2) (a)

Compounds of formula (2) can be synthesized from the compound of formula (1) wherein Y represents oxygen by the process shown below.

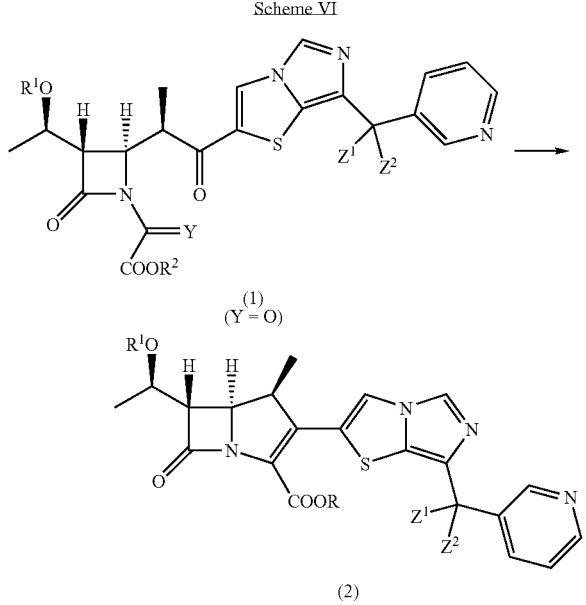

wherein $R^1$, $R^2$, R, $Z^1$, and $Z^2$ are as defined above.

In the present invention, the production process of the compound of formula (2) comprises treating the compound of formula (1) under conditions for carbapenem ring formation to form a carbapenem ring through a ring-closing reaction and optionally subjecting the resultant compound to the removal of the protective group and/or oxidation.

According to the process shown in scheme VI, the compound of formula (2) is produced by reacting the compound of formula (1), wherein Y represents an oxygen atom, with the compound of formula (21) in a solvent inert to the reaction.

$$P(R^9)_3 \quad (21)$$

wherein $R^9$s, which may be the same or different, represent C1-6 alkyl or C1-6 alkoxy.

Accordingly, in one preferred embodiment of the present invention, the treatment for carbapenem ring formation is carried out by reacting the compound of formula (1) with the compound of formula (21).

The solvent used is not particularly limited and may be properly synthesized by a person having ordinary skill in the art, so far as the solvent is inert to the reaction. Specific examples of solvents include hexane, methylene chloride, chloroform, isopropyl alcohol, ether, tetrahydrofuran, dioxane, and toluene. The solvent is preferably isopropyl alcohol or toluene.

Compounds of formula (21) include, for example, triethyl phosphite, trimethyl phosphite and dimethyl methylphosphonite, and diethyl methylphosphonite. The compound of formula (21) is preferably diethyl methylphosphonite. The compound of formula (21) may be a commercially available product, or alternatively is easily available by synthesis by a conventional method known to a person having ordinary skill in the art. The amount of the compound of formula (21) used is preferably 1 to 10 molar equivalents relative to the compound of formula (1).

The reaction temperature may vary depending upon the solvent used or the like. In general, however, the reaction temperature is in a range of room temperature to the reflux temperature of the solvent used. The reaction time may vary depending upon the solvent used, the reaction temperature and the like. In general, however, the reaction time is 10 min to 24 hr.

The compound of formula (2) thus obtained may be subjected to conventional post treatment. Further, isolation and purification may be carried out by optionally applying conventional methods such as precipitation, crystallization, gel filtration, and column chromatography on silica gel.

(VII) Production of Compounds of Formula (2) (b)

The compound of formula (2) can be synthesized from the compound of formula (1) wherein Y represents group $P(R^3)_3$ by the process shown in scheme VII below.

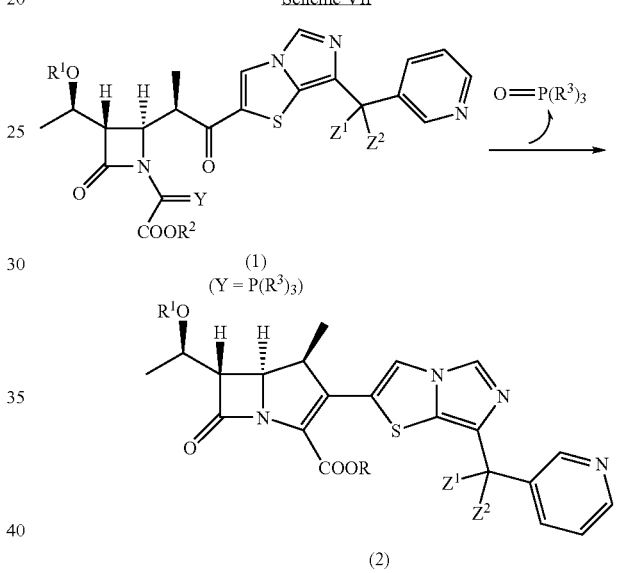

wherein $R^1$, $R^2$, $R^3$, R, $Z^1$, and $Z^2$ are as defined above.

In the present invention, the production process of the compound of formula (2) comprises treating the compound of formula (1) under conditions for carbapenem ring formation to form a carbapenem ring through a ring-closing reaction and optionally subjecting the resultant compound to the removal of the protective group and/or oxidation.

According to the process shown in scheme VII, the compound of formula (2) is produced by eliminating group O=P$(R^3)_3$ from the compound of formula (1) wherein Y represents $P(R^3)_3$, to form a ring.

Accordingly, in one preferred embodiment of the present invention, the treatment for carbapenem ring formation is carried out by eliminating group O=P$(R^3)_3$ from the compound of formula (1).

The solvent used is not particularly limited and may be properly synthesized by a person having ordinary skill in the art, so far as the solvent is inert to the reaction. Specific examples of solvents include hexane, methylene chloride, chloroform, isopropyl alcohol, ether, tetrahydrofuran, dioxane, and toluene. The solvent is preferably toluene. The amount of the solvent used is preferably about 5 to 100 times by weight of that of the compound of formula (1).

The reaction temperature may vary depending upon the solvent used or the like. In general, however, the reaction temperature is in a range of room temperature to the reflux temperature of the solvent used. The reaction time may vary depending upon the solvent used, the reaction temperature and the like. In general, however, the reaction time is 10 min to 24 hr.

When $Z^1$ and $Z^2$ in formula (2) together represent the protective group of carbonyl, this compound can be converted to the compound of formula (2) wherein $Z^1$ and $Z^2$ together represent an oxygen atom by removing the protective group. The reaction for removing the protective group may vary depending upon the type of the protective group. The reaction, however, may be carried out by using as reference a reaction for removing a protective group of carbonyl in the conventional organic synthetic chemistry. In this case, the protective group of hydroxyl in $R^1$ may be simultaneously removed to bring $R^1$ to a hydrogen atom.

When one of $Z^1$ and $Z^2$ in formula (2) represents a hydrogen atom with the other representing protected hydroxyl, this compound can be converted to the compound of formula (2), wherein one of $Z^1$ and $Z^2$ represents a hydrogen atom with the other representing hydroxyl, by removing the protective group of hydroxyl. Upon an additional oxidation reaction, the compound can be converted to the compound of formula (2) wherein $Z^1$ and $Z^2$ together represent an oxygen atom. The reaction for removing the protective group of hydroxyl may vary depending upon the type of the protective group. However, the reaction may be carried out by using as reference a reaction for removing a protective group of hydroxyl in the conventional organic synthetic chemistry. In this case, the protective group of hydroxyl in $R^1$ may be simultaneously removed to bring $R^1$ to a hydrogen atom. The oxidization reaction may be carried out by using as reference an oxidization reaction in the conventional organic synthetic chemistry.

The compound of formula (2) thus obtained may be subjected to conventional post treatment. Further, isolation and purification may be carried out by optionally applying conventional methods such as precipitation, crystallization, gel filtration, and column chromatography on silica gel.

(VIII) Production of Compounds of Formula (3)

Compounds of formula (3) can be synthesized from the compound of formula (2) by the process shown in scheme VIII below.

Scheme VIII

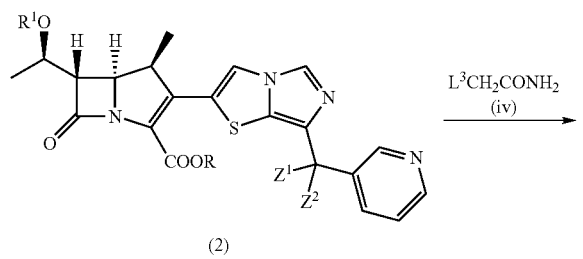

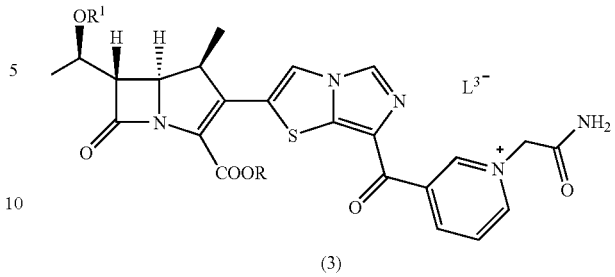

wherein $R^1$, R, $L^3$, $Z^1$, and $Z^2$ are as defined above.

In the present invention, the compound of formula (3) can be produced by reacting the compound of formula (2) with the compound of formula (iv).

$$L^3CH_2CONH_2 \quad (iv)$$

wherein $L^3$ represents a leaving group.

The solvent used herein is not particularly limited and may be properly synthesized by a person having ordinary skill in the art, so far as the solvent is inert to the reaction. Specific examples of solvents include acetone, methanol, ethanol, isopropanol, and dioxane. The solvent is preferably methanol.

Examples of compounds of formula (iv) include bromoacetamide, iodoacetamide, and trifluoromethanesulfonyloxyacetamide. The compound of formula (iv) is preferably iodoacetamide.

The compound of formula (iv) may be a commercially available product, or alternatively is easily available by synthesis by a conventional method known to a person having ordinary skill in the art. The amount of the compound of formula (iv) used is preferably 1 to 5 molar equivalents relative to the compound of formula (2).

The reaction temperature may vary depending upon the solvent used or the like. In general, however, the reaction temperature is in a range of −20° C. to the reflux temperature of the solvent used. The reaction time may vary depending upon the solvent used, the reaction temperature and the like. In general, however, the reaction time is 10 min to 24 hr.

The compound of formula (3) thus obtained may be subjected to conventional post treatment. Further, isolation and purification may be carried out by optionally applying conventional methods such as precipitation, crystallization, gel filtration, and column chromatography on silica gel.

(IX) Production of Compounds of Formula (A)

Compounds of formula (A) can be synthesized from the compound of formula (2) by the process shown in scheme IX.

Scheme IX

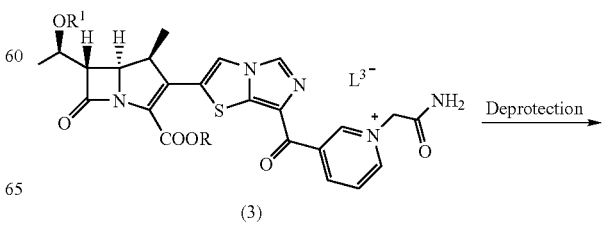

-continued

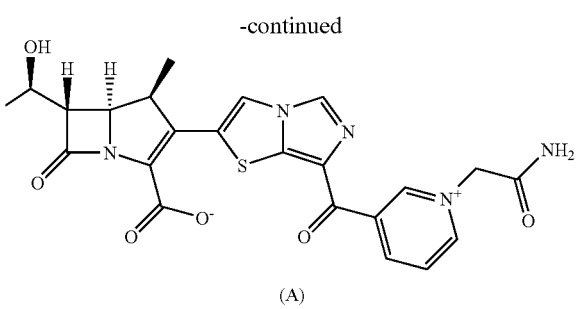

(A)

wherein $R^1$, R, and $L^3$ are as defined above.

The compound of formula (A) can be produced by removing the protective group of the compound of formula (3) by deprotection. The reaction for removing the protective group of hydroxyl and the protective group of carboxyl may vary depending upon the type of the protective group. The reaction, however, may be carried out by using as reference a reaction for removing a protective group of hydroxyl in the conventional organic synthetic chemistry. For example, when the protective group $R^1$ of hydroxyl is triethylsilyl, triethylsilyl as the protective group can be removed by reacting the compound of formula (3) with an acid such as hydrochloric acid, sulfuric acid, methanesulfonic acid, or trifluoroacetic acid, or a fluorine reagent such as tetrabutylammonium fluoride, in an amount of 0.1 to 10 molar equivalents relative to the compound of formula (3) in a solvent inert to the reaction, for example, methanol, ethanol, water, tetrahydrofuran, dioxane, dimethylformamide, methylene chloride, chloroform, acetone, or acetonitrile, at a temperature in a range of −20° C. to the reflux temperature of the solvent used for 10 min to 24 hr. When the protective group R of carboxyl is 4-nitrobenzyl (pNB), the protective group can be removed by the method described in WO 02/42314.

In one preferred embodiment of the present invention, the compound of formula (A) is produced by removing the protective group of the compound of formula (3) by deprotection.

The compound of formula (A) thus obtained may be subjected to conventional post treatment. Further, isolation and purification may be carried out by optionally applying conventional methods such as precipitation, crystallization, gel filtration, and column chromatography on silica gel.

In another embodiment of the present invention, the production process of the compound of formula (A) comprises preparing the compound of formula (2) from the compound of formula (1) by the production process of the compound of formula (2). Preferably, the production process of the compound of formula (A) further comprises preparing the compound of formula (1) by the production process of the compound of formula (1).

Use of Compounds

The compounds of formula (1), formula (4), formula (6), formula (8), and formula (14a) according to the present invention are useful as intermediates for the production of carbapenem derivatives (compound of formula (A)) having 7-(1-carbamoylmethylpyridinium-3-yl)carbonylimidazo[5,1-b]thiazole at the 2-position on the carbapenem ring.

As disclosed in WO 02/42312, carbapenem derivatives of formula (A) produced by using compounds of formula (1) according to the present invention have high antimicrobial activities against a wide spectrum of Gram-positive bacteria and Gram-negative bacteria and, at the same time, have high antimicrobial activities against MRSA, PRSP, *Haemophilus influenzae* and β-lactamase producing bacteria. Further, as disclosed in this publication, they have low toxicity and are also stable to DHP-1. Use of the above derivatives as therapeutic agents of infectious diseases caused by various pathogenic bacteria in animals including humans, and the manufacture of pharmaceutical compositions using the above compounds will be apparent to a person having ordinary skill in the art by reference to the above publication.

EXAMPLES

The present invention is further illustrated by the following Examples that are not intended as a limitation of the invention.

Example 1

5-Bromo-2-t-butoxycarbonylaminomethylthiazole

A solution (2 L) of 1.33 kg of 2-t-butoxy carbonylaminomethylthiazole in ethyl acetate was added to an aqueous solution (20 L) of 8.6 kg of sodium acetate, and the mixture was stirred. Bromine (1.35 L) was added dropwise to this solution (internal temperature: 19 to 24° C.) over a period of 3.5 hr, and the mixture was stirred at an internal temperature of 25.5±5° C. for 14 hr. Sodium sulfite pentahydrate (180 g) was added thereto, the mixture was then extracted with 3 L of ethyl acetate, and the organic layer was washed with 1 L of water and 1.53 L of a 6 M aqueous sodium hydroxide solution. The aqueous layer was then extracted with 3 L of ethyl acetate. The organic layers were combined, were dried over anhydrous magnesium sulfate, and were filtered. The solvent was removed from the filtrate by evaporation under the reduced pressure, followed by substitution concentration twice with 2 L of ethanol to give 944 g of 5-bromo-2-t-butoxy carbonylaminomethylthiazole.

$^1$H-NMR (CDCl$_3$) δ: 1.40 (9H, s), 4.48 (2H, d, J=6.1 Hz), 5.16 (1H, brs), 7.51 (1H, s)

Example 2

2-Aminomethyl-5-bromothiazole hydrochloride

4 N hydrochloric acid dioxane solution (2.3 L) was added dropwise to a solution (1.6 L) of 542 g of 5-bromo-2-t-butoxycarbonylaminomethylthiazole in ethanol at an internal temperature of 40° C. over a period of 1.1 hr. The mixture was stirred until the internal temperature reached 23° C. The precipitated crystal was collected by filtration, was washed twice with ethanol, and was then dried under the reduced pressure to give 394 g of 2-aminomethyl-5-bromothiazole hydrochloride.

$^1$H-NMR (CDCl$_3$) δ: 4.37 (2H, s), 7.72 (1H, s)

Example 3

5-Bromo-2-formylaminomethylthiazole

2-Aminomethyl-5-bromothiazole hydrochloride (350 g) was dissolved in 7 L of ethyl formate. To this solution were added 296 ml of a 28% methanol solution of sodium methoxide and 173 ml of a formic acid solution. The mixture was then stirred at an internal temperature of 48° C. for 5 hr. The solvent was removed by evaporation under the reduced pressure. When precipitate occurred, ethanol was added to dissolve the precipitate. The solvent was again removed by evaporation under the reduced pressure until crystal was formed. The solution was stirred under ice cooling overnight. The precipitated crystal was then collected by filtration, was then washed with cold ethanol and hexane, and was dried under the reduced pressure to give 189 g of 5-bromo-2-formylaminomethylthiazole. Further, the filtrate was concentrated, and the concentrate was crystallized from ethanol to give 58 g of secondary-crystal.

$^1$H-NMR (CDCl$_3$) δ: 4.71 (2H, d, J=6.6 Hz), 6.58 (1H, s), 7.59 (1H, s), 8.29 (1H, s)

Example 4

5-Bromo-2-formylaminomethylthiazole

2-Formylaminomethylthiazole (200 g) was added to a solution of 4.5 kg of sodium dihydrogenphosphate dihydrate in 6 L of water, and the mixture was stirred at 30° C. Sodium bromide (4.0 kg) and 2 L of tetrahydrofuran were added thereto in that order. Bromine (1.49 kg) was added while adjusting the solution to pH 3 by the addition of a 6 N aqueous sodium hydroxide solution, and the mixture was stirred for 2 hr. The reaction mixture was added to a solution of 500 g of sodium sulfite in 4 L of water to stop the reaction and was then adjusted to pH 4.9 by the addition of a 6 N aqueous sodium hydroxide solution while maintaining the temperature of the mixture at 30° C. The reaction mixture was extracted with 10 L of ethyl acetate and then with 5 L of ethyl acetate. The organic layers were combined and were dried over anhydrous magnesium sulfate. The solvent was removed to bring the volume to 1 L, and the concentrate was stirred at 6° C. for 12 hr for crystallization to give 104.4 g of 5-bromo-2-formylaminomethylthiazole. The results of NMR analysis were in agreement with the results of analysis in Example 3.

Example 5

2-Bromoimidazo[5,1-b]thiazole

Toluene (1.0 L) was added to 104 g of 5-bromo-2-formylaminomethylthiazole, and the mixture was heated to 90° C. and was stirred. A solution of 65.8 g of phosphorus oxychloride in 100 ml of toluene was added to the reaction mixture, and the mixture was stirred at that temperature for 1.5 hr. After standing to cool, 2 L of a 0.5 N aqueous hydrochloric acid solution was added, and the aqueous layer was separated. The aqueous layer was adjusted to pH 6.2 by the addition of a 5 N aqueous sodium hydroxide solution and was extracted with 1.5 L of ethyl acetate and then with 1.0 L of ethyl acetate. The organic layers were combined, were washed with a 5% aqueous sodium bicarbonate solution and a 20% aqueous sodium chloride solution in that order, and were dried over anhydrous magnesium sulfate. The solvent was removed to bring the volume to about 100 ml, 500 ml of ethyl acetate:hexane=1:4 solution was added thereto, and the mixture was stirred in an ice-water bath for crystallization to give 57.6 g of 2-bromimidazo[5,1-b]thiazole.

$^1$H-NMR (CDCl$_3$) δ: 7.05 (1H, s), 7.48 (1H, s), 7.96 (1H, s)

Example 6

2-Bromo-7-formylimidazo[5,1-b]thiazole

Dimethylformamide (0.13 ml) and 0.15 ml of phosphorus oxychloride were added in that order to a solution of 300 mg of 2-bromoimidazo[5,1-b]thiazole in 3 ml of methylene chloride under an argon atmosphere, and the mixture was stirred at 80° C. for 6 hr. Water was added to the reaction mixture to stop the reaction, and the reaction mixture was adjusted to pH 10 by the addition of a 1 N aqueous sodium hydroxide solution. The reaction mixture was then extracted with ethyl acetate, and the organic layer was then washed with saturated brine and was dried over magnesium sulfate. The solvent was removed by evaporation, and the residue was purified by column chromatography on silica gel (hexane:ethyl acetate=1:10) to give 223 mg of 2-bromo-7-formylimidazo[5,1-b]thiazole.

$^1$H-NMR (CDCl$_3$) δ: 7.66 (1H, s), 8.02 (1H, s), 9.90 (1H, s)

Example 7

2-Bromo-7-hydroxy(pyridin-3-yl)methylimidazo[5,1-b]thiazole

A 1 M tetrahydrofuran solution (0.9 ml) of ethylmagnesium bromide was added to a solution of 147 mg of 3-iodopyridine in 1 ml of tetrahydrofuran under an argon atmosphere, and the mixture was stirred at room temperature for 30 min. A solution of 149 mg of 2-bromo-7-formylimidazo[5,1-b]thiazole in 2 ml of tetrahydrofuran was added to the solution, and the mixture was stirred at that temperature for 2.5 hr. An aqueous saturated ammonium chloride solution was added to the reaction mixture to stop the reaction, and the reaction mixture was extracted with ethyl acetate. The organic layer was washed with water and saturated brine in that order and was then dried over magnesium sulfate. The solvent was removed by evaporation, and the residue was purified by column chromatography on silica gel (ethyl acetate:methanol=4:1) to give 147 mg of 2-bromo-7-(pyridin-3-yl)hydroxymethylimidazo[5,1-b]thiazole.

$^1$H-NMR (CDCl$_3$) δ: 6.04 (1H, s), 7.32-7.36 (1H, m), 7.84 (1H, s), 7.91 (1H, s), 8.58 (1H, dd, J=2.2, 4.7 Hz), 8.67 (1H, d, J=2.2 Hz)

Example 8

2-Bromo-7-(pyridin-3-yl)triethylsilyloxy methylimidazo[5,1-b]thiazole

Diisopropylethylamine (3.1 ml) and 3.0 ml of triethylsilylchloride were added in that order to a solution of 4.05 g of 2-bromo-7-(pyridin-3-yl)hydroxymethylimidazo[5,1-b]thiazole in 30 ml of dimethylformamide, and the mixture was stirred at room temperature for one hr. The reaction mixture was diluted with ethyl acetate, and the diluted reaction mixture was washed with water, a 5% aqueous sodium bicarbonate solution, and a 20% aqueous sodium chloride solution in that order and was dried over anhydrous magnesium sulfate. The solvent was removed by evaporation, and the residue was purified by column chromatography on silica gel (2 to 5% methanol/methylene chloride) to give 5.14 g of 2-bromo-7-(pyridin-3-yl)triethylsilyloxymethylimidazo[5,1-b]thiazole.

$^1$H-NMR (CDCl$_3$) δ: 0.59-0.68 (6H, m), 0.88-0.94 (9H, m), 5.95 (1H, s), 7.25 (1H, dd, J=4.7, 8.0 Hz), 7.41 (1H, s), 7.76 (1H, m), 7.83 (1H, s), 8.50-8.52 (1H, dd, J=2.2, 4.7 Hz), 8.72 (1H, d, J=2.2 Hz)

Example 9

2-Bromo-7-(pyridin-3-yl)carbonylimidazo[5,1-b]thiazole

Manganese dioxide (645 mg) was added to a solution of 645 mg of 2-bromo-7-(pyridin-3-yl)hydroxymethylimidazo[5,1-b]thiazole in 12 ml of methylene chloride, and the mixture was stirred at room temperature for 22 hr. The reaction mixture was filtered through Celite, followed by washing with methylene chloride:methanol=10:1. The solvent was then removed by evaporation to give a crude solid. A hexane: ethyl acetate=3:1 solution (10 ml) was added to this solid, and the mixture was stirred at room temperature and was filtered to give 448 mg of 2-bromo-7-(pyridin-3-yl)carbonylimidazo [5,1-b]thiazole.

$^1$H-NMR (CDCl$_3$) δ: 7.43-7.47 (1H, m), 7.70 (1H, s), 8.04 (1H, s), 8.78-8.85 (2H, m), 9.72-9.73 (1H, m)

Example 10

2-Bromo-7-(pyridin-3-yl)dimethylhydrazonoylimidazo[5,1-b]thiazole

Acetic acid (0.86 ml) and 1.9 ml of dimethylhydrazine were added to a suspension of 1.89 g of 2-bromo-7-(pyridin-3-yl)carbonylimidazo[5,1-b]thiazole in 25 ml of ethanol, and, in a sealed tube, the mixture was heated to 80° C. and was stirred for 18 hr. The reaction mixture was added to a dilute aqueous sodium bicarbonate solution to stop the reaction and was extracted with ethyl acetate. The organic layer was washed with a saturated aqueous sodium bicarbonate solution and saturated brine in that order and was dried over anhydrous magnesium sulfate. The solvent was removed by evaporation, and the solid thus obtained was washed with an ethyl acetate: hexane=1:1 solution to give 1.41 g of 2-bromo-7-(pyridin-3-yl)dimethylhydrazonoylimidazo[5,1-b]thiazole.

$^1$H-NMR (CDCl$_3$) δ: 2.62 (6H, s), 7.31-7.35 (1H, m), 7.65 (1H, s), 7.92 (1H, s), 7.98-8.01 (1H, m), 8.65 (1H, dd, J=1.6, 4.9 Hz), 8.88-8.90 (1H, m)

Example 11

2-Bromo-7-dimethoxy(pyridin-3-yl)methylimidazo [5,1-b]thiazole

Methanol (50 ml) and 32 g of methyl orthoformate were added to ~3.08 g of 2-bromo-7-(pyridin-3-yl)carbonylimidazo[5,1-b]thiazole, the mixture was heated to 50° C. for dissolution, and the solution was then cooled in an ice-water bath. Sulfuric acid (5.4 ml) was added dropwise to the reaction mixture at that temperature, and the mixture was then heated under reflux for 18 hr. After heat release, the reaction mixture was added dropwise to 80 ml of a 2.5 N aqueous sodium hydroxide solution cooled in an ice-water bath, and the mixture was extracted with ethyl acetate. The extract was dried over anhydrous magnesium sulfate and was then concentrated by removing the solvent. The solid was then collected by filtration to give 2.70 g of 2-bromo-7-dimethoxy (pyridin-3-yl)methylimidazo[5,1-b]thiazole.

$^1$H-NMR (CDCl$_3$) δ: 3.21 (6H, s), 7.24-7.29 (1H, m), 7.44 (1H, s), 7.84 (1H, s), 7.90 (1H, ddd, J=1.9, 1.9, 8.0 Hz), 8.52 (1H, dd, J=1.6, 4.9 Hz), 8.73 (1H, d, J=1.9 Hz)

Example 12

2-Bromo-7-diethoxy(pyridin-3-yl)methylimidazo[5, 1-b]thiazole

Ethanol (50 ml) and 44.5 g of ethyl orthoformate were added to 3.08 g of 2-bromo-7-(pyridin-3-yl)carbonylimidazo [5,1-b]thiazole. The mixture was heated to 50° C. for dissolution, and the solution was then cooled in an ice-water bath. Sulfuric acid (5.4 ml) was added dropwise to the reaction mixture at that temperature, and the mixture was then heated under reflex for 18 hr. After standing to cool, the reaction mixture was added dropwise to 80 ml of a 2.5 N aqueous sodium hydroxide solution cooled in an ice-water bath, and the mixture was extracted with methylene chloride. The extract was dried over anhydrous magnesium sulfate and was then concentrated by removing the solvent. The concentrate was purified by column chromatography on silica gel (5 to 12% methanol/ethyl acetate) to give 1.29 g of 2-bromo-7-diethoxy(pyridin-3-yl)methylimidazo[5,1-b]thiazole.

$^1$H-NMR (CDCl$_3$) δ: 1.26 (6H, t, J=7.1 Hz), 3.37-3.45 (4H, m), 7.23-7.27 (1H, m), 7.43 (1H, s), 7.81 (1H, s), 7.92 (1H, ddd, J=1.6, 1.6, 8.0 Hz), 8.50 (1H, dd, i=1.6, 4.7 Hz), 8.73 (1H, dd, J=0.6, 2.2 Hz)

Example 13

2-Propionyl-7-(pyridin-3-yl)triethylsilyloxymethylimidazo[5,1-b]thiazole

A solution of 5.14 g of 2-bromo-7-(pyridin-3-yl)triethylsilyloxymethylimidazo[5,1-b]thiazole in 36 ml of tetrahydrofuran under an argon atmosphere was cooled to −60° C., 13.3 ml of a 0.89 M tetrahydrofuran solution of ethylmagnesium bromide was added thereto, and the mixture was stirred for one hr. N-Methyl-N-methoxypropionamide (1.71 g) was added thereto at −30° C., and the mixture was stirred at room temperature for 12 hr. A 20% aqueous ammonium chloride solution was added to stop the reaction, and the reaction mixture was extracted with ethyl acetate. The extract was washed with a saturated aqueous sodium bicarbonate solution and saturated brine in that order and was then dried over anhydrous magnesium sulfate. The solvent was removed by evaporation, and the residue was purified by column chromatography on silica gel (3 to 6% methanol/methylene chloride) to give 3.88 g of 2-propionyl-7-(pyridin-3-yl)triethylsilyloxymethylimidazo[5,1-b]thiazole.

$^1$H-NMR (CDCl$_3$) δ: 0.56-0.82 (6H, m), 0.88-0.93 (9H, m), 1.25 (3H, t, J=7.28), 2.86 (2H, d, J=7.28), 5.98 (1H, s), 7.23-7.27 (1H, m), 7.77-7.81 (1H, m), 7.97 (1H, s), 7.98 (1H, s), 8.51 (1H, dd, J=1.9, 4.7 Hz), 8.73 (1H, d, J=1.9 Hz)

Example 14

2-Propionyl-7-(pyridin-3-yl)dimethylhydrazonoylimidazo[5,1-b]thiazole

A solution of 1.75 g of 2-bromo-7-(pyridin-3-yl)dimethylhydrazonoylimidazo[5,1-b]thiazole in 10 ml of tetrahydrofuran was cooled to −50° C. under an argon atmosphere, 15.4 ml of a 0.89 M tetrahydrofuran solution of ethylmagnesium bromide was added thereto, and the mixture was stirred for one hr. N-Methyl-N-methoxypropionamide (2.2 ml) was added thereto at −20° C., and the mixture was stirred at room temperature for one hr. A 20% aqueous ammonium chloride solution was added to stop the reaction, and the reaction mixture was extracted with ethyl acetate. The extract was washed with saturated aqueous sodium bicarbonate solution and saturated brine in that order and was then dried over anhydrous magnesium sulfate. The solvent was removed by evaporation, and the solid was washed with an ethyl acetate: hexane=2:1 solution to give 0.94 g of 2-propionyl-7-(pyridin-3-yl)dimethylhydrazonoylimidazo[5,1-b]thiazole.

¹H-NMR (CDCl₃) δ: 1.29 (3H, t, J=7.1 Hz), 2.92 (2H, q, J=7.1 Hz), 7.31-7.35 (1H, m), 7.98 (1H, ddd, J=1.6, 1.6, 8.2 Hz), 8.87-8.88 (1H, m)

Example 15

7-Dimethoxy(pyridin-3-yl)methyl-2-propionylimidazo[5,1-b]thiazole

A solution of 10.63 g of 2-bromo-7-dimethoxy(pyridin-3-yl)methylimidazo[5,1-b]thiazole in 100 ml of tetrahydrofuran under an argon atmosphere was cooled to −50° C., 40 ml of a 0.89 M tetrahydrofuran solution of ethylmagnesium bromide was added thereto, and the mixture was stirred for one hr. N-Methyl-N-methoxypropionamide (5.3 ml) was added thereto at −20° C., and the mixture was stirred at room temperature for 6 hr. A saturated aqueous ammonium chloride solution was added to stop the reaction, and the reaction mixture was extracted with ethyl acetate. The organic layer was washed with a saturated aqueous sodium bicarbonate solution and saturated brine in that order and was then dried over anhydrous magnesium sulfate. The solvent was removed by evaporation and the residue was purified by column chromatography on silica gel (5 to 15% methanol/ethyl acetate) to give a crude product of 2-propionyl-7-(pyridin-3-yl)dimethoxymethylimidazo[5,1-b]thiazole. A solution of this crude product in 200 ml of ethyl acetate was washed four times with 100 ml of an aqueous 0.02 N hydrochloric acid solution and was further washed with a 5% aqueous sodium bicarbonate solution and a 20% aqueous sodium chloride solution in that order to give 4.79 g of 7-dimethoxy(pyridin-3-yl)methyl-2-propionylimidazo[5,1-b]thiazole.

¹H-NMR (CDCl₃) δ: 1.26 (3H, t, J=7.1 Hz), 2.88 (2H, q, J=7.1 Hz), 3.22 (6H, s), 7.24-7.29 (1H, m), 7.88-7.92 (1H, m), 7.90 (1H, ddd, J=1.9, 1.9, 8.2 Hz), 7.97 (1H, s), 8.02 (1H, s), 8.52 (1H, dd, J=1.6, 4.9 Hz), 8.74-8.75 (1H, m)

Example 16

(3S,4R)-3-[(1R)-1-(tert-Butyldimethylsilyloxy)ethyl]-4-[(1R)-1-methyl-2-[7-(pyridin-3-yl)carbonylimidazo[5,1-b]thiazol-2-yl]-2-oxoethyl]azetidin-2-one

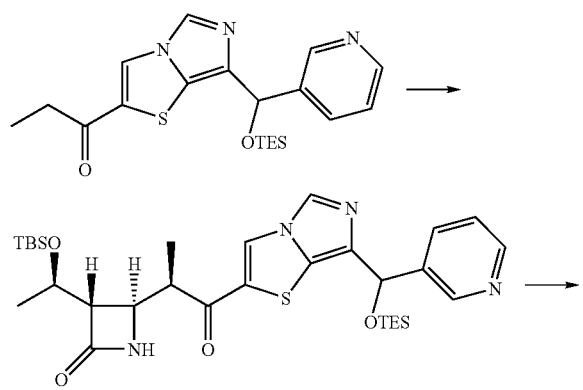

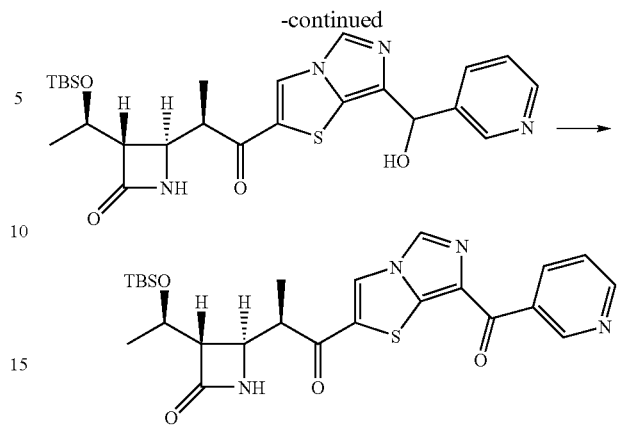

(a) (3S,4R)-3-[(1R)-1-(tert-butyldimethylsilyloxy)ethyl]-4-[1-methyl-2-[7-(pyridin-3-yl)triethylsilyloxymethylimidazo[5,1-b]thiazol-2-yl]-2-oxoethyl]azetidin-2-one A 1 M tetrahydrofuran solution (5.2 ml) of lithium bistrimethylsilylamide was added to a solution of 2.05 g of lithium bromide in 10 ml of tetrahydrofuran under an argon atmosphere, and the mixture was cooled to −78° C. A solution of 0.95 g of 2-propionyl-7-(pyridin-3-yl)triethylsilyloxymethylimidazo[5,1-b]thiazole in 4.7 ml of tetrahydrofuran was added thereto, and the mixture was stirred at that temperature for one hr. A solution of 0.81 g of (3S,4R)-4-acetoxy-3-[(1R)-1-tert-butyldimethylsilyloxyethyl]azetidin-2-one in 3.8 ml of tetrahydrofuran was added thereto, and the mixture was stirred at that temperature for 2 hr. A 10% aqueous citric acid solution was added to the reaction mixture to stop the reaction, and the reaction mixture was extracted with ethyl acetate. The extract was washed with a saturated aqueous sodium bicarbonate solution and saturated brine in that order and was then dried over anhydrous magnesium sulfate. The extract was then concentrated by removing the solvent, and the concentrate was purified by column chromatography on silica gel (5 to 10% methanol/methylene chloride) to give 0.80 g of a crude product of (3S,4R)-3-[(1R)-1-(tert-butyldimethylsilyloxy)ethyl]-4-[1-methyl-2-[7-(pyridin-3-yl)triethylsilyloxymethylimidazo[5,1-b]thiazol-2-yl]-2-oxoethyl]azetidin-2-one.

(b) (3S,4R)-3-[(1R)-1-(tert-Butyldimethylsilyloxy)ethyl]-4-[1-methyl-2-[7-hydroxy(pyridin-3-yl)methylimidazo[5,1-b]thiazol-2-yl]-2-oxoethyl]azetidin-2-one The crude product (0.80 g) of (3S,4R)-3-[(1R)-1-(tert-butyldimethylsilyloxy)ethyl]-4-[1-methyl-2-[7-(pyridin-3-yl)triethylsilyloxymethylimidazo[5,1-b]thiazol-2-yl]-2-oxoethyl]azetidin-2-one prepared in step (a) was dissolved in 7 ml of methanol, and the solution was cooled in an ice bath. A 1 N aqueous hydrochloric acid solution (2.6 ml) was added thereto, and the mixture was stirred at that temperature for 1 hr 40 min. The reaction mixture was neutralized with a dilute aqueous sodium bicarbonate solution and was extracted with methylene chloride. The extract was washed with a saturated aqueous sodium bicarbonate solution and saturated brine in that order and was then dried over anhydrous magnesium sulfate. The extract was concentrated by removing the solvent to give a crude product of (3S,4R)-3-[(1R)-1-(tert-butyldimethylsilyloxy)ethyl]-4-[1-methyl-2-[7-hydroxy(pyridin-3-yl)methylimidazo[5,1-b]thiazol-2-yl]-2-oxoethyl]azetidin-2-one.

(c) (3S,4R)-3-[(1R)-1-(tert-Butyldimethylsilyloxy)ethyl]-4-[(1R)-1-methyl-2-[7-(pyridin-3-yl)carbonylimidazo[5,1-b]thiazol-2-yl]-2-oxoethyl]azetidin-2-one The crude product of (3S,4R)-3-[(1R)-1-(tert-butyldimethylsilyloxy)ethyl]-4-[1-methyl-2-[7-hydroxy(pyridin-3-yl)methylimidazo[5,1-b]thiazol-2-yl]-2-oxoethyl]azetidin-2-one prepared in step (b) was dissolved in 13.5 ml of methylene chloride and 1.5 ml of methanol, 1 g of manganese dioxide was added thereto, and the mixture was stirred at room temperature for 4 hr. The reaction mixture was filtered through Celite, and the solvent was removed by evaporation to give 0.63 g of a crude product of (3S,4R)-3-[(1R)-1-(tert-butyldimethylsilyloxy)ethyl]-4-[1-methyl-2-[7-(pyridin-3-yl)carbonylimidazo[5,1-b]thiazol-2-yl]-2-oxoethyl]azetidin-2-one. This crude product (0.63 g) was crystallized from ethyl acetate to give 0.38 g of (3S,4R)-3-[(1R)-1-(tert-butyldimethylsilyloxy)ethyl]-4-[(1R)-1-methyl-2-[7-(pyridin-3-yl)carbonylimidazo[5,1-b]thiazol-2-yl]-2-oxoethyl]azetidin-2-one.

$^1$H-NMR (CDCl$_3$) δ: 0.06 (3H, s), 0.08 (3H, s), 0.87 (9H, s), 1.17 (3H, d, J=6.3 Hz), 1.39 (3H, d, J=6.9 Hz), 2.92 (1H, dd, J=2.2, 4.4 Hz), 3.34-3.43 (1H, m), 4.02 (1H, dd, J=4.7, 6.0 Hz), 4.14-4.23 (1H, m), 6.14 (1H, s), 7.43-7.48 (1H, m), 8.20 (1H, s), 8.26 (1H, s), 8.77-8.83 (2H, m), 9.73-9.75 (1H, m)

Example 17

(3S,4R)-3-[(1R)-1-(tert-Butyldimethylsilyloxy)ethyl]-4-[(1R)-1-methyl-2-[7-(pyridin-3-yl)dimethylhydrazonoylimidazo[5,1-b]thiazol-2-yl]-2-oxoethyl]azetidin-2-one

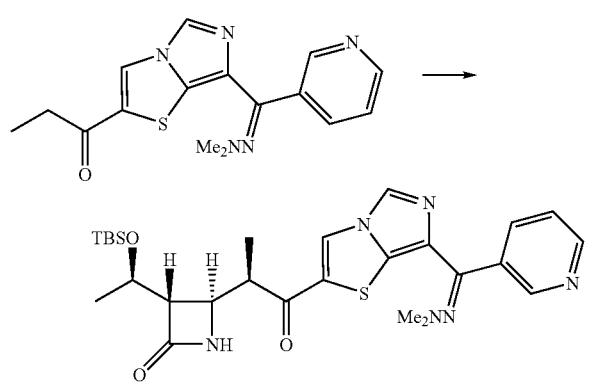

Tetrahydrofuran (1 ml) was added to 1.1 ml of a 1 M tetrahydrofuran solution of lithium bistrimethylsilylamide under an argon atmosphere, and the mixture was cooled to −78° C. A solution of 0.16 g of 2-propionyl-7-(pyridin-3-yl)dimethylhydrazonoylimidazo[5,1-b]thiazole in 2.5 ml of tetrahydrofuran was added thereto, and the mixture was stirred at that temperature for 30 min. A solution of 0.18 g of (3S,4R)-4-acetoxy-3-[(1R)-1-tert-butyldimethylsilyloxyethyl]azetidin-2-one in 1 ml of tetrahydrofuran was added thereto, and the mixture was stirred at that temperature for 3.5 hr. A 10% aqueous citric acid solution was added to the reaction mixture to stop the reaction, and the reaction mixture was extracted with ethyl acetate. The extract was washed with a saturated aqueous sodium bicarbonate solution and saturated brine in that order. The extract was then dried over anhydrous magnesium sulfate. The solvent was removed by evaporation, and the residue was purified by thin layer chromatography (developed with 10% methanol/methylene chloride) to give 0.16 g of a crude product of (3S,4R)-3-[(1R)-1-(tert-butyldimethylsilyloxy)ethyl]-4-[1-methyl-2-[7-(pyridin-3-yl)dimethylhydrazonoylimidazo[5,1-b]thiazol-2-yl]-2-oxoethyl]azetidin-2-one. This crude product was purified by Cosmosil 40C$_{18}$ reverse phase column chromatography (a 60% aqueous acetonitrile solution) to give 72.3 mg of (3S,4R)-3-[(1R)-1-(tert-butyldimethylsilyloxy)ethyl]-4-[(1R)-1-methyl-2-[7-(pyridin-3-yl)dimethylhydrazonoylimidazo[5,1-b]thiazol-2-yl]-2-oxoethyl]azetidin-2-one.

$^1$H-NMR (CDCl$_3$) δ: 0.07 (3H, s), 0.08 (3H, s), 0.88 (9H, s), 1.19 (3H, d, J=6.3 Hz), 1.38 (3H, d, J=7.1 Hz), 2.63 (6H, s), 2.96 (1H, dd, J=2.2, 4.4 Hz), 3.31-3.41 (1H, m), 4.01 (1H, dd, J=2.2, 4.9 Hz), 4.15-4.25 (1H, m), 6.12 (1H, s), 7.34 (1H, ddd, J=0.8, 4.9, 8.0 Hz), 7.99 (1H, ddd, J=2.2, 2.2, 8.0 Hz), 8.10 (1H, s), 8.25 (1H, s), 8.65 (1H, dd, J=2.2, 4.9 Hz), 8.88 (1H, dd, J=0.8, 2.2 Hz)

Example 18

(3S,4R)-3-[(1R)-1-(tert-Butyldimethylsilyloxy)ethyl]-4-[(1R)-1-methyl-2-[7-dimethoxy(pyridin-3-yl)methylimidazo[5,1-b]thiazol-2-yl]-2-oxoethyl]azetidin-2-one

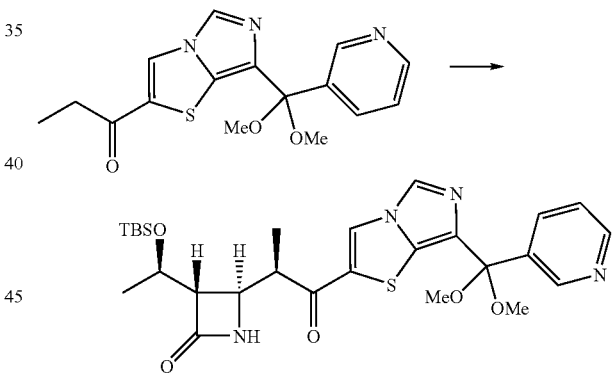

Tetrahydrofuran (4 ml) was added to 4.4 ml of a 1 M tetrahydrofuran solution of lithium bistrimethylsilylamide under an argon atmosphere, and the mixture was cooled to −78° C. A solution of 0.70 g of 7-dimethoxy(pyridin-3-yl)methyl-2-propionylimidazo[5,1-b]thiazole in 4 ml of tetrahydrofuran was added thereto, and the mixture was stirred at that temperature for 30 min. A solution of 0.69 g of (3S,4R)-4-acetoxy-3-[(1R)-1-tert-butyldimethylsilyloxyethyl]azetidin-2-one in 2.4 ml of tetrahydrofuran was added thereto, and the mixture was stirred at that temperature for 13 hr. A 10% aqueous citric acid solution was added to the reaction mixture to stop the reaction, and the reaction mixture was extracted with ethyl acetate. The extract was washed with a saturated aqueous sodium bicarbonate solution and saturated brine in that order and was then dried over anhydrous magnesium sulfate. The solvent was removed by evaporation, and the residue was purified by column chromatography on silica gel (7.5 to 12% methanol/ethyl acetate) to give 0.21 g of a crude product of (3S,4R)-3-[(1R)-1-(tert-butyldimethylsilyloxy)ethyl]-4-[1-methyl-2-[7-dimethoxy(pyridin-3-yl)methylimidazo[5,1-b]thiazol-2-yl]-2-oxoethyl]azetidin-2-one. This crude product was purified by Cosmosil 40C$_{18}$ reverse phase column chromatography (a 60% aqueous acetonitrile solution) to give 64.5 mg of (3S,4R)-3-[(1R)-1-(tert-butyldimethylsilyloxy)ethyl]-4-[(1R)-1-methyl-2-[7-dimethoxy(pyridin-3-yl)methylimidazo[5,1-b]thiazol-2-yl]-2-oxoethyl]azetidin-2-one.

$^1$H-NMR (CDCl$_3$) δ: 0.06 (3H, s), 0.08 (3H, s), 0.87 (9H, s), 1.17 (3H, d, J=6.3 Hz), 1.36 (3H, d, J=6.9 Hz), 2.94 (1H, dd, J=1.9, 4.1 Hz), 3.23 (6H, s), 3.30-3.39 (1H, m), 3.99 (1H, dd, J=1.9, 4.9 Hz), 4.15-4.23 (1H, m), 6.10 (1H, s), 7.35 (1H, dd, J=4.9, 8.0 Hz), 7.96-8.04 (1H, m), 8.01 (1H, s), 8.09 (1H, s), 8.54 (1H, dd, J=1.3, 4.9 Hz), 8.74 (1H, d, J=1.9 Hz)

Example 19

(3S,4R)-3-[(1R)-1-(tert-Butyldimethylsilyloxy)ethyl]-4-[(1R)-1-methyl-2-[7-(pyridin-3-yl)carbonylimidazo[5,1-b]thiazol-2-yl]-2-oxoethyl]azetidin-2-one

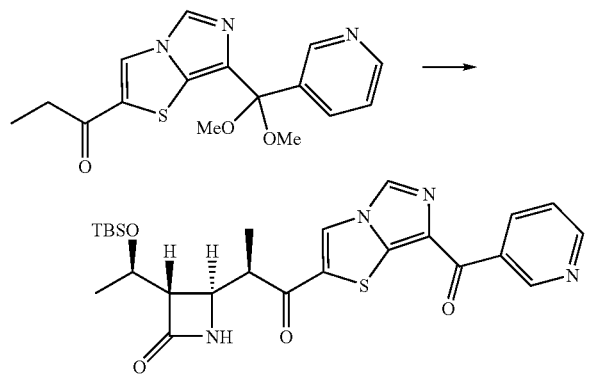

(a) (3S,4R)-3-[(1R)-1-(tert-Butyldimethylsilyloxy)ethyl]-4-[(1R)-1-methyl-2-[7-dimethoxy(pyridin-3-yl)methylimidazo[5,1-b]thiazol-2-yl]-2-oxoethyl]azetidin-2-one A 1 M tetrahydrofuran solution (11 ml) of lithium bistrimethylsilylamide was added to a solution of 0.64 g of lithium chloride in 10 ml of tetrahydrofuran under an argon atmosphere, and the mixture was cooled to −78° C. A solution of 1.66 g of 7-dimethoxy(pyridin-3-yl)methyl-2-propionylimidazo[5,1-b]thiazole in 5 ml of tetrahydrofuran was added thereto, and the mixture was stirred at that temperature for one hr. A solution of 1.72 g of (3S,4R)-4-acetoxy-3-[(1R)-1-tert-butyldimethylsilyloxyethyl]azetidin-2-one in 5 ml of tetrahydrofuran was added thereto, and the mixture was stirred at that temperature for 1.5 hr. The reaction mixture was added to a mixed liquid composed of 50 ml of a 10% aqueous citric acid solution and 25 ml of tetrahydrofuran cooled in an ice-water bath to stop the reaction, and the reaction mixture was extracted with ethyl acetate. The extract was washed with a 0.05 N aqueous hydrochloric acid solution, a saturated aqueous sodium bicarbonate solution and saturated brine in that order and was then dried over anhydrous sodium sulfate. The extract was concentrated by removing the solvent, and the concentrate was analyzed by HPLC (Cosmosil 5C$_{18}$-MS, 4.6×150 mm, a 70% aqueous acetonitrile solution). As a result, it was found that the yield of (3S,4R)-3-[(1R)-1-(tert-butyldimethylsilyloxy)ethyl]-4-[(1R)-1-methyl-2-[7-dimethoxymethyl(pyridin-3-yl)imidazo[5,1-b]thiazol-2-yl]-2-oxoethyl]azetidin-2-one was 1.17 g. An ethyl acetate: hexane=1:3 solution (20 ml) was added to the mixture, and the mixture was stirred. The precipitated solid was collected by filtration to give 1.00 g of (3S,4R)-3-[(1R)-1-(tert-butyldimethylsilyloxy)ethyl]-4-[(1R)-1-methyl-2-[7-dimethoxy(pyridin-3-yl)methylimidazo[5,1-b]thiazol-2-yl]-2-oxoethyl]azetidin-2-one. The solid was analyzed by NMR. The results were in agreement with the results of analysis in Example 18.

(b) (3S,4R)-3-[(1R)-1-(tert-Butyldimethylsilyloxy)ethyl]-4-[(1R)-1-methyl-2-[7-(pyridin-3-yl)carbonylimidazo[5,1-b]thiazol-2-yl]-2-oxoethyl]azetidin-2-one (3S,4R)-3-[(1R)-1-(tert-Butyldimethylsilyloxy)ethyl]-4-[(1R)-1-methyl-2-[7-dimethoxy(pyridin-3-yl)methylimidazo[5,1-b]thiazol-2-yl]-2-oxoethyl]azetidin-2-one (2.02 g) prepared in step (a) was dissolved in 40 ml of 1,4-dioxane at room temperature, and 40 ml of dimethyl sulfoxide and 6 ml of water were added in that order to the solution. The temperature of this solution was raised to 104° C., and the solution was stirred at that temperature for 2 days. After the completion of the reaction, the solution was cooled to room temperature, and dioxane was removed by evaporation under the reduced pressure. The residue was diluted with a mixed solution composed of ethyl acetate and tetrahydrofuran, 20% brine was then added thereto, and the reaction mixture was extracted with a mixed solution composed of ethyl acetate and tetrahydrofuran. The organic layer was washed with 20% brine and was then dried over magnesium sulfate. The solvent was removed by evaporation, and the residue was crystallized from butyl acetate-isopropylether-heptane to give 1.64 g of (3S,4R)-3-[(1R)-1-(tert-butyldimethylsilyloxy)ethyl]-4-[(1R)-1-methyl-2-[7-(pyridin-3-yl)carbonylimidazo[5,1-b]thiazol-2-yl]-2-oxoethyl]azetidin-2-one. This product was analyzed by NMR. The results were in agreement with the results of analysis in Example 16-(c).

Example 20

(3S,4R)-3-[(1R)-1-Hydroxyethyl]-4-[(1R)-1-methyl-2-[7-(pyridin-3-yl)carbonylimidazo[5,1-b]thiazol-2-yl]-2-oxoethyl]azetidin-2-one

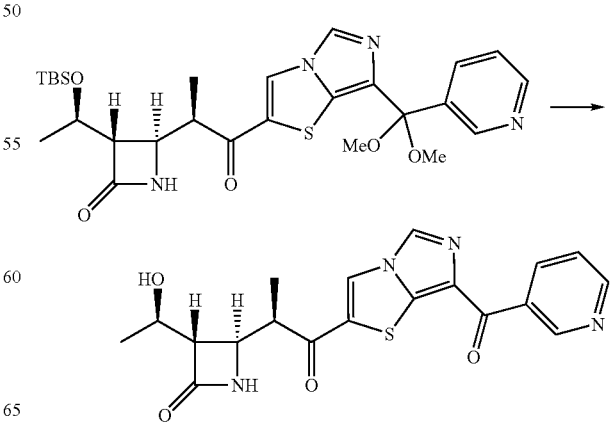

A 5 N aqueous hydrochloric acid solution (2 ml) was added to a solution of 0.56 g of (3S,4R)-3-[(1R)-1-(tert-butyldimethylsilyloxy)ethyl]-4-[(1R)-1-methyl-2-[7-dimethoxymethyl(pyridin-3-yl)imidazo[5,1-b]thiazol-2-yl]-2-oxoethyl]azetidin-2-one in 2 ml of methanol, and the mixture was stirred at 50° C. for one hr. The reaction mixture was diluted with water, and the diluted solution was extracted with methylene chloride. The organic layer was extracted with 10 ml of a 0.5 N aqueous hydrochloric acid solution. The aqueous layers were combined and were neutralized with a 5 N aqueous sodium hydroxide solution, and the resultant precipitate was collected by filtration to give 0.34 g of (3S,4R)-3-[(1R)-1-hydroxyethyl]-4-[(1R)-1-methyl-2-[7-(pyridin-3-yl)carbonylimidazo[5,1-b]thiazol-2-yl]-2-oxoethyl]azetidin-2-one.

$^1$H-NMR (DMSO-$d_6$) δ: 0.95 (3H, d, J=6.3 Hz), 1.23 (3H, d, J=6.6 Hz), 2.89 (1H, dd, J=1.6, 5.2 Hz), 3.61-3.82 (3H, m), 4.74 (1H, d, J=5.2 Hz), 7.62 (1H, dd, J=4.9, 8.0 Hz), 8.24 (1H, s), 8.64 (1H, s), 8.72 (1H, ddd, J=1.9, 1.9, 8.0 Hz), 8.80 (1H, dd, J=1.9, 4.9 Hz), 9.37 (1H, s), 9.57 (1H, d, J=1.9 Hz)

Example 21

(3S,4R)-3-[(1R)-1-(Triethylsilyloxy)ethyl]-4-[(1R)-1-methyl-2-[7-(pyridin-3-yl)carbonylimidazo[5,1-b]thiazol-2-yl]-2-oxoethyl]azetidin-2-one

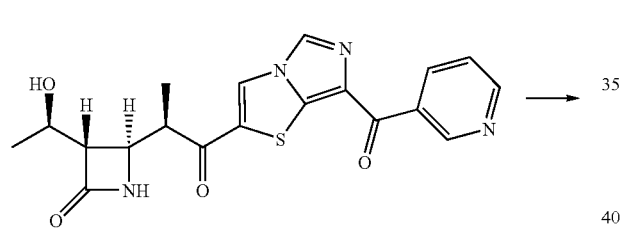

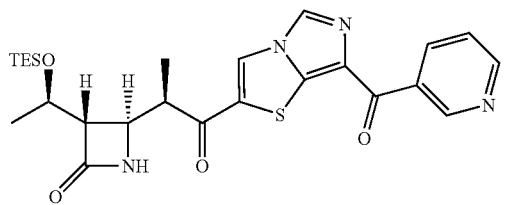

Imidazole (0.15 g) and 0.36 ml of triethylsilylchloride were added to a solution of 0.32 g of (3S,4R)-3-[(1R)-1-hydroxyethyl]-4-[(1R)-1-methyl-2-[7-(pyridin-3-yl)carbonylimidazo[5,1-b]thiazol-2-yl]-2-oxoethyl]azetidin-2-one in 3.2 ml of dimethylformamide under ice cooling, and the mixture was stirred at room temperature for 2 hr. The reaction mixture was diluted with 80 ml of ethyl acetate, and the diluted reaction mixture was washed three times with 20 ml of a 10% aqueous sodium chloride solution and was then washed with an a saturated aqueous sodium chloride solution and was dried over anhydrous magnesium sulfate. The solvent was removed by evaporation, the resultant solid was suspended in 4 ml of a hexane:ethyl acetate=1:1 solution and was collected by filtration to give 0.33 g of (3S,4R)-3-[(1R)-1-(triethylsilyloxy)ethyl]-4-[(1R)-1-methyl-2-[7-(pyridin-3-yl)carbonylimidazo[5,1-b]thiazol-2-yl]-2-oxoethyl]azetidin-2-one.

$^1$H-NMR (CDCl$_3$) δ: 0.60 (6H, q, J=7.7 Hz), 0.94 (9H, t, J=7.7 Hz), 1.20 (3H, d, J=6.3 Hz), 1.40 (3H, d, J=7.1 Hz), 2.93 (1H, dd, J=1.9, 5.2 Hz), 3.35-3.45 (1H, m), 4.00 (1H, dd, J=2.2, 4.7 Hz), 4.14-4.22 (1H, m), 6.14 (1H, s), 7.44-7.50 (1H, m), 8.20 (1H, s), 8.28 (1H, s), 8.27-8.33 (2H, m), 9.75 (1H, m)

Example 22

(3S,4R)-3-[(1R)-1-(tert-Butyldimethylsilyloxy)ethyl]-4-[(1R)-1-methyl-2-[7-dimethoxymethyl(pyridin-3-yl)imidazo[5,1-b]thiazol-2-yl]-2-oxoethyl]azetidin-2-one

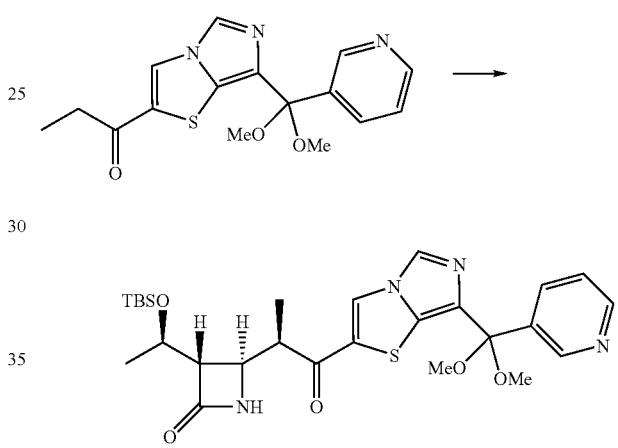

Methylene chloride (2 ml) was added to 0.69 g of tin(II) trifluoromethanesulfonate under an argon atmosphere, and the mixture was cooled to −20° C. A solution of 0.25 g of 2-propionyl-7-(pyridin-3-yl)dimethoxymethylimidazo[5,1-b]thiazole in 1.5 ml of methylene chloride and 0.12 ml of N-ethylpiperidine were added thereto, and the mixture was stirred for 2 hr. A solution of 0.14 g of (3S,4R)-4-acetoxy-3-[(1R)-1-tert-butyldimethylsilyloxyethyl]azetidin-2-one in 1 ml of methylene chloride was added at 0° C., and the mixture was stirred at room temperature for one hr. A saturated aqueous sodium bicarbonate solution was added to the reaction mixture to stop the reaction, and the reaction mixture was extracted with ethyl acetate. The organic layer was washed with a 5% aqueous sodium bicarbonate solution and a 20% aqueous sodium chloride solution in that order and was dried over anhydrous magnesium sulfate. The solvent was removed by evaporation, and the residue was analyzed by HPLC (Cosmosil 5C$_{18}$-MS, 4.6×150 mm, a 70% aqueous acetonitrile solution). As a result, it was found that the yield of (3S,4R)-3-[(1R)-1-(tert-butyldimethylsilyloxy)ethyl]-4-[(1R)-1-methyl-2-[7-dimethoxy(pyridin-3-yl)methylimidazo[5,1-b]thiazol-2-yl]-2-oxoethyl]azetidin-2-one was 45 mg. The results of analysis by NMR were in agreement with the results of analysis in Example 18.

Example 23

(3S,4R)-1-Allyloxyoxalyl-3-[(1R)-1-(tert-butyldimethylsilyloxy)ethyl]-4-[(1R)-1-methyl-2-[7-(pyridin-3-yl)carbonylimidazo[5,1-b]thiazol-2-yl]-2-oxoethyl]azetidin-2-one

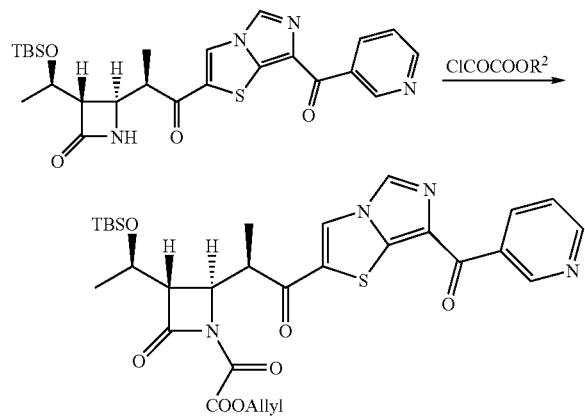

Diisopropylethylamine (0.45 ml) and 0.32 ml of allyloxyoxalyl chloride were added in that order under an argon atmosphere to a solution of 0.66 g of (3S,4R)-3-[(1R)-1-(tert-butyldimethylsilyloxy)ethyl]-4-[(1R)-1-methyl-2-[7-(pyridin-3-yl)carbonylimidazo[5,1-b]thiazol-2-yl]-2-oxoethyl]azetidin-2-one in 6.4 ml of methylene chloride, and the mixture was stirred at room temperature for 10 min. The reaction mixture was diluted with ethyl acetate, and the diluted reaction mixture was washed with a saturated aqueous sodium bicarbonate solution and saturated brine in that order and was then dried over anhydrous magnesium sulfate. The solvent was removed by evaporation, and the resultant solid was washed with ethyl acetate to give 0.57 g of (3S,4R)-1-allyloxyoxalyl-3-[(1R)-1-(tert-butyldimethylsilyloxy)ethyl]-4-[(1R)-1-methyl-2-[7-(pyridine-3-yl)carbonylimidazo[5,1-b]thiazol-2-yl]-2-oxoethyl]azetidin-2-one.

$^1$H-NMR (CDCl$_3$) δ: 0.02 (3H, s), 0.08 (3H, s), 0.85 (9H, s), 1.25 (3H, d, J=6.3 Hz), 1.38 (3H, d, J=7.1 Hz), 3.71 (1H, dd, J=3.0, 3.0 Hz), 4.20-4.30 (1H, m), 4.30-4.40 (1H, m), 4.50-4.55 (1H, m), 4.57-4.63 (2H, m), 5.15-5.24 (2H, m), 5.65-5.79 (1H, m), 7.44-7.48 (1H, m), 8.18 (1H, s), 8.21 (1H, s), 8.78-8.82 (2H, m), 9.73-9.75 (1H, m)

Example 24

Allyl (1S,5R,6S)-6-[(1R)-1-(t-butyldimethylsilyloxy)ethyl]-2-[7-(pyridin-3-yl)carbonylimidazo[5,1-b]thiazol-2-yl]-1-methylcarbapen-2-em-3-carboxylate

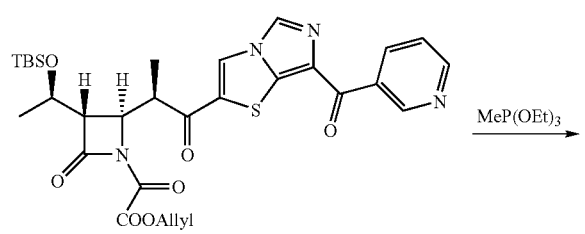

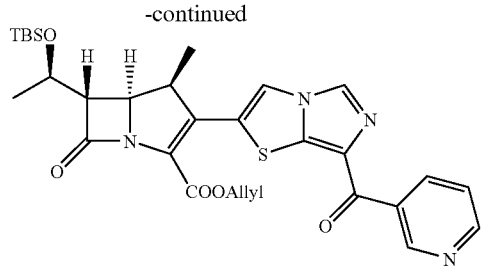

A 30% hexane solution (0.19 ml) of diethyl methylphosphonite was added to a solution of 62.4 mg of (3S,4R)-1-allyloxyoxalyl-3-[(1R)-1-(tert-butyldimethylsilyloxy)ethyl]-4-[(1R)-1-methyl-2-[7-(pyridin-3-yl)carbonylimidazo[5,1-b]thiazol-2-yl]-2-oxoethyl]azetidin-2-one in 1 ml of tetrahydrofuran under an argon atmosphere, and the mixture was stirred at room temperature for one hr and was then stirred at 40 to 50° C. for 1.5 hr. Isopropyl alcohol (1 ml) was added to the reaction mixture, and the solvent was removed by evaporation, followed by repetition of this procedure three times. Thereafter, 2 ml of isopropyl alcohol was added thereto, and the mixture was stirred at 60° C. for one hr. The solvent was removed by evaporation, and the residue was purified by thin layer chromatography (developed with ethyl acetate) to give 33.6 mg of allyl (1S,5R,6S)-6-[(1R)-1-(t-butyldimethylsilyloxy)ethyl]-2-[7-(pyridin-3-yl)carbonylimidazo[5,1-b]thiazol-2-yl]-1-methylcarbapen-2-em-3-carboxylate.

$^1$H-NMR (CDCl$_3$) δ: 0.10 (3H, s), 0.11 (3H, s), 0.91 (9H, s), 1.27 (3H, d, J=5.8 Hz), 1.29 (3H, d, J=6.6 Hz), 3.33 (1H, dd, J=2.7, 5.2 Hz), 3.42-3.52 (1H, m), 4.26-4.36 (1H, m), 4.39 (1H, dd, J=2.7, 9.9 Hz), 4.70-4.86 (2H, m), 5.27-5.49 (2H, m), 5.91-6.03 (1H, m), 7.45 (1H, dd, J=4.7, 7.7 Hz), 8.10 (1H, s), 8.61 (1H, s), 8.77-8.85 (2H, m), 9.71 (1H, m)

Example 25

(3S,4R)-1-Allyloxyoxalyl-3-[(1R)-1-hydroxyethyl)-4-[(1R)-1-methyl-2-[7-(pyridin-3-yl)carbonylimidazo[5,1-b]thiazol-2-yl]-2-oxoethyl]azetidin-2-one

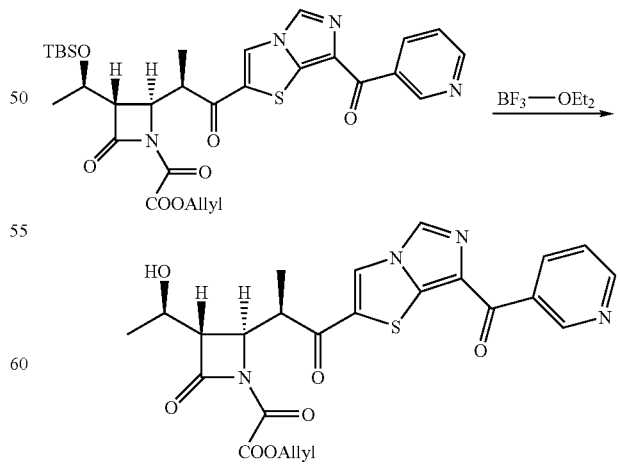

A boron trifluoride diethyl ether complex (0.59 ml) was added to a suspension of 0.59 g of (3S,4R)-1-allyloxyoxalyl- 3-[(1R)-1-(tert-butyldimethylsilyloxy)ethyl]-4-[(1R)-1-methyl-2-[7-(pyridin-3-yl)carbonylimidazo[5,1-b]thiazol-2-yl]-2-oxoethyl]azetidin-2-one in 5 ml of acetonitrile under an argon atmosphere, and the mixture was stirred at room temperature for 22 hr. The reaction mixture was added to a mixed liquid composed of ethyl acetate and a dilute aqueous sodium bicarbonate solution with stirring to stop the reaction, and the organic layer was separated. The organic layer was washed with a saturated aqueous sodium bicarbonate solution and saturated brine in that order. The solvent was removed by evaporation to give 0.51 g of (3S,4R)-1-allyloxyoxalyl-3-[(1R)-1-hydroxyethyl]-4-[(1R)-1-methyl-2-[7-(pyridin-3-yl)carbonylimidazo[5,1-b]thiazol-2-yl]-2-oxoethyl]azetidin-2-one.

$^1$H-NMR (CDCl$_3$) δ: 1.37 (3H, d, J=6.3 Hz), 1.42 (3H, d, J=7.1 Hz), 3.74 (1H, d, J=3.3, 5.2 Hz), 4.19-4.35 (2H, m), 4.49-4.52 (1H, m), 4.62-4.64 (2H, m), 5.21-5.30 (2H, m), 5.69-5.82 (1H, m), 7.45-7.50 (1H, m), 8.17 (1H, s), 8.28 (1H, s), 8.78-8.82 (2H, m), 8.73-8.74 (1H, m)

Example 26

Allyl (1S,5R,6S)-6-[(1R)-1-hydroxyethyl]-2-[7-(pyridin-3-yl)carbonylimidazo[5,1-b]thiazol-2-yl]-1-methylcarbapen-2-em-3-carboxylate

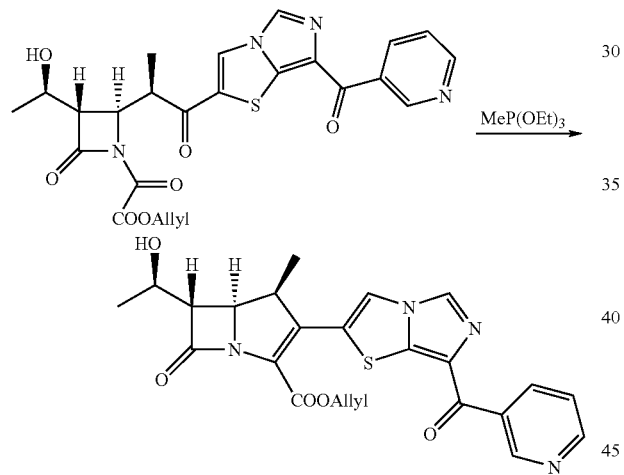

A 30% hexane solution (0.19 ml) of diethyl methylphosphonite was added to a solution of 51 mg of (3S,4R)-1-allyloxyoxalyl-3-[(1R)-1-hydroxyethyl]-4-[(1R)-1-methyl-2-[7-(pyridin-3-yl)carbonylimidazo[5,1-b]thiazol-2-yl]-2-oxoethyl]azetidin-2-one in 1 ml of tetrahydrofuran under an argon atmosphere, and the mixture was stirred at room temperature for 2.5 hr. Isopropyl alcohol (1 ml) was added to the reaction mixture, and the solvent was removed by evaporation, followed by repetition of this procedure three times. Thereafter, 2 ml of isopropyl alcohol was added thereto, and the mixture was heated under reflux for 2 hr. The solvent was removed by evaporation, and the residue was purified by thin layer chromatography (developed with 10% methanol/methylene chloride) to give 26.6 mg of allyl (1S,5R,6S)-6-[(1R)-1-hydroxyethyl]-2-[7-(pyridin-3-yl)carbonylimidazo[5,1-b]thiazol-2-yl]-1-methylcarbapen-2-em-3-carboxylate.

$^1$H-NMR (CDCl$_3$) δ: 1.32 (3H, d, J=7.1 Hz), 1.40 (3H, d, J=6.3 Hz), 3.38 (1H, dd, J=2.7, 6.9 Hz), 3.52-3.60 (1H, m), 4.26-4.35 (1H, m), 4.40 (1H, dd, J=2.7, 9.6 Hz), 4.71-4.91 (2H, m), 5.28-5.50 (2H, m), 5.92-6.05 (1H, m), 7.44-7.49 (1H, m), 8.11 (1H, s), 8.61 (1H, s), 8.78 (1H, dd, J=1.6, 4.7 Hz), 8.84 (1H, ddd, J=1.9, 1.9, 8.0 Hz), 9.70-9.71 (1H, m)

Example 27

(3S,4R)-3-[(1R)-1-(t-Butyldimethylsilyloxy)ethyl]-4-{(1R)-1-methyl-2-[7-(pyridin-3-yl)carbonylimidazo[5,1-b]thiazol-2-yl]-2-oxoethyl}-1-[4-nitrobenzyloxycarbonyl(triphenylphosphoranylidene)methyl]azetidin-2-one

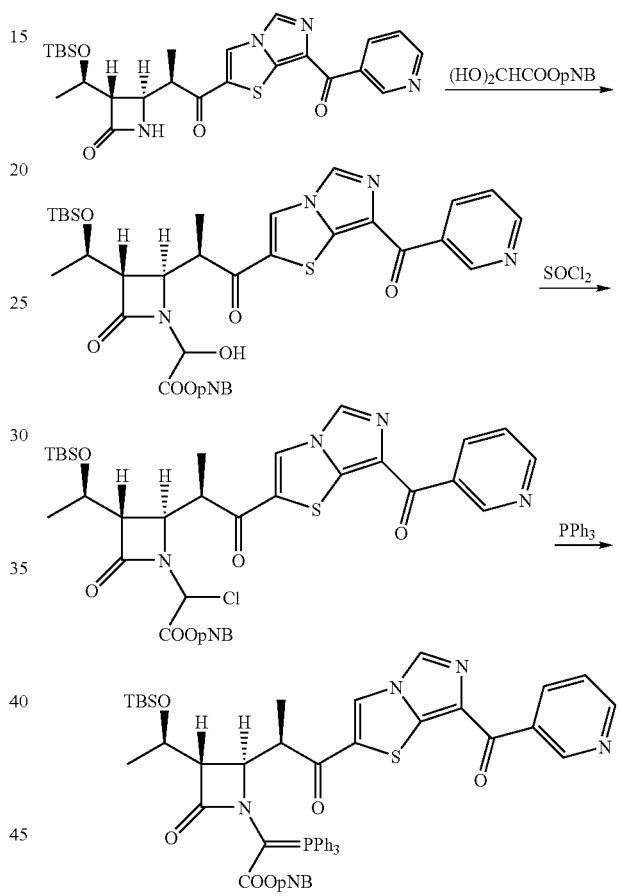

(a) (3S,4R)-3-[(1R)-1-(t-Butyldimethylsilyloxy)ethyl-4-{(1R)-1-methyl-2-[7-(pyridin-3-yl)carbonylimidazo[5,1-b]thiazol-2-yl]-2-oxoethyl}-1-[[(4-nitrobenzyloxy)carbonyl]hydroxymethyl]]azetidin-2-one 4-Nitrobenzyl glyoxylate monohydrate (0.14 g) was added to a solution of 0.26 g of (3S,4R)-3-[(1R)-1-(t-butyldimethylsilyloxy)ethyl]-4-[(1R)-1-methyl-2-[7-(pyridin-3-yl)carbonylimidazo[5,1-b]thiazol-2-yl]-2-oxoethyl]azetidin-2-one in 15 ml of toluene, and the mixture was heated under reflux for 1.5 hr. The insolubles were removed, and the solvent was removed by evaporation to give 0.23 g of a crude product of (3S,4R)-3-[(1R)-1-(t-butyldimethylsilyloxy)ethyl]-4-{(1R)-1-methyl-2-[7-(pyridin-3-yl)carbonylimidazo[5,1-b]thiazol-2-yl]-2-oxoethyl}-1-[[(4-nitrobenzyloxy)carbonyl]hydroxymethyl]azetidin-2-one.

(b) (3S,4R)-3-[(1R)-1-(t-Butyldimethylsilyloxy) ethyl]-4-{(1R)-1-methyl-2-[7-(pyridin-3-yl)carbonylimidazo[5,1-b]thiazol-2-yl]-2-oxoethyl}-1-[4-nitrobenzyloxycarbonyl(triphenylphosphoranylidene) methyl]azetidin-2-one Pyridine (0.1 ml) was added to a solution of 0.23 g of the crude product of (3S,4R)-3-[(1R)-1-(t-butyldimethylsilyloxy)ethyl]-4-{(1R)-1-methyl-2-[7-(pyridin-3-yl)carbonylimidazo[5,1-b]thiazol-2-yl]-2-oxoethyl}-1-[[(4-nitrobenzyloxy)carbonyl]hydroxymethyl]azetidin-2-one in 2 ml of tetrahydrofuran under an argon atmosphere, and the mixture was cooled to −20° C. Thionyl chloride (0.09 ml) was added thereto, and the mixture was stirred at that temperature for one hr. The reaction mixture was diluted with ethyl acetate, and the diluted reaction mixture was washed with water and saturated brine and was then dried over anhydrous magnesium sulfate. The solvent was removed by evaporation to give a crude product of (3S,4R)-3-[(1R)-1-(t-butyldimethylsilyloxy)ethyl]-4-{(1R)-1-methyl-2-[7-(pyridin-3-yl)carbonylimidazo[5,1-b]thiazol-2-yl]-2-oxoethyl}-1-[[(4-nitrobenzyloxy)carbonyl]chloromethyl]azetidin-2-one. Triphenylphosphine (0.26 g) and 0.05 g of potassium iodide were added to a solution of this crude product in 2 ml of dimethylformamide, and the mixture was stirred at 60° C. for one hr. The reaction mixture was diluted with ethyl acetate, and the diluted reaction mixture was washed with water and saturated brine and was then dried over anhydrous magnesium sulfate. The solvent was removed by evaporation, and the residue was purified by thin layer chromatography (developed with 10% methanol/ethyl acetate) to give 0.19 g of (3S,4R)-3-[(1R)-1-(t-butyldimethylsilyloxy)ethyl]-4-{(1R)-1-methyl-2-[7-(pyridin-3-yl)carbonylimidazo[5,1-b]thiazol-2-yl]-2-oxoethyl}-1-[4-nitrobenzyloxycarbonyl(triphenylphosphoranylidene)methyl]azetidin-2-one.

$^1$H-NMR (CDCl$_3$) δ: −0.90-0.00 (6H, m), 0.75-0.85 (9H, m), 0.90-1.00 (3H, m), 1.40-1.60 (3H, m), 2.60-2.70 (2H, m), 2.70-2.90 (2H, m), 4.80-4.95 (2H, m), 6.65-6.75 (2H, m), 7.4-7.9 (18H, m), 8.15-8.25 (1H, m), 8.70-8.95 (3H, m), 9.70-9.80 (1H, m)

Example 28

(4-Nitrobenzyl) (1S,5R,6S)-6-[(1R)-1-(t-butyldimethylsilyloxy)ethyl]-2-[7-(pyridin-3-yl)carbonylimidazo[5,1-b]thiazol-2-yl]-1-methylcarbapen-2-em-3-carboxylate

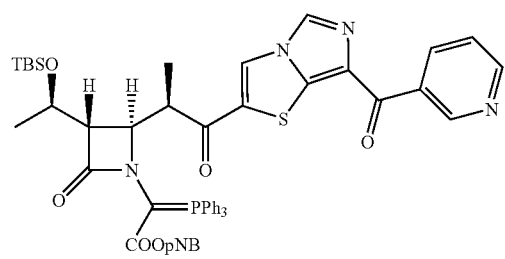

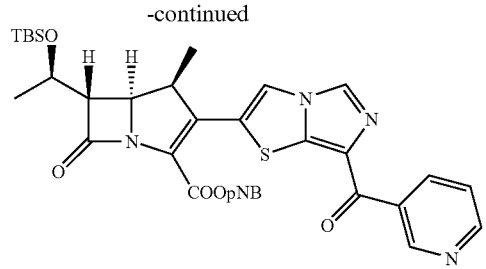

A solution of 54.6 mg of (3S,4R)-3-[(1R)-1-(t-butyldimethylsilyloxy)ethyl]-4-{(1R)-1-methyl-2-[7-(pyridin-3-yl)carbonylimidazo[5,1-b]thiazol-2-yl]-2-oxoethyl}-1-[4-nitrobenzyloxycarbonyl(triphenylphosphoranylidene)methyl]azetidin-2-one in 2 ml of toluene was heated under reflux for 2.5 hr. The solvent was removed by evaporation, and the residue was purified by thin layer chromatography (developed with 5% methanol/ethyl acetate) to give 28.3 mg of (4-nitrobenzyl) (1S,5R,6S)-6-[(1R)-1-(t-butyldimethylsilyloxy)ethyl]-2-[7-(pyridin-3-yl)carbonylimidazo[5,1-b]thiazol-2-yl]-1-methylcarbapen-2-em-3-carboxylate.

$^1$H-NMR (CDCl$_3$) δ: 0.09 (3H, s), 0.11 (3H, m), 0.87 (9H, s), 1.28 (3H, d, J=6.3 Hz), 1.31 (3H, d, J=7.1 Hz), 3.36 (1H, dd, J=4.7, 7.7 Hz), 3.45-3.58 (1H, m), 4.28-4.38 (1H, m), 4.4 (1H, dd, J=3.0, 9.9 Hz), 5.28 (1H, d, J=13.7 Hz), 5.50 (1H, d, J=13.7 Hz), 7.43-7.49 (1H, m), 7.68 (2H, d, J=8.8 Hz), 8.10 (1H, s), 8.24 (2H, d, J=8.8 Hz), 8.58 (1H, s), 8.78 (1H, dd, J=1.6, 4.9 Hz), 8.83 (1H, ddd, J=1.6, 1.6, 8.0 Hz), 9.71 (1H, dd, J=0.8, 1.6 Hz)

Example 29

(3S,4R)-3-[(1R)-1-Hydroxyethyl]-4-{(1R)-1-methyl-2-[7-(pyridin-3-yl)carbonylimidazo[5,1-b]thiazol-2-yl]-2-oxoethyl}-1-[4-nitrobenzyloxycarbonyl(triphenylphosphoranylidene)methyl]azetidin-2-one

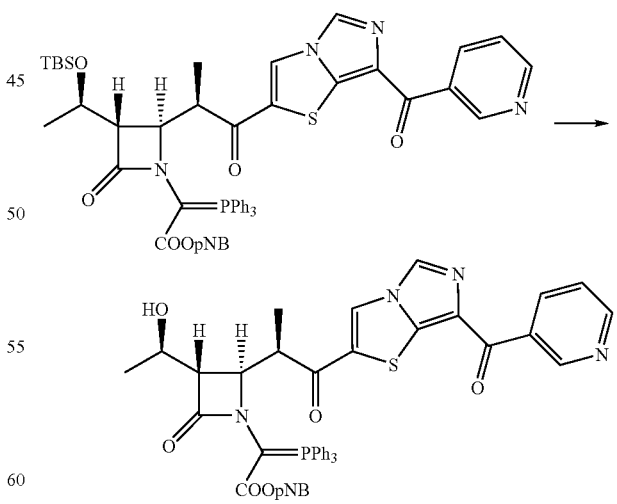

A 5 N aqueous hydrochloric acid solution (1 ml) was added to a solution of 72.4 mg of (3S,4R)-3-[(1R)-1-(t-butyldimethylsilyloxy)ethyl]-4-{(1R)-1-methyl-2-[7-(pyridin-3-yl)carbonylimidazo[5,1-b]thiazol-2-yl]-2-oxoethyl}-1-[4-nitrobenzyloxycarbonyl(triphenylphosphoranylidene)- methyl]azetidin-2-one in 2 ml of methanol, and the mixture was stirred at room temperature for 2 hr. The reaction mixture was neutralized with saturated aqueous sodium bicarbonate solution and was extracted with ethyl acetate. The organic layer was washed with saturated brine and was dried over anhydrous magnesium sulfate. The solvent was removed by evaporation, and the residue was purified by thin layer chromatography (developed with 10% methanol/methylene chloride) to give 46.9 mg of (3S,4R)-3-[(1R)-1-hydroxyethyl]-4-{(1R)-1-methyl-2-[7-(pyridin-3-yl)carbonylimidazo[5,1-b]thiazol-2-yl]-2-oxoethyl}-1-[4-nitrobenzyloxycarbonyl(triphenyl phosphoranylidene)methyl]azetidin-2-one.

$^1$H-NMR (CDCl$_3$) δ: 0.9-1.0 (3H, m), 1.5-1.7 (3H, m), 2.3-3.1 (3H, m), 3.60-3.70, 4.0-4.2 (1H, m), 4.7-5.0, 5.1-5.4 (2H, m), 6.69 (2H, d, J=6.8 Hz), 7.4-7.8 (18H, m), 8.13-8.27 (2H, m), 8.78 (2H, m), 9.71 (1H, s).

Example 30

(4-Nitrobenzyl) (1S,5R,6S)-6-[(1R)-1-hydroxyethyl]-2-[7-(pyridin-3-yl)carbonylimidazo[5,1-b]thiazol-2-yl]-1-methylcarbapen-2-em-3-carboxylate

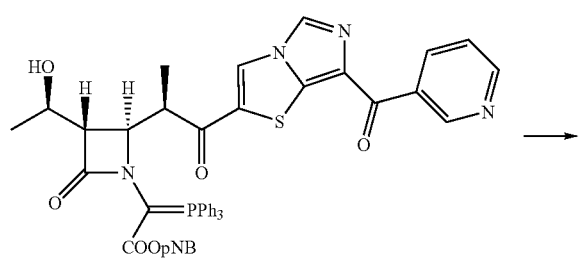

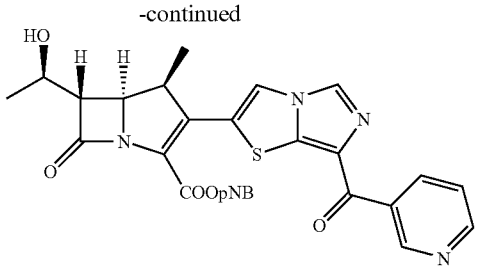

A solution of 46.9 mg of (3S,4R)-3-[(1R)-1-hydroxyethyl]-4-{(1R)-1-methyl-2-[7-(pyridin-3-yl)carbonylimidazo[5,1-b]thiazol-2-yl]-2-oxoethyl}-1-[4-nitrobenzyloxycarbonyl(triphenylphosphoranylidene)-methyl]azetidin-2-one in 1 ml of toluene was heated under reflux for 3 hr. The solvent was removed by evaporation, and the residue was purified by thin layer chromatography (developed with 10% methanol/methylene chloride) to give 23.1 mg of (4-nitrobenzyl) (1S,5R,6S)-6-[(1R)-1-hydroxyethyl]-2-[7-(pyridin-3-yl)carbonylimidazo[5,1-b]thiazol-2-yl]-1-methylcarbapen-2-em-3-carboxylate.

$^1$H-NMR (CDCl$_3$) δ: 1.33 (3H, d, J=7.3 Hz), 1.41 (3H, d, J=6.1 Hz), 3.43 (1H, dd, J=3.0, 6.4 Hz), 3.60 (1H, m), 4.35 (1H, m), 4.49 (1H, dd, J=2.9, 9.7 Hz), 5.22 (1H, d, J=13.9 Hz), 5.50 (1H, d, J=13.6 Hz), 7.46 (1H, ddd, J=0.7, 4.9, 8.1 Hz), 7.67 (2H, d, J=8.8 Hz), 8.11 (1H, s), 8.17 (2H, d, J=8.8 Hz), 8.53 (1H, s), 8.76 (1H, dd, J=1.7, 4.8 Hz), 8.84 (1H, dt, J=2.0, 7.9 Hz), 9.69 (1H, dd, J=0.7, 2.2 Hz)

Example 31

(3S,4R)-1-[Allyloxycarbonyl(triphenylphosphoranylidene)-methyl]-3-[(1R)-1-(t-butyldimethylsilyloxy)ethyl]-4-{(1R)-1-methyl-2-[7-(pyridin-3-yl)triethylsilyloxymethylimidazo[5,1-b]thiazol-2-yl]-2-oxoethyl}azetidin-2-one

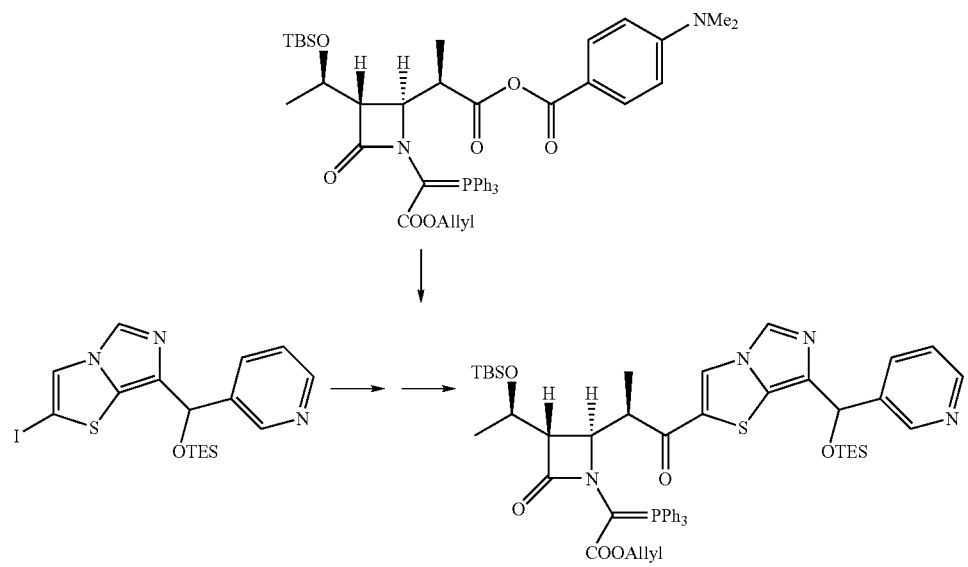

A solution of 0.12 g of 2-iodo-7-triethylsilyloxy(pyridin-3-yl)methylimidazo[5,1-b]thiazole in 2 ml of tetrahydrofuran was cooled to −60° C., 0.31 ml of a 0.89 M tetrahydrofuran solution of ethylmagnesium bromide was added thereto, and the mixture was stirred at that temperature for one hr. A solution of 0.23 g of (3S,4R)-1-[allyloxycarbonyl(triphenylphosphoranylidene)methyl]-3-[(1R)-1-(t-butyldimethylsilyloxy)ethyl]-4-[(1R)-1-(4-dimethylaminobenzoyl-oxycarbonyl)ethyl]azetidin-2-one in 0.7 ml of tetrahydrofuran was added to the reaction mixture, and the mixture was stirred at room temperature for 3 hr. The reaction mixture was added to a 20% aqueous ammonium chloride solution, and the mixture was extracted twice with 20 ml of ethyl acetate. The organic layers were combined and were washed with a mixed liquid composed of 2 ml of 1 N hydrochloric acid and 18 ml of 20% brine, a 5% aqueous sodium bicarbonate solution (20 ml) and 20% brine (20 ml) in that order and was then dried over anhydrous magnesium sulfate. The solvent was removed by evaporation, and the residue was purified by chromatography on silica gel (methylene chloride:methanol=20:1) to give 94 mg of (3S,4R)-1-[allyloxycarbonyl(triphenylphosphoranylidene)methyl]-3-[(1R)-1-(t-butyldimethylsilyloxy)ethyl]-4-{(1R)-1-methyl-[7-(pyridin-3-yl)triethylsilyloxymethylimidazo[5,1-b]thiazol-2-yl]-2-oxoethyl}azetidin-2-one.

$^1$H-NMR (CDCl$_3$) δ: −0.03 (3H, s), −0.02 (3H, s), 0.68 (6H, m), 0.85 (9H, 2s), 0.94 (13H, m), 1.55 (3H, m), 2.63-2.87 (2H, m), 3.80-3.99 (1H, m), 4.24 (1H, m), 4.62-4.74 (2H, m), 5.19-5.27 (2H, m), 6.03 (1H, m), 7.29 (1H, m), 7.56-7.86 (16H, m), 8.03 (1H, m), 8.55 (1H, m), 8.78 (1H, m). MS (FAB$^+$) m/z 987 (M$^+$)

Example 32

Allyl (1S,5R,6S)-6-[(1R)-1-hydroxyethyl]-2-[7-(pyridin-3-yl)carbonylimidazo[5,1-b]thiazol-2-yl]-1-methylcarbapen-2-em-3-carboxylate

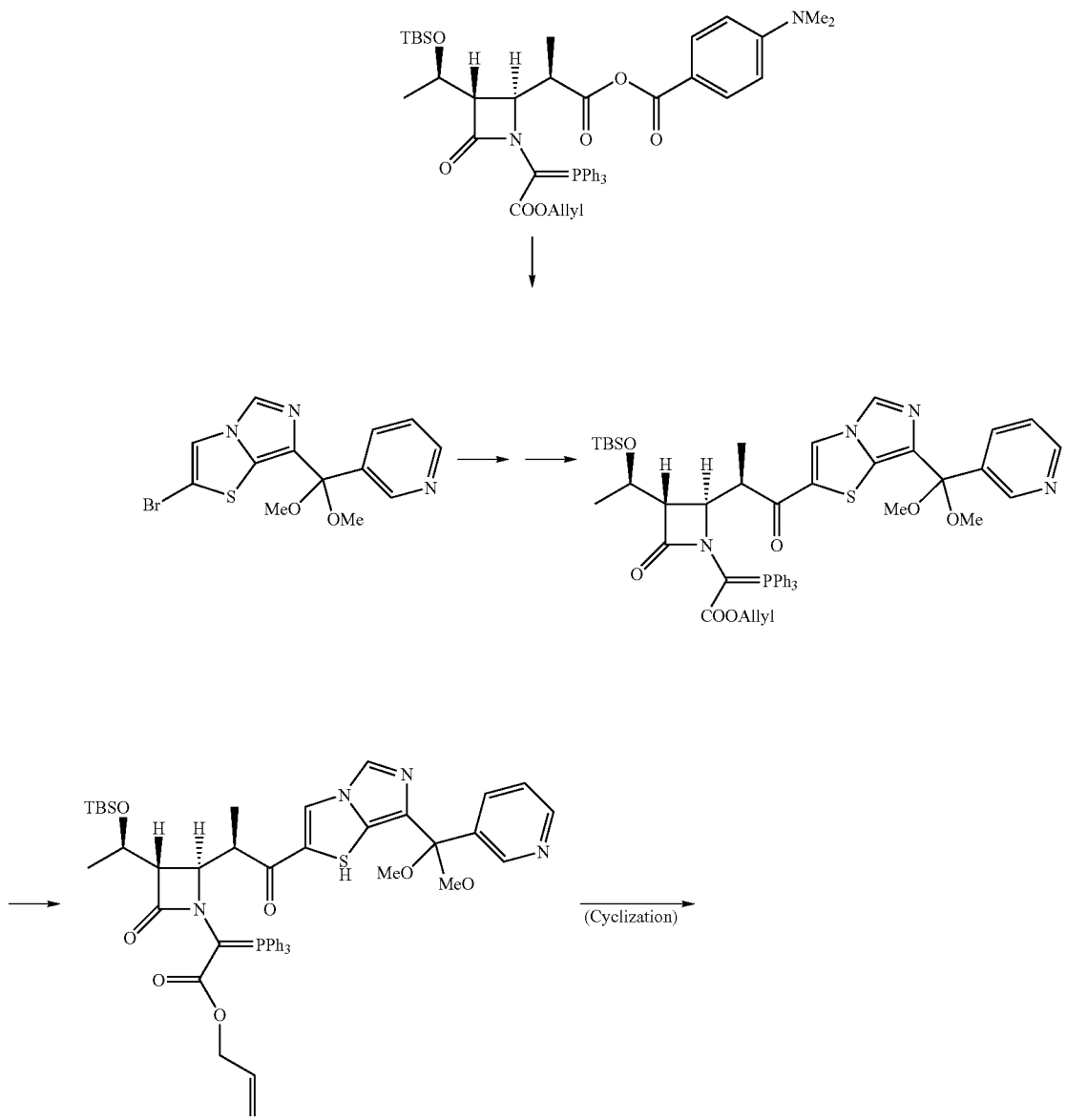

-continued

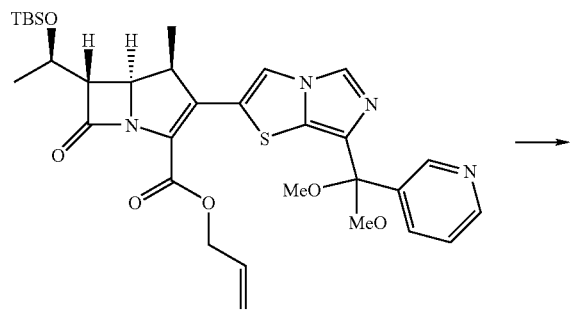

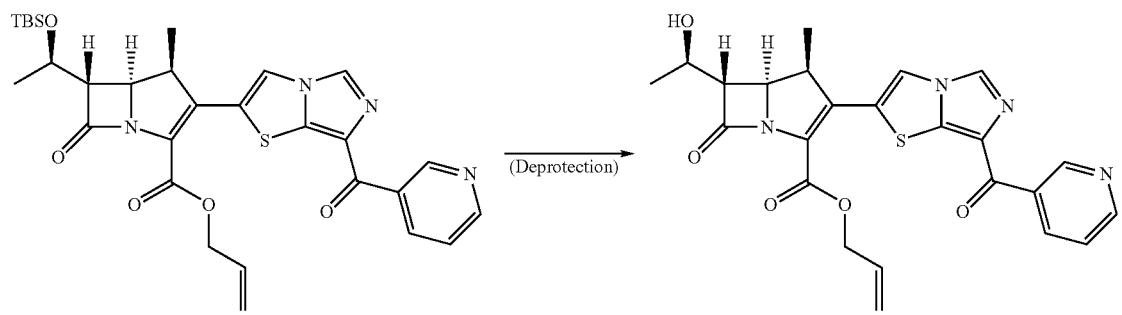

(a) (3S,4R)-1-[Allyloxycarbonyl(triphenylphosphoranylidene)-methyl]-3-[(1R)-1-(t-butyldimethylsilyloxy)ethyl]-4-{(1R)-1-methyl-2-[7-dimethoxy(pyridin-3-yl)methylimidazo[5,1-b]thiazol-2-yl]-2-oxoethyl}azetidin-2-one A solution of 0.24 g of 2-bromo-7-dimethoxy(pyridin-3-yl)methylimidazo[5,1-b]thiazole in tetrahydrofuran (2 ml) was cooled to −60° C., 0.84 ml of a 0.89 M tetrahydrofuran solution of ethylmagnesium bromide was added thereto, and the mixture was stirred at that temperature for one hr. A solution of 0.60 g of (3S,4R)-1-[allyloxycarbonyl(triphenylphosphoranylidene)methyl]-3-[(1R)-1-(t-butyldimethylsilyloxy)ethyl]-4-[(1R)-1-(4-dimethylaminobenzoyl-oxycarbonyl)ethyl]azetidin-2-one in 1 ml of tetrahydrofuran was added to the reaction mixture, and the mixture was stirred at room temperature for 4 hr. The reaction mixture was added to a 20% aqueous ammonium chloride solution, and the mixture was extracted twice with ethyl acetate (20 ml). The organic layers were combined, were washed with 10% brine (20 ml), and was dried over anhydrous magnesium sulfate. The solvent was removed by evaporation, and the residue was purified by chromatography on silica gel (methylene chloride:methanol=20:1) to give 0.37 g of (3S,4R)-1-[allyloxycarbonyl(triphenylphosphoranylidene)methyl]-3-[(1R)-1-(t-butyldimethylsilyloxy)ethyl]-4-{(1R)-1-methyl-2-[7-dimethoxy(pyridin-3-yl)methylimidazo[5,1-b]thiazol-2-yl]-2-oxoethyl}azetidin-2-one.

$^1$H-NMR (CDCl$^3$) δ: −0.06 (3H, s), −0.05 (3H, s), 0.81 (9H, s), 0.90 (3H, 2s), 1.49 (3H, m), 2.39 (1H, m), 2.64-2.86 (1H, m), 3.21 (3H, 2s), 3.76-4.04 (1H, m), 4.18 (1H, m), 4.59 (1H, m), 4.67 (1H, m), 5.12-5.43 (2H, m), 6.04 (1H, m), 7.26 (1H, m), 7.52-7.81 (15H, m), 7.90 (1H, m), 7.95-8.04 (2H, m), 8.51 (1H, m), 8.76 (1H, m). MS (FAB$^+$) m/z 917 (M$^+$)

(b) Allyl (1S,5R,6S)-6-[(1R)-1-(t-butyldimethylsilyloxy)ethyl]-2-[7-dimethoxy(pyridin-3-yl)methylimidazo[5,1-b]thiazol-2-yl]-1-methylcarbapen-2-em-3-carboxylate Toluene (20 ml) was added to 1.90 g of (3S,4R)-1-[allyloxycarbonyl(triphenylphosphoranylidene)methyl]-3-[(1R)-1-(t-butyldimethylsilyloxy)ethyl]-4-{(1R)-1-methyl-2-[7-dimethoxy(pyridin-3-yl)methylimidazo[5,1-b]thiazol-2-yl]-2-oxoethyl}azetidin-2-one, and the mixture was heated under reflux for 3.5 hr. The reaction mixture was concentrated by removing the solvent, and the concentrate was purified by column chromatography on silica gel (eluted with 4% methanol/ethyl acetate) to give 1.04 g of allyl (1S,5R,6S)-6-[(1R)-1-(t-butyldimethylsilyloxy)ethyl]-2-[7-dimethoxy(pyridin-3-yl)methylimidazo-[5,1-b]thiazol-2-yl]-1-methylcarbapen-2-em-3-carboxylate.

$^1$H-NMR (CDCl$^3$) δ: 0.30 (6H, s), 0.91 (9H, s), 1.27 (3H, d, J=4.4 Hz), 1.29 (3H, d, J=5.5 Hz), 3.22 (3H, s), 3.23 (3H, s), 3.30 (1H, dd, J=2.7, 5.5 Hz), 3.35-3.47 (1H, m), 4.23-4.33 (2H, m), 4.68-4.88 (2H, m), 5.25-5.30 (1H, m), 5.40-5.50 (1H, m), 5.90-6.05 (1H, m), 7.23-7.31 (1H, m), 7.90 (1H, s), 7.90-7.95 (1H, m), 8.31 (1H, s), 8.51 (1H, dd, J=1.6, 4.7 Hz), 8.75 (1H, d, J=2.2 Hz)

(c) Allyl (1S,5R,6S)-6-[(1R)-1-(t-butyldimethylsilyloxy)ethyl]-2-[7-(pyridin-3-yl)carbonylimidazo[5,1-b]thiazol-2-yl]-1-methylcarbapen-2-em-3-carboxylate Dimethyl sulfoxide (2 ml) and 1 ml of water were added to a solution of 0.28 g of allyl (1S,5R,6S)-6-[(1R)-1-(t-butyldimethylsilyloxy)ethyl]-2-[7-dimethoxy(pyridin-3-yl)methylimidazo[5,1-b]thiazol-2-yl]-1-methylcarbapen-2-em-3-carboxylate in 12 ml of dioxane, and the mixture was stirred at 90° C. for 36 hr. The reaction mixture was diluted with 50 ml of ethyl acetate, and the diluted reaction mixture was washed three times with 25 ml of water and then with 10% brine. The organic layer was dried over anhydrous magnesium sulfate. The solvent was removed by evaporation, and the residue was purified by column chromatography on silica gel (eluted with ethyl acetate) to give 0.16 g of allyl (1S,5R,6S)-6-[(1R)-1-(t-butyldimethylsilyloxy)ethyl]-2-[7-(pyridin-3-yl)carbonylimidazo[5,1-b]thiazol-2-yl]-1-methylcarbapen-2-em-3-carboxylate. This product was analyzed by NMR. The results were in agreement with the results of analysis in Example 24.

(d) Allyl (1S,5R,6S)-6-[(1R)-1-hydroxyethyl]-2-[7-(pyridin-3-yl)carbonylimidazo[5,1-b]thiazol-2-yl]-1-methylcarbapen-2-em-3-carboxylate Acetic acid (0.23 ml) and 0.72 ml of a 1 M tetrahydrofuran solution of tetrabutylammonium fluoride was added to a solution of 0.14 g of allyl (1S,5R,6S)-6-[(1R)-1-(t-butyldimethylsilyloxy)ethyl]-2-[7-(pyridin-3-yl)carbonylimidazo[5,1-b]thiazol-2-yl]-1-methylcarbapen-2-em-3-carboxylate in 2 ml of tetrahydrofuran, and the mixture was stirred at room temperature for 36 hr. The reaction mixture was diluted with 50 ml of ethyl acetate, and the diluted reaction solution was washed with a 5% aqueous sodium bicarbonate solution and 10% brine in that order. The organic layer was dried, and the solvent was then removed by evaporation. The resultant crude product was purified by column chromatography on silica gel (eluted with 10% methanol/ethyl acetate) to give 60.3 mg of allyl (1S,5R,6S)-6-[(1R)-1-hydroxyethyl]-2-[7-(pyridin-3-yl)carbonylimidazo[5,1-b]thiazol-2-yl]-1-methylcarbapen-2-em-3-carboxylate. This product was analyzed by NMR. The results were in agreement with the results of analysis in Example 26.

Example 33

(3S,4R)-1-[Allyloxycarbonyl(triphenylphosphoranylidene)-methyl]-3-[(1R)-1-(t-butyldimethylsilyloxy)ethyl]-4-{(1R)-1-methyl-2-[7-dimethoxy(pyridin-3-yl)methylimidazo[5,1-b]thiazol-2-yl]-2-oxoethyl}azetidin-2-one

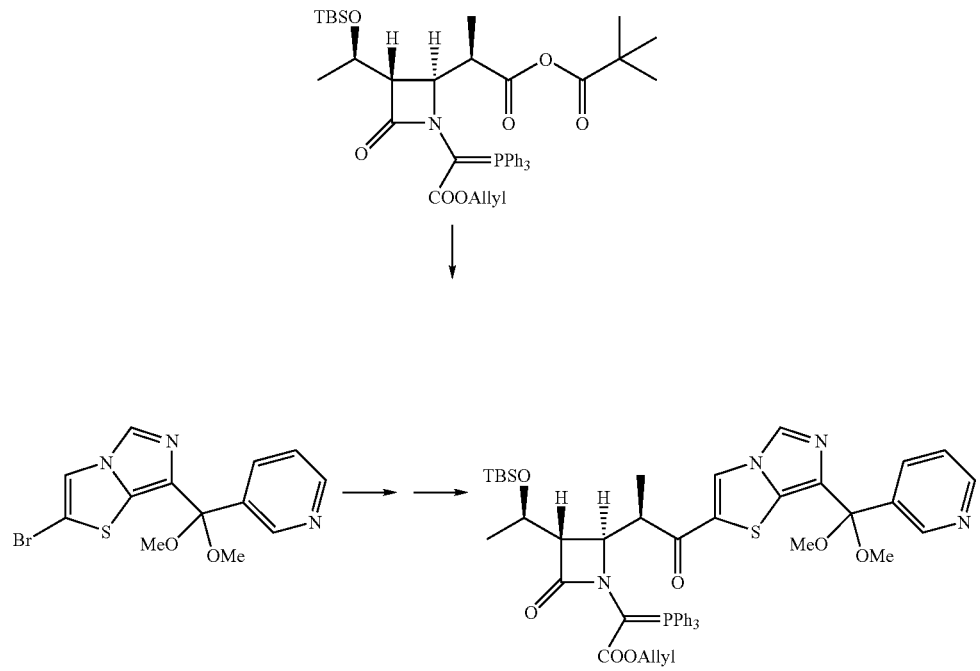

In the same manner as in Example 32, 66 mg of the title compound was prepared from 0.25 g of 2-bromo-7-dimethoxy(pyridin-3-yl)methylimidazo[5,1-b]thiazole and 0.63 g of (3S,4R)-1-[allyloxycarbonyl(triphenylphosphoranylidene)methyl]-3-[(1R)-1-(t-butyldimethylsilyloxy)ethyl]-4-[(1R)-1-(pivaloyloxycarbonyl)ethyl]azetidin-2-one.

Example 34

(3S,4R)-1-[Allyloxycarbonyl(triphenylphosphoranylidene)-methyl]-3-[(1R)-1-(t-butyldimethylsilyloxy)ethyl]-4-{(1R)-1-methyl-2-[7-dimethoxy(pyridin-3-yl)methylimidazo[5,1-b]thiazol-2-yl]-2-oxoethyl}azetidin-2-one

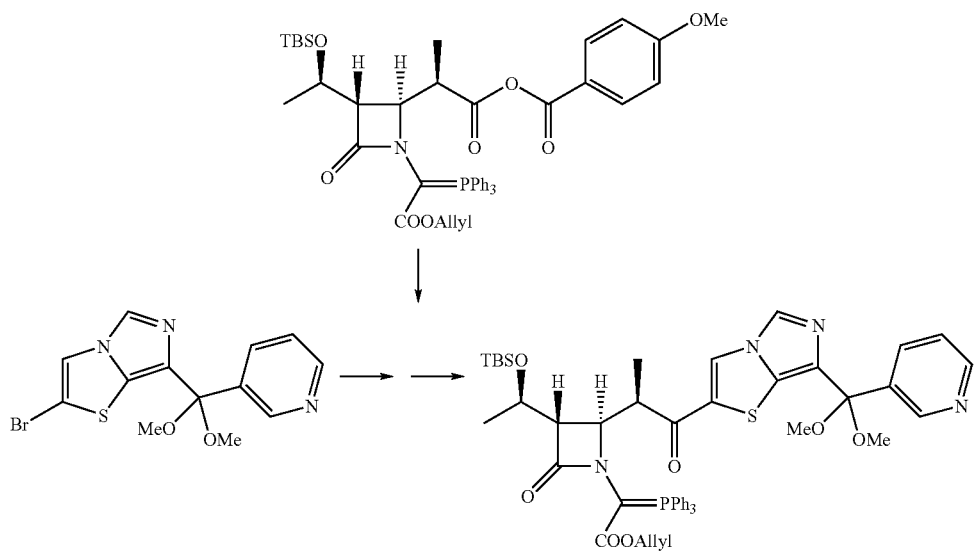

In the same manner as in Example 32, 0.27 g of the title compound was prepared from 0.25 g of 2-bromo-7-dimethoxy(pyridin-3-yl)methylimidazo[5,1-b]thiazole and 0.66 g of (3S,4R)-1-[allyloxycarbonyl(triphenyl phosphoranylidene)methyl]-3-[(1R)-1-(t-butyldimethylsilyloxy)ethyl]-4-[(1R)-1-(4-methoxybenzoyloxycarbonyl)-ethyl]azetidin-2-one.

Example 35

(3S,4R)-1-[Allyloxycarbonyl(triphenylphosphoranylidene)-methyl]-3-[(1R)-1-(t-butyldimethylsilyloxy)ethyl]-4-{(1R)-1-methyl-2-[7-dimethoxy(pyridin-3-yl)methylimidazo[5,1-b]thiazol-2-yl]-2-oxoethyl}azetidin-2-one

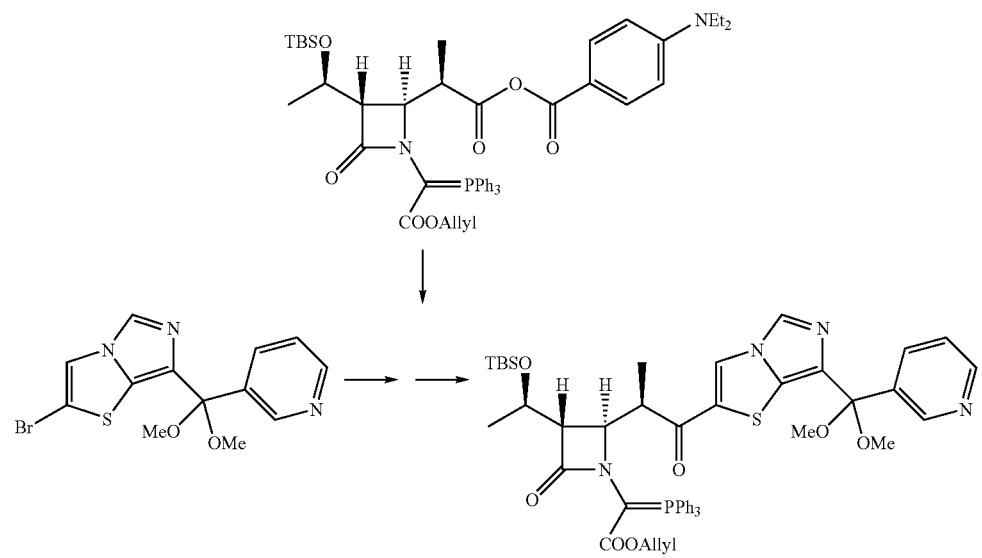

In the same manner as in Example 32, 0.51 g of the title compound was prepared from 0.35 g of 2-bromo-7-dimethoxy(pyridin-3-yl)methylimidazo[5,1-b]thiazole and 1.01 g of (3S,4R)-1-[allyloxycarbonyl(triphenyl phosphoranylidene)methyl]-3-[(1R)-1-(t-butyldimethylsilyloxy)ethyl]-4-[(1R)-1-(4-diethylaminobenzoyloxy-carbonyl)ethyl]azetidin-2-one.

Example 36

(3S,4R)-1-[Allyloxycarbonyl(triphenylphosphoranylidene)-methyl]-3-[(1R)-1-hydroxyethyl]-4-{(1R)-1-methyl-2-[7-(pyridin-3-yl)carbonylimidazo[5,1-b]thiazol-2-yl]-2-oxoethyl}azetidin-2-one

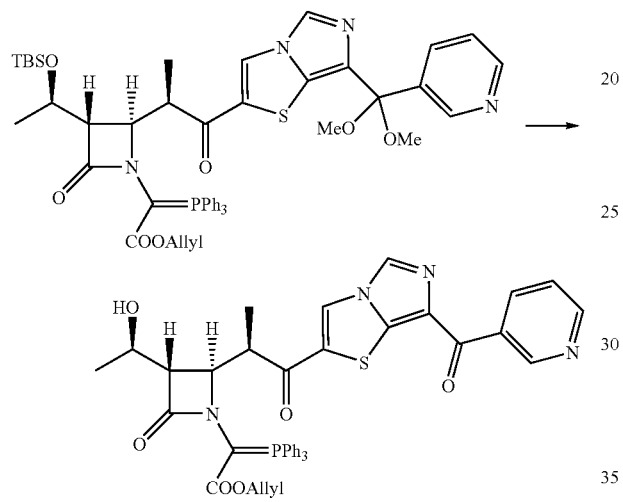

Methanol (0.5 ml) was added to and dissolved in 113 mg of (3S,4R)-1-[allyloxycarbonyl(triphenylphosphoranylidene)methyl]-3-[(1R)-1-(t-butyldimethylsilyloxy)ethyl]-4-[(1R)-1-methyl-2-(7-dimethoxy(pyridin-3-yl)methylimidazo[5,1-b]thiazol-2-yl)-2-oxoethyl]azetidin-2-one, 0.5 ml of −5 N hydrochloric acid was added thereto, and the mixture was stirred at 45° C. for one hr. The reaction mixture was cooled to room temperature, was then neutralized by the addition of a 5% aqueous sodium bicarbonate solution, and was extracted with 20 ml of ethyl acetate. The aqueous layer was reextracted with 10 ml of ethyl acetate. The organic layers were combined, were washed with 10% brine, and were dried over anhydrous magnesium sulfate. The solvent was removed by evaporation, and the residue was purified by chromatography on silica gel (methylene chloride:methanol=15:1) to give 86 mg of (3S,4R)-1-[allyloxycarbonyl(triphenylphosphoranylidene)methyl]-3-[(1R)-1-hydroxyethyl]-4-{(1R)-1-methyl-2-[7-(pyridin-3-yl)carbonylimidazo[5,1-b]thiazol-2-yl]-2-oxoethyl}azetidin-2-one.

$^1$H-NMR (CDCl$_3$) δ: 0.96 (3H, d, J=6.1 Hz), 1.67 (3H, d, J=6.9 Hz), 2.43-3.02 (3H, m), 3.86-4.18 (2H, m), 4.53-4.70 (2H, m), 5.08-5.53 (2H, m), 6.13 (1H, m), 7.45 (1H, m), 7.51-7.79 (16H, m), 8.23 (1H, m), 8.79 (2H, m), 9.71 (1H, m). MS (FAB$^+$) m/z 757 (M$^+$)

Example 37

(3S,4R)-1-[Allyloxycarbonyl(triphenylphosphoranylidene)-methyl]-3-[(1R)-1-(t-butyldimethylsilyloxy)ethyl]-4-[(1R)-1-methyl-2-[7-diethoxy(pyridin-3-yl)methylimidazo[5,1-b]thiazol-2-yl]-2-oxoethyl]azetidin-2-one

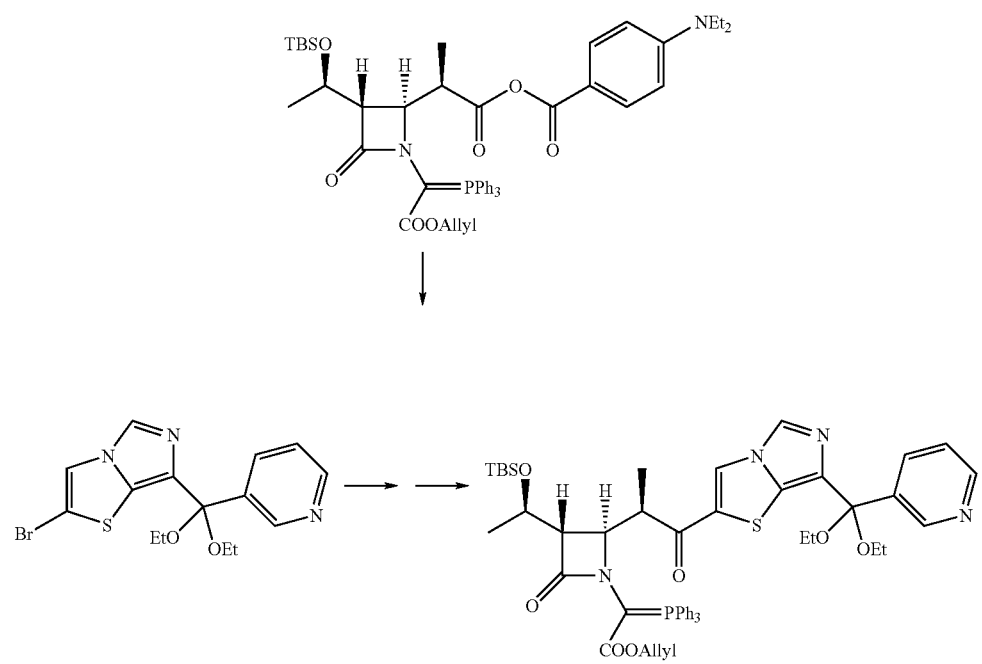

A solution of 0.38 g of 2-bromo-7-diethoxy(pyridin-3-yl)methylimidazo[5,1-b]thiazole in 2 ml of tetrahydrofuran was cooled to −35° C., 1.2 ml of a 0.89 M tetrahydrofuran solution of ethylmagnesium bromide was added thereto, and the mixture was stirred at that temperature for 45 min. The reaction mixture was cooled to −70° C., a solution of 0.88 g of (3S,4R)-1-[allyloxycarbonyl(triphenylphosphoranylidene)methyl]-3-[(1R)-1-(t-butyldimethylsilyloxy)ethyl]-4-[(1R)-1-(4-diethylaminobenzoyloxy-carbonyl)ethyl]azetidin-2-one in 1.5 ml of tetrahydrofuran was added thereto, and the temperature was raised from −45° C. to room temperature with stirring over a period of 4 hr. A saturated aqueous ammonium chloride solution was added to the reaction mixture, and the mixture was extracted with ethyl acetate. The organic layer was washed with dilute hydrochloric acid, a dilute aqueous sodium bicarbonate solution, and a saturated aqueous sodium chloride solution in that order and was dried over anhydrous magnesium sulfate. The solvent was removed by evaporation, and the residue was purified by column chromatography on silica gel (5 to 10% methanol/ethyl acetate) to give 0.58 g of (3S,4R)-1-[allyloxycarbonyl(triphenylphosphoranylidene)methyl]-3-[(1R)-1-(t-butyldimethylsilyloxy)ethyl]-4-[(1R)-1-methyl-2-[7-diethoxy(pyridin-3-yl)methylimidazo[5,1-b]thiazol-2-yl]-2-oxoethyl]azetidin-2-one.

$^1$H-NMR (CDCl$_3$) δ: −0.06 (3H, s), −0.04 (3H, s), 0.81 (9H, s), 0.8-0.9 (3H, m), 1.2-1.3 (6H, m), 1.4-1.6 (3H, m), 2.6-2.7 (1H, m), 2.7-3.0 (2H, m), 3.3-3.5 (4H, m), 3.7-4.0 (1H, m), 4.1-4.3 (1H, m), 4.5-4.7 (2H, m), 5.1-5.3 (1H, m), 5.3-5.5, 6.0-6.1 (1H, m), 7.2-7.3 (1H, m), 7.5-7.7 (9H, m), 7.7-7.9 (6H, m), 7.9-8.0 (2H, m), 8.45-8.55 (2H, m), 8.7-8.8 (1H, m)

Example 38

(3S,4R)-1-[Allyloxycarbonyl(triphenylphosphoranylidene)-methyl]-3-[(1R)-1-hydroxyethyl]-4-[(1R)-1-methyl-2-[7-(pyridin-3-yl)carbonylimidazo[5,1-b]thiazol-2-yl]-2-oxoethyl]azetidin-2-one

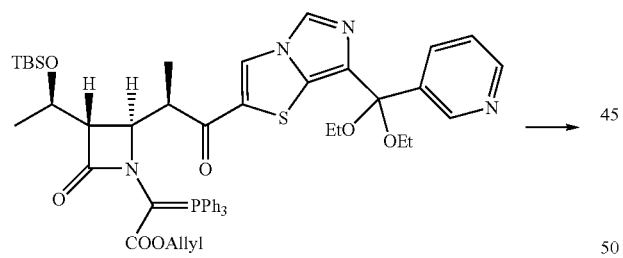

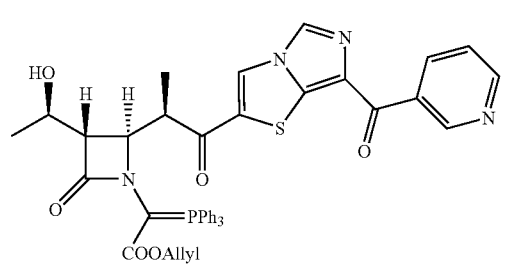

A 5 N aqueous hydrochloric acid solution (2.5 ml) was added to 2.5 ml of a methanol solution of 0.53 g of (3S,4R)-1-[allyloxycarbonyl(triphenylphosphoranylidene)methyl]-3-[(1R)-1-(t-butyldimethylsilyloxy)ethyl]-4-[(1R)-1-methyl-2-[7-diethoxy(pyridin-3-yl)methylimidazo[5,1-b]thiazol-2-yl]-2-oxoethyl]azetidin-2-one at room temperature, and the mixture was stirred at 50° C. for one hr. The reaction mixture was neutralized with a dilute aqueous sodium bicarbonate solution and was extracted with ethyl acetate. The organic layer was washed with a 5% aqueous sodium bicarbonate solution and a 20% aqueous sodium chloride solution in that order and was dried over anhydrous magnesium sulfate. The solvent was removed by evaporation, and the residue was purified by column chromatography on silica gel (2 to 7.5% methanol/methylene chloride) to give 0.41 g of (3S,4R)-1-[allyloxycarbonyl(triphenylphosphoranylidene)methyl]-3-[(1R)-1-hydroxyethyl]-4-[(1R)-1-methyl-2-[7-(pyridin-3-yl)carbonylimidazo[5,1-b]thiazol-2-yl]-2-oxoethyl]azetidin-2-one. This product was analyzed by NMR. The results were in agreement with the results of analysis in Example 36.

Example 39

Allyl (1S,5R,6S)-6-[(1R)-1-hydroxyethyl]-2-[7-(pyridin-3-yl)carbonylimidazo[5,1-b]thiazol-2-yl]-1-methylcarbapen-2-em-3-carboxylate

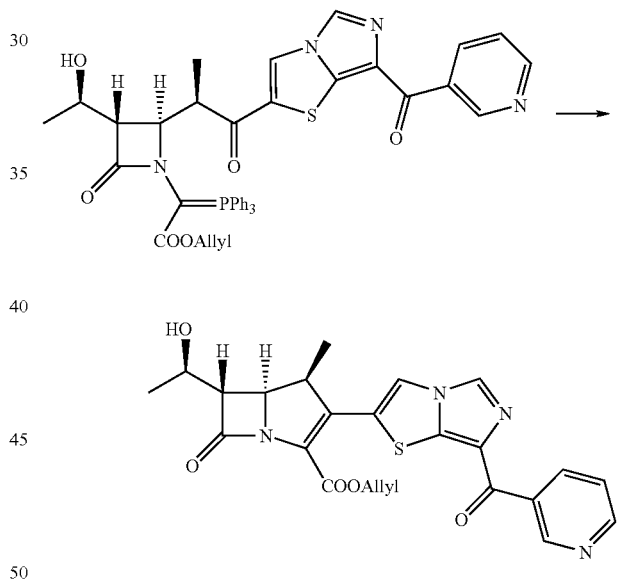

Toluene (20 ml) was added to 0.76 g of (3S,4R)-1-[allyloxycarbonyl(triphenylphosphoranylidene)methyl]-3-[(1R)-1-hydroxyethyl]-4-[(1R)-1-methyl-2-[7-(pyridin-3-yl)carbonylimidazo[5,1-b]thiazol-2-yl]-2-oxoethyl]azetidin-2-one, and the mixture was heated under reflux for 2 hr. The reaction solution was concentrated by removing the solvent, and the concentrate was purified by column chromatography on silica gel (eluted with 5 to 10% methanol/ethyl acetate). The eluate containing the contemplated product was concentrated, and the resultant solid was washed with a hexane:ethyl acetate=1:1 solution to give 0.38 g of allyl (1S,5R,6S)-6-[(1R)-1-hydroxyethyl]-2-[7-(pyridin-3-yl)carbonylimidazo[5,1-b]thiazol-2-yl]-1-methylcarbapen-2-em-3-carboxylate. This product was analyzed by NMR. The results were in agreement with the results of analysis in Example 26.

Example 40

(3S,4R)-1-[Allyloxycarbonyl(triphenylphosphoranylidene)-methyl]-3-[(1R)-1-(t-butyldimethylsilyloxy)ethyl]-4-[(1R)-1-methyl-2-[7-(pyridin-3-yl)dimethylhydrazonoylimidazo[5,1-b]thiazol-2-yl]-2-oxoethyl]azetidin-2-one

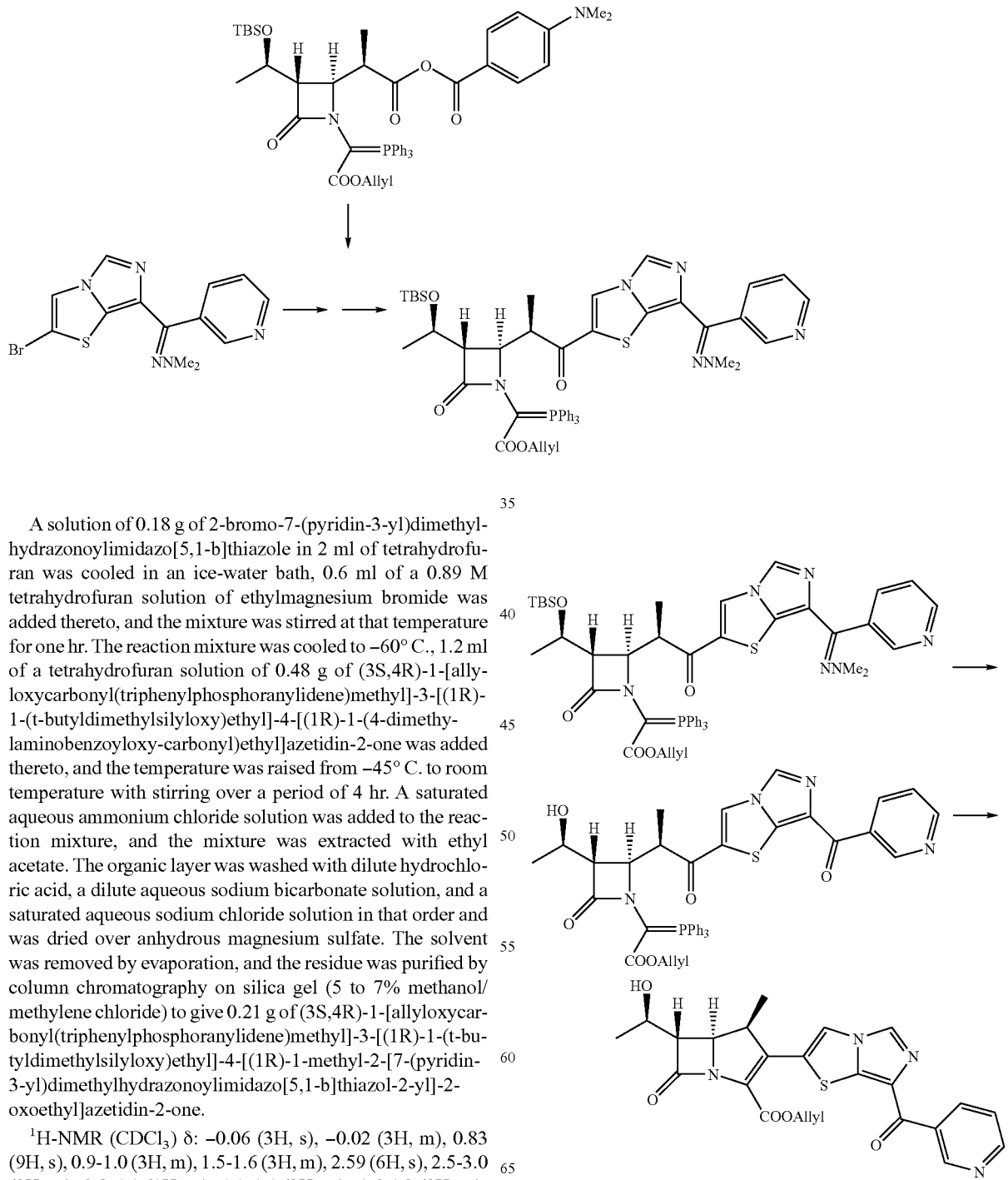

A solution of 0.18 g of 2-bromo-7-(pyridin-3-yl)dimethylhydrazonoylimidazo[5,1-b]thiazole in 2 ml of tetrahydrofuran was cooled in an ice-water bath, 0.6 ml of a 0.89 M tetrahydrofuran solution of ethylmagnesium bromide was added thereto, and the mixture was stirred at that temperature for one hr. The reaction mixture was cooled to −60° C., 1.2 ml of a tetrahydrofuran solution of 0.48 g of (3S,4R)-1-[allyloxycarbonyl(triphenylphosphoranylidene)methyl]-3-[(1R)-1-(t-butyldimethylsilyloxy)ethyl]-4-[(1R)-1-(4-dimethylaminobenzoyloxy-carbonyl)ethyl]azetidin-2-one was added thereto, and the temperature was raised from −45° C. to room temperature with stirring over a period of 4 hr. A saturated aqueous ammonium chloride solution was added to the reaction mixture, and the mixture was extracted with ethyl acetate. The organic layer was washed with dilute hydrochloric acid, a dilute aqueous sodium bicarbonate solution, and a saturated aqueous sodium chloride solution in that order and was dried over anhydrous magnesium sulfate. The solvent was removed by evaporation, and the residue was purified by column chromatography on silica gel (5 to 7% methanol/methylene chloride) to give 0.21 g of (3S,4R)-1-[allyloxycarbonyl(triphenylphosphoranylidene)methyl]-3-[(1R)-1-(t-butyldimethylsilyloxy)ethyl]-4-[(1R)-1-methyl-2-[7-(pyridin-3-yl)dimethylhydrazonoylimidazo[5,1-b]thiazol-2-yl]-2-oxoethyl]azetidin-2-one.

$^1$H-NMR (CDCl$_3$) δ: −0.06 (3H, s), −0.02 (3H, m), 0.83 (9H, s), 0.9-1.0 (3H, m), 1.5-1.6 (3H, m), 2.59 (6H, s), 2.5-3.0 (3H, m), 3.8-4.1 (1H, m), 4.1-4.4 (2H, m), 4.6-4.8 (2H, m), 5.2-5.4 (1H, m), 7.3-7.4 (1H, m), 7.5-7.7 (9H, m), 7.8-7.9 (6H, m), 8.0-8.1 (1H, m), 8.1-8.3 (2H, m), 8.65-8.75 (1H, m), 8.9-9.0 (1H, m)

Example 41

Allyl (1S,5R,6S)-6-[(1R)-1-hydroxyethyl]-2-[7-(pyridin-3-yl)carbonylimidazo[5,1-b]thiazol-2-yl]-1-methylcarbapen-2-em-3-carboxylate A 5 N aqueous hydrochloric acid solution (1 ml) was added to a solution of 0.21 g of (3S,4R)-1-[allyloxycarbonyl(triphenylphosphoranylidene)methyl]-3-[(1R)-1-(t-butyldimethylsilyloxy)ethyl]-4-[(1R)-1-methyl-2-[7-(pyridin-3-yl)dimethylhydrazonoylimidazo[5,1-b]thiazol-2-yl]-2-oxoethyl]azetidin-2-one in 1 ml of methanol at room temperature, and the mixture was stirred at 50° C. for 8 hr. The reaction mixture was neutralized with a dilute aqueous sodium bicarbonate solution and was extracted with methylene chloride. The organic layer was washed with a 5% aqueous sodium bicarbonate solution and a 20% aqueous sodium chloride solution in that order and was dried over anhydrous magnesium sulfate. The solvent was removed by evaporation to give a crude product of (3S,4R)-1-[allyloxycarbonyl(triphenylphosphoranylidene)methyl]-3-[(1R)-1-hydroxyethyl]-4-[(1R)-1-methyl-2-[7-(pyridin-3-yl)carbonylimidazo[5,1-b]thiazol-2-yl]-2-oxoethyl]azetidin-2-one. Toluene (5 ml) was added to the crude product, and the mixture was heated under reflux for 2.5 hr. The solvent was removed by evaporation, and the residue was purified by thin layer chromatography (developed with 10% methanol/methylene chloride) to give 64.1 mg of allyl (1S,5R,6S)-6-[(1R)-1-hydroxyethyl]-2-[7-(pyridin-3-yl)carbonylimidazo[5,1-b]thiazol-2-yl]-1-methylcarbapen-2-em-3-carboxylate. This product was analyzed by NMR. The results were in agreement with the results of analysis in Example 26.

Example 42

(3S,4R)-3-[(1R)-1-(t-Butyldimethylsilyloxy)ethyl]-4-{(1R)-1-methyl-2-[7-dimethoxy(pyridin-3-yl)methylimidazo[5,1-b]thiazol-2-yl]-2-oxoethyl]-1-[4-nitrobenzyloxycarbonyl (triphenylphosphoranylidene)-methyl]azetidin-2-one In the same manner as in Example 32, 0.54 g of (3S,4R)-3-[(1R)-1-(t-butyldimethylsilyloxy)ethyl]-4-{(1R)-1-methyl-2-[7-dimethoxy(pyridin-3-yl)methylimidazo[5,1-b]thiazol-2-yl]-2-oxoethyl]-1-[4-nitrobenzyloxycarbonyl (triphenyl phosphoranylidene)methyl]azetidin-2-one was prepared from 0.36 g of 2-bromo-7-dimethoxy(pyridin-3-yl)methylimidazo[5,1-b]thiazole and 1.09 g of (3S,4R)-3-[(1R)-1-(t-butyldimethylsilyloxy)ethyl]-4-[(1R)-1-(4-dimethylaminobenzoyloxy-carbonyl)ethyl]-1-[4-nitrobenzyloxycarbonyl (triphenylphosphoranylidene)-methyl]-azetidin-2-one.

$^1$H-NMR (CDCl$_3$) δ: −0.10 (6H, m), 0.80 (9H, 2s), 0.96 (3H, m), 1.46 (3H, m), 2.64-2.89 (3H, m), 3.53 (3H, 3s), 3.51-3.93 (1H, m), 4.82-5.34 (2H, m), 6.71 (2H, d, J=8.5 Hz), 7.26 (1H, m), 7.48-7.91 (16H, m), 7.99 (1H, s), 8.20 (2H, d, J=8.5 Hz), 8.52 (1H, m), 8.75 (1H, m). MS (FAB$^+$) m/z 1012 (MH$^+$)

Example 43

(3S,4R)-3-[(1R)-1-Hydroxyethyl]-4-{(1R)-1-methyl-2-[7-(pyridin-3-yl)carbonylimidazo[5,1-b]thiazol-2-yl]-2-oxoethyl}-1-[4-nitrobenzyloxycarbonyl(triphenylphosphoranylidene)methyl]azetidin-2-one

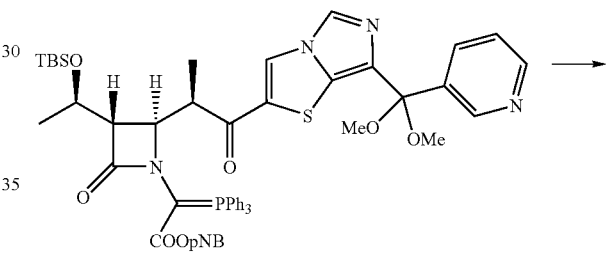

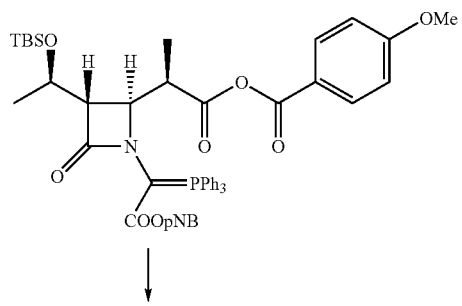

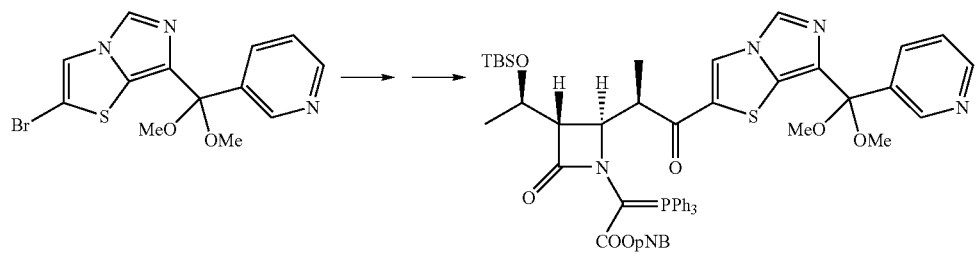

-continued

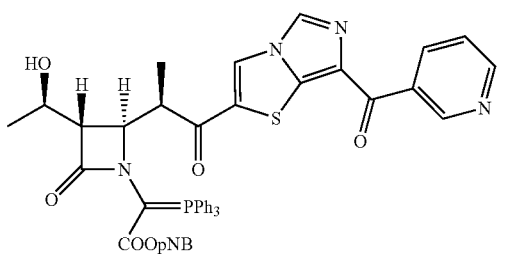

In the same manner as in Example 36, 84 mg of (3S,4R)-3-[(1R)-1-hydroxyethyl]-4-{(1R)-1-methyl-2-[7-(pyridin-3-yl)carbonylimidazo[5,1-b]thiazol-2-yl]-2-oxoethyl}-1-[4-nitrobenzyloxycarbonyl(triphenyl-phosphoranylidene)methyl]azetidin-2-one was prepared from 110 mg of (3S,4R)-3-[(1R)-1-(t-butyldimethylsilyloxy)ethyl]-4-{(1R)-1-methyl-2-[7-dimethoxy(pyridin-3-yl)methylimidazo[5,1-b]thiazol-2-yl]-2-oxoethyl}-1-[4-nitrobenzyloxycarbonyl(triphenyl phosphoranylidene)methyl]azetidin-2-one. This product was analyzed by NMR. The results were in agreement with the results of analysis in Example 29. MS (FAB$^+$) m/Z 852 (MH$^+$)

Example 44

(4-Nitrobenzyl) (1S,5R,6S)-6-[(1R)-1-hydroxyethyl]-1-methyl-2-[7-(pyridin-3-yl)carbonylimidazo[5,1-b]thiazol-2-yl]-1-carbapen-2-em-3-carboxylate In the same manner as in Example 30, 48 mg of (4-nitrobenzyl) (1S,5R,6S)-6-[(1R)-1-hydroxyethyl]-1-methyl-2-[7-(pyridin-3-yl)carbonylimidazo[5,1-b]thiazol-2-yl]-1-carbapen-2-em-3-carboxylate was prepared from 84 mg of (3S,4R)-3-[(1R)-1-hydroxyethyl]-4-{(1R)-1-methyl-2-[7-(pyridin-3-yl)carbonylimidazo[5,1-b]thiazol-2-yl]-2-oxoethyl}-1-[4-nitrobenzyloxycarbonyl(triphenylphosphoranylidene)methyl]azetidin-2-one. This product was analyzed by NMR. The results were in agreement with the results of analysis in Example 30. MS (FAB$^+$) m/z 574 (MH$^+$)

Example 45

(3S,4R)-1-[Allyloxycarbonyl(triphenylphosphoranylidene)-methyl]-3-(1R)-1-hydroxyethyl]-4-{(1R)-1-methyl-2-[7-(pyridin-3-yl)carbonylimidazo[5,1-b]thiazol-2-yl]-2-oxoethyl}azetidin-2-one

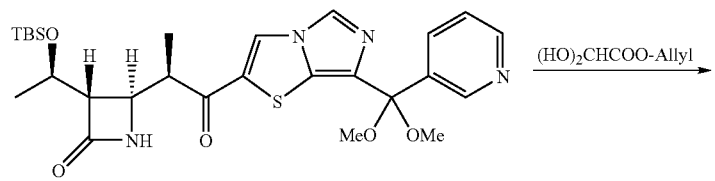

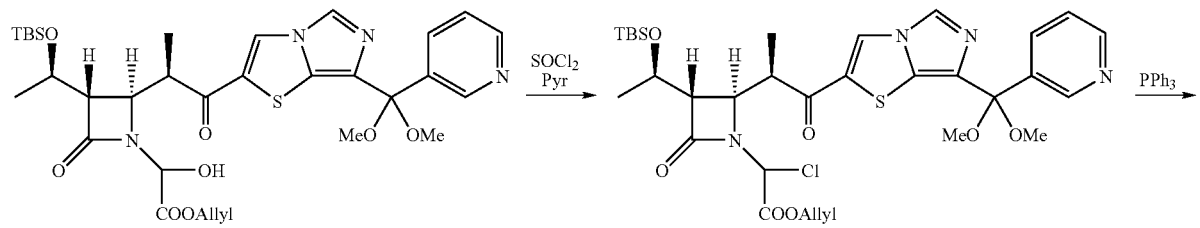

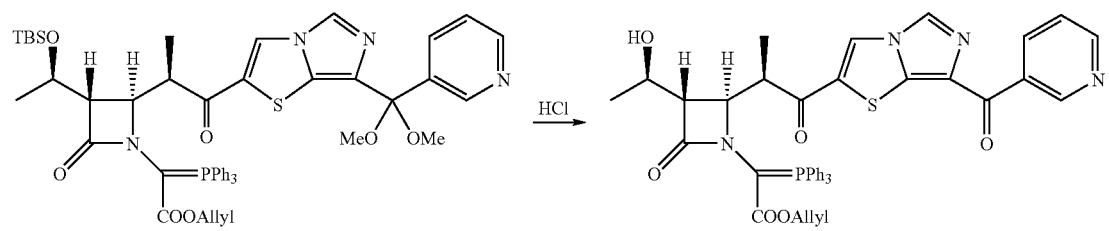

(a) (3S,4R)-1-[(Allyloxycarbonyl)hydroxymethyl]-3-[(1R)-1-(tert-butyldimethylsilyloxy)ethyl]-4-[(1R)-1-methyl-2-[7-dimethoxy(pyridin-3-yl)methylimidazo[5,1-b]thiazol-2-yl]-2-oxoethyl]azetidin-2-one A solution of 45 mg of allyl glyoxylate monohydrate in 1.5 ml of toluene, 266 mg of anhydrous sodium sulfate, and 1 ml of toluene were added to a suspension of 104 mg of (3S,4R)-3-[(1R)-1-(tert-butyldimethylsilyloxy)ethyl]-4-[(1R)-1-methyl-2-[7-dimethoxy(pyridin-3-yl)methylimidazo[5,1-b]thiazol-2-yl]-2-oxoethyl]azetidin-2-one in 0.5 ml of toluene at room temperature under an argon atmosphere, and the mixture was then stirred at 70° C. for 3 days. The reaction mixture was allowed to cool to room temperature and was diluted with tetrahydrofuran. The insolubles were then removed, and the solvent was removed by evaporation to give a crude product of (3S,4R)-1-[(allyloxycarbonyl)hydroxymethyl]-3-[(1R)-1-(tert-butyldimethylsilyloxy)-ethyl]-4-[(1R)-1-methyl-2-[7-dimethoxy(pyridin-3-yl)methylimidazo[5,1-b]thiazol-2-yl]-2-oxoethyl]azetidin-2-one.

(b) (3S,4R)-1-[(Allyloxycarbonyl)chloromethyl]-3-[(1R)-1-(tert-butyldimethylsilyloxy)ethyl]-4-[(1R)-1-methyl-2-[7-dimethoxy(pyridin-3-yl)methylimidazo[5,1-b]thiazol-2-yl]-2-oxoethyl]azetidin-2-one A solution of the crude product of (3S,4R)-1-[(allyloxycarbonyl)hydroxymethyl]-3-[(1R)-1-(tert-butyldimethylsilyloxy)-ethyl]-4-[(1R)-1-methyl-2-[7-dimethoxy(pyridin-3-yl)methylimidazo[5,1-b]thiazol-2-yl]-2-oxoethyl]azetidin-2-one in 1 ml of tetrahydrofuran was cooled to −50° C. under an argon atmosphere. A solution of 0.028 ml of pyridine in 1.5 ml of tetrahydrofuran and a solution of 0.025 ml of thionyl chloride in 1.5 ml of tetrahydrofuran were added thereto in that order. After the temperature was brought to −20° C., the mixture was further stirred at that temperature for one hr. The reaction mixture was diluted with tetrahydrofuran, and the insolubles were then removed. The solvent was removed by evaporation to give a crude product of (3S,4R)-1-[(allyloxycarbonyl)chloromethyl]-3-[(1R)-1-(tert-butyldimethylsilyloxy)-ethyl]-4-[(1R)-1-methyl-2-[7-dimethoxy(pyridin-3-yl)methylimidazo[5,1-b]thiazol-2-yl]-2-oxoethyl]azetidin-2-one.

(c) (3S,4R)-1-[Allyloxycarbonyl(triphenylphosphoranylidene)-methyl]-3-[(1R)-1-(tert-butyldimethylsilyloxy)ethyl]-4-[(1R)-1-methyl-2-[7-dimethoxy(pyridin-3-yl)methylimidazo[5,1-b]thiazol-2-yl]-2-oxoethyl]azetidin-2-one Triphenylphosphine (92 mg) was added to a solution of the crude product of (3S,4R)-1-[(allyloxycarbonyl)chloromethyl]-3-[(1R)-1-(tert-butyldimethylsilyloxy)ethyl]-4-[(1R)-1-methyl-2-[7-dimethoxy(pyridin-3-yl)methylimidazo[5,1-b]thiazol-2-yl]-2-oxoethyl]azetidin-2-one in 2 ml of dimethylformamide under an argon atmosphere at room temperature, and the mixture was stirred at that temperature for 20 hr. The reaction mixture was diluted with ethyl acetate, saturated brine was added to the diluted reaction mixture, and the mixture was neutralized with sodium hydrogencarbonate, followed by extraction with ethyl acetate. The organic layer was washed with saturated brine and was then dried over anhydrous magnesium sulfate. The solvent was removed by evaporation to give a crude product of (3S,4R)-1-[allyloxycarbonyl(triphenylphosphoranylidene)-methyl]-3-[(1R)-1-(tert-butyldimethylsilyloxy)ethyl]-4-[(1R)-1-methyl-2-[7-dimethoxy(pyridin-3-yl)methylimidazo[5,1-b]thiazol-2-yl]-2-oxoethyl]azetidin-2-one.

(d) (3S,4R)-1-[Allyloxycarbonyl(triphenylphosphoranylidene)-methyl]-3-(1R)-1-hydroxyethyl]-4-{(1R)-1-methyl-2-[7-(pyridin-3-yl)carbonylimidazo[5,1-b]thiazol-2-yl]-2-oxoethyl}azetidin-2-one A 5 N aqueous hydrochloric acid solution (1 ml) was added to a solution of (3S,4R)-1-[allyloxycarbonyl(triphenylphosphoranylidene)-methyl]-3-[(1R)-1-(tert-butyldimethylsilyloxy)ethyl]-4-[(1R)-1-methyl-2-[7-dimethoxy(pyridin-3-yl)methylimidazo[5,1-b]thiazol-2-yl]-2-oxoethyl]-azetidin-2-one in 1 ml of methanol, and the mixture was stirred at 45° C. for 30 min. The reaction mixture was allowed to cool to room temperature, ethyl acetate and 10% sodium chloride were added thereto, and the aqueous layer was washed with ethyl acetate. The aqueous layer was neutralized with sodium hydrogencarbonate and was then extracted with ethyl acetate. The organic layer was washed with saturated sodium hydrogencarbonate and saturated brine in that order and was then dried over anhydrous magnesium sulfate. The solvent was removed by evaporation, and the residue was purified by column chromatography on silica gel to give 30 mg of (3S,4R)-1-[allyloxycarbonyl(triphenylphosphoranylidene)methyl]-3-(1R)-1-hydroxyethyl]-4-{(1R)-1-methyl-2-[7-(pyridin-3-yl)carbonylimidazo[5,1-b]thiazol-2-yl]-2-oxoethyl}azetidin-2-one. The results of analysis by NMR and MS were in agreement with the results of analysis in Example 36.

Example A-1

Allyl (1S,5R,6S)-2-[7-(1-carbamoylmethyl pyridinium-3-yl)carbonylimidazo[5,1-b]thiazol-2-yl]-6-[(1R)-1-hydroxyethyl]-1-methylcarbapen-2-em-3-carboxylate iodide 2-Iodoacetamide (1.13 g) was added to a solution of 1.46 g of allyl (1S,5R,6S)-6-[(1R)-1-hydroxyethyl]-2-[7-(pyridin-3-yl)carbonyl-imidazo[5,1-b]thiazol-2-yl]-1-methylcarbapen-2-em-3-carboxylate in 4.5 ml of methanol, and the mixture was stirred at 40° C. for 22 hr. Methanol (8 ml) was added thereto for dilution. The diluted reaction mixture was added dropwise to 180 ml of ethyl acetate, and the resultant powder was collected by filtration to give 1.80 g of allyl (1S,5R,6S)-2-[7-(1-carbamoylmethylpyridinium-3-yl)carbonylimidazo[5,1-b]thiazol-2-yl]-6-[(1R)-1-hydroxyethyl]-1-methylcarbapen-2-em-3-carboxylate iodide.

$^1$H-NMR (DMSO-$d_6$) δ: 1.18 (3H, d, J=6.3 Hz), 1.24 (3H, d, J=7.1 Hz), 3.43 (1H, dd, J=2.5, 5.5 Hz), 3.74-3.85 (1H, m), 3.98-4.35 (1H, m), 4.35 (1H, dd, J=2.7, 9.6 Hz), 4.70-4.90 (2H, m), 5.17 (1H, d, J=5.2 Hz), 5.23-5.39 (1H, m), 5.42-5.50 (1H, m), 5.55 (2H, s), 5.90-6.03 (1H, m), 7.76 (1H, s), 8.07 (1H, s), 8.37 (1H, dd, J=6.3, 8.2 Hz), 8.58 (1H, s), 8.71 (1H, s), 9.15 (1H, d, J=6.3 Hz), 9.58 (1H, d, J=8.2 Hz), 9.76 (1H, s)

Example A-2

(1S,5R,6S)-2-[7-(1-Carbamoylmethylpyridinium-3-yl)carbonylimidazo[5,1-b]thiazol-2-yl]-6-[(1R)-1-hydroxyethyl]-1-methylcarbapen-2-em-3-carboxylate A solution of 0.28 g of dimedone, 0.13 g of sodium bicarbonate, and 0.06 ml of triethyl phosphite in 1 ml of water and 3 ml of tetrahydrofuran was stirred at room temperature for 10 min. The atmosphere was then replaced by argon, 22.4 mg of palladium acetate was added thereto, and the mixture was stirred for 10 min. Allyl (1S,5R,6S)-2-[7-(1-carbamoylmethylpyridinium-3-yl)carbonylimidazo[5,1-b]thiazol-2-yl]-6-[(1R)-1-hydroxyethyl]-1-methylcarbapen-2-em-3-carboxylate iodide (0.66 g) was added thereto, and the mixture was stirred at 40° C. for 2 hr. The reaction mixture was stirred in an ice-water bath for 30 min, and the resultant precipitate was collected by filtration to give 0.47 g of a crude product of (1S,5R,6S)-2-[7-(1-carbamoylmethylpyridinium-3-yl)carbonylimidazo[5,1-b]thiazol-2-yl]-6-[(1R)-1-hydroxyethyl]-1-methylcarbapen-2-em-3-carboxylate. This crude product was dissolved in 2 ml of water, and the solution was filtered through a filter with a pore diameter of 0.45 μm, followed by washing three times with 0.5 ml of water. The filtrate and the wash liquids were combined, and stirring was carried out at 4° C. for 12 hr. The resultant precipitate was collected by filtration to give 0.35 g of (1S,5R,6S)-2-[7-(1-carbamoylmethylpyridinium-3-yl)carbonylimidazo[5,1-b]thiazol-2-yl]-6-[(1R)-1-hydroxyethyl]-1-methylcarbapen-2-em-3-carboxylate.

$^1$H-NMR (DMSO-d$_6$) δ: 1.15-1.25 (6H, m), 3.15 (1H, dd, J=2.7, 6.9 Hz), 3.43-3.53 (1H, m), 3.90-4.00 (1H, m), 4.10 (1H, d, J=2.5, 9.3 Hz), 5.07 (1H, d, J=5.2 Hz), 5.07-5.20 (2H, m), 7.75 (1H, s), 8.28 (1H, s), 8.34 (1H, s), 8.31-8.36 (2H, m), 9.15 (1H, d, J=6.3 Hz), 9.51 (1H, d, J=8.2 Hz), 9.79 (1H, s)

Example A-3

(1S,5R,6S)-2-[7-(1-Carbamoylmethylpyridinium-3-yl)carbonylimidazo[5,1-b]thiazol-2-yl]-6-[(1R)-1-hydroxyethyl]-1-methylcarbapen-2-em-3-carboxylate Sodium bicarbonate (6.72 g), 10.4 ml of N-methylaniline, and 4.8 ml of triethyl phosphite were added in that order to 320 ml of a mixed liquid of 2-propanol:water=3:2. The atmosphere was replaced by argon, and the mixture was stirred at room temperature for 15 min. Palladium acetate (0.90 g) was then added thereto, and the mixture was stirred for 10 min. A solution of 59.31 g of allyl(1S,5R,6S)-2-[7-(1-carbamoylmethylpyridinium-3-yl)carbonylimidazo[5,1-b]thiazol-2-yl]-6-[(1R)-1-hydroxyethyl]-1-methylcarbapen-2-em-3-carboxylate iodide in 400 ml of a mixed liquid of 2-propanol:water=3:2 was added to the reaction mixture, and the mixture was stirred at 30° C. for one hr. 2-Propanol (80 ml) was added to the reaction mixture, and the mixture was stirred in an ice-water bath for one hr. The resultant precipitate was then collected by filtration and was washed with 265 ml of a cooled mixed liquid of 2-propanol:water=2:1, 53 ml of 2-propanol, and 106 ml of acetone in that order to give 7.168 g of (1S,5R,6S)-2-[7-(1-carbamoylmethylpyridinium-3-yl)carbonylimidazo[5,1-b]thiazol-2-yl]-6-[(1R)-1-hydroxyethyl]-1-methylcarbapen-2-em-3-carboxylate. This product was analyzed by NMR. The results were in agreement with the results of analysis in Example A-2.

$^1$H-NMR (DMSO-d$_6$) δ: 1.15-1.25 (6H, m), 3.15 (1H, dd, J=2.7, 6.9 Hz), 3.43-3.53 (1H, m), 3.90-4.00 (1H, m), 4.10 (1H, dd, J=2.5, 9.3 Hz), 5.07 (1H, d, J=5.2 Hz), 5.07-5.20 (2H, m), 7.75 (1H, s), 8.28 (1H, s), 8.34 (1H, s), 8.31-8.36 (2H, m), 9.15 (1H, d, J=6.3 Hz), 9.51 (1H, d, J=8.2 Hz), 9.79 (1H, s)

The invention claimed is:

1. A compound of formula (14):

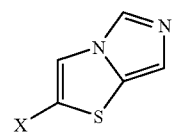
(14)

wherein X represents a halogen atom.

2. A compound according to claim 1, wherein the compound is a compound of formula (14a):

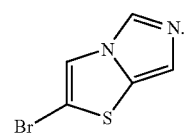
(14a)

3. A process for producing a compound of formula (14), comprising steps (a) and (b):

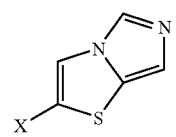
(14)

wherein X represents a halogen atom,
(a) reacting a compound of formula (15) with a halogenating agent to give a compound of formula (16) which, optionally after the removal of a protective group, undergoes formylation of amino to give a compound of formula (17):

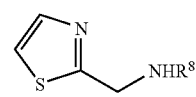
(15)

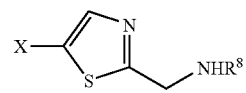
(16)

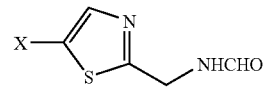
(17)

wherein
R$^8$ represents a hydrogen atom, or a protective group of amino and,
X represents a halogen atom, and
(b) reacting the compound of formula (17) with a dehydrating agent for cyclization to give a compound of formula (14).

4. The process according to claim 3, wherein X represents a bromine atom.

* * * * *